US011524063B2

(12) United States Patent
Krishna et al.

(10) Patent No.: US 11,524,063 B2
(45) Date of Patent: Dec. 13, 2022

(54) MATERIALS AND METHODS RELATING TO IMMUNOGENIC EPITOPES FROM HUMAN PAPILLOMAVIRUS

(71) Applicants: ARIZONA BOARD OF REGENTS ON BEHALF OF ARIZONA STATE UNIVERSITY, Scottsdale, AZ (US); ICAHN SCHOOL OF MEDICINE AT MOUNT SINAI, New York, NY (US); BAYLOR COLLEGE OF MEDICINE, Houston, TX (US)

(72) Inventors: Sri Krishna, North Bethesda, MD (US); Marshall Posner, Mount Vernon, NY (US); Andrew Sikora, Houston, TX (US); Karen Anderson, Scottsdale, AZ (US)

(73) Assignees: ARIZONA BOARD OF REGENTS ON BEHALF OF ARIZONA STATE UNIVERSITY, Scottsdale, AZ (US); ICAHN SCHOOL OF MEDICINE AT MOUNT SINAI, New York, NY (US); BAYLOR COLLEGE OF MEDICINE, Houston, TX (US)

(*) Notice: Subject to any disclaimer, the term of this patent is extended or adjusted under 35 U.S.C. 154(b) by 0 days.

(21) Appl. No.: 16/762,085

(22) PCT Filed: Nov. 15, 2018

(86) PCT No.: PCT/US2018/061362
§ 371 (c)(1),
(2) Date: May 6, 2020

(87) PCT Pub. No.: WO2019/099723
PCT Pub. Date: May 23, 2019

(65) Prior Publication Data
US 2021/0205435 A1    Jul. 8, 2021

Related U.S. Application Data

(60) Provisional application No. 62/586,517, filed on Nov. 15, 2017.

(51) Int. Cl.
| | | |
|---|---|---|
| A61K 39/12 | (2006.01) | |
| A61P 31/20 | (2006.01) | |
| A61P 35/00 | (2006.01) | |
| A61K 39/00 | (2006.01) | |

(52) U.S. Cl.
CPC .............. *A61K 39/12* (2013.01); *A61P 31/20* (2018.01); *A61P 35/00* (2018.01); *A61K 2039/80* (2018.08)

(58) Field of Classification Search
None
See application file for complete search history.

(56) References Cited

U.S. PATENT DOCUMENTS

| | | | |
|---|---|---|---|
| 7,202,034 B2* | 4/2007 | Van Der Burg | ........ A61P 31/04 435/6.14 |
| 9,857,374 B2 | 1/2018 | Labaer et al. | |
| 10,591,474 B2 | 3/2020 | Katchman et al. | |
| 10,802,026 B2 | 10/2020 | Labaer et al. | |
| 2007/0055049 A1* | 3/2007 | Grey | .................. A61K 39/0011 530/350 |
| 2010/0196353 A1* | 8/2010 | Van Der Burg | ........ A61P 35/00 514/1.1 |
| 2015/0362497 A1 | 12/2015 | Anderson et al. | |
| 2017/0045515 A1 | 2/2017 | Anderson et al. | |
| 2017/0059563 A1 | 3/2017 | Smith et al. | |
| 2017/0176423 A1 | 6/2017 | Anderson et al. | |
| 2017/0177788 A1 | 6/2017 | Anderson et al. | |
| 2017/0205409 A1 | 7/2017 | Anderson et al. | |
| 2017/0363631 A1 | 12/2017 | Labaer et al. | |
| 2018/0320230 A1 | 11/2018 | Labaer et al. | |
| 2019/0290248 A1 | 9/2019 | Katchman et al. | |
| 2019/0302122 A1 | 10/2019 | Katchman et al. | |
| 2020/0182874 A1 | 6/2020 | Labaer et al. | |
| 2020/0191782 A1 | 6/2020 | Katchman et al. | |
| 2020/0377871 A1 | 12/2020 | Ewaisha et al. | |
| 2020/0400671 A1 | 12/2020 | Labaer et al. | |

FOREIGN PATENT DOCUMENTS

| | | |
|---|---|---|
| EP | 1288292 A1 | 3/2003 |
| WO | 2005060993 A1 | 7/2005 |

OTHER PUBLICATIONS

Accardi et al., Retinoblastoma-independent antiproliferative activity of novel intracellular antibodies against the E7 oncoprotein in HPV 16-positive cells. BMC Cancer 2011, 11:17.*
Grabowska et al. Identification of promiscuous HPV16-derived T helper cell epitopes for therapeutic HPV vaccine design. Int. J. Cancer: 136, 212-224 (2015).*
Albers et al. Antitumor Activity of Human Papillomavirus Type 16 E7-Specific T Cells against Virally Infected Squamous Cell Carcinoma of the Head and Neck. Cancer Res 2005; 65(23): 11146-55.*
Mandal R et al. The head and neck cancer immune landscape and its immunotherapeutic implications. JCI Insight. Oct. 20, 2016;1(17):e89829.*

(Continued)

*Primary Examiner* — Nianxiang Zou
(74) *Attorney, Agent, or Firm* — Michael Best & Friedrich LLP

(57) ABSTRACT

Embodiments of the present disclosure pertain generally to head and neck squamous cell carcinomas (HNSCCs) related to human papillomavirus subtype 16 (HPV16) infections. More particularly, the present disclosure provides novel immunogenic epitopes from HPV16 E2, E6 and E7 antigens restricted by common human leukocyte antigen (HLA) alleles for the diagnosis and treatment of HNSCC. The HPV16 epitopes identified in the present disclosure can be used in combination with blockade of HPV16+ HNSCC-specific checkpoints for targeted immunotherapy.

6 Claims, 35 Drawing Sheets

Specification includes a Sequence Listing.

(56) References Cited

OTHER PUBLICATIONS

Bartkowiak et al. Unique potential of 4-1 BB agonist antibody to promote durable regression of HPV+ tumors when combined with an E6/E7 peptide vaccine. Proc Natl Acad Sci U S A . Sep. 22, 2015;112(38):E5290-9.*
Robert C, et al. (2015) Pembrolizumab versus Ipilimumab in Advanced Melanoma. N Engl J Med 372(26):2521-2532.
Rooney MS, Shukla SA, Wu CJ, Getz G, Hacohen N (2015) Molecular and genetic properties of tumors associated with local immune cytolytic activity Cell 160(1-2):48-61.
Rosenblatt J, et al. (2016) Individualized vaccination of AML patients in remission is associated with induction of antileukemia immunity and prolonged remissions. Sci Transl Med 8(368):368ra171.
Rudolf MP, Man S, Melief CJ, Sette A, Kast WM (2001) Human T-cell responses to HLA-A-restricted high binding affinity peptides of human papillomavirus type 18 proteins E6 and E7. Clin Cancer Res 7(3 Suppl):788s-795s.
Rusan M, Li YY, Hammerman PS (2015) Genomic landscape of human papillomavirus-associated cancers. Clin Dancer Res 21(9):2009-2019.
Schumacher TN, Schreiber RD (2015) Neoantigens in cancer immunotherapy. Science 348(6230):69-74.
Şenbabaoğlu Y, et al. (2016) Tumor immune microenvironment characterization in clear cell renal cell carcinoma identifies prognostic and immunotherapeutically relevant messenger RNA signatures. Genome Biol 17(1):231.
Zhang Y, et al. (2016) Subtypes of HPV-Positive Head and Neck Cancers Are Associated with HPV Characteristics, Copy Number Alterations, PIK3CA Mutation, and Pathway Signatures Clin Cancer Res 22(18):4735-4745.
Sheridan C (2015) IDO inhibitors move center stage in immuno-oncology. Nat Biotechnol 33(4):321-322.
Spranger S, et al. (2013) Up-Regulation of PD-L1, IDO, and Tregs in the Melanoma Tumor Microenvironment Is Driven by CD8 T Cells Sci Transl Med 5(200):200ra116-200ra116.
Tenzer S, et al. (2005) Modeling the MHC class I pathway by combining predictions of proteasomal cleavage, TAP transport and MHC class I binding. Cell Mol Life Sci 62(9):1025-1037.
Zhang GL, et al. (2014) HPVdb: a data mining system for knowledge discovery in human papillomavirus with applications in T cell immunology and vaccinology. Database 2014(0):bau031-bau031.
Torre LA, et al. (2015) Global cancer statistics, 2012. CA Cancer J Clin 65(2):87-108.
Tran E, et al. (2016) T-Cell Transfer Therapy Targeting Mutant KRAS in Cancer. N Engl J Med 375(23):2255-2262.
Trimble CL, et al. (2015) Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial. Lancet 386(10008):2078-2088.
U.S. Appl. No. 17/232,631, filed Apr. 21, 2021, Lindsay et al.
Wherry EJ, John Wherry E, Kurachi M (2015) Molecular and cellular insights into T cell exhaustion. Nat Rev Immunol 15(8):486-499.
Williams WW, et al. (2017) Surveillance of Vaccination Coverage among Adult Populations—United States, 2015. MMWR Surveill Summ 66(11):1-28.
Woodman CBJ, Collins SI, Young LS (2007) The natural history of cervical HPV infection: unresolved issues. Nat Rev Cancer 7(1):11-22.
Akagi K, et al. (2014) Genome-wide analysis of HPV integration in human cancers reveals recurrent, focal genomic instability. Genome Res 24(2):185-199.
Anderson KS, et al. (2015) HPV16 antibodies as risk factors for oropharyngeal cancer and their association with tumor HPV and smoking status. Oral Oncol 51(7):662-667.
Badoual C, et al. (2013) PD-1-expressing tumor-infiltrating T cells are a favorable prognostic biomarker in HPV-associated head and neck cancer. Cancer Res 73(1):128-138.
Barber DL, et al. (2006) Restoring function in exhausted CD8 T cells during chronic viral infection. Nature 439 (7077):682-687.
Campo MS, et al. (2010) HPV-16 E5 down-regulates expression of surface HLA class I and reduces recognition by CD8 T cells. Virology 407(1):137-142.
Cancer Genome Atlas Network (2015) Comprehensive genomic characterization of head and neck squamous cell carcinomas. Nature 517(7536):576-582.
Cerami E, et al. (2012) The eBio cancer genomics portal: an open platform for exploring multidimensional cancer genomics data. Cancer Discov 2(5):401-404.
Chaturvedi AK, et al. (2013) Worldwide trends in incidence rates for oral cavity and oropharyngeal cancers. J Clin Oncol 31(36):4550-4559.
Chow LQM, et al. (2016) Antitumor Activity of Pembrolizumab in Biomarker-Unselected Patients With Recurrent and/or Metastatic Head and Neck Squamous Cell Carcinoma: Results From the Phase Ib KEYNOTE-012 Expansion Cohort. J Clin Oncol. doi:10.1200/JCO.2016.68.1478.
Chowell D, et al. (2015) TCR contact residue hydrophobicity is a hallmark of immunogenic CD8+ T cell epitopes. Proc Natl Acad Sci U S A 112(14):E1754-62.
D'Souza G, et al. (2007) Case-Control Study of Human Papillomavirus and Oropharyngeal Cancer. N Engl J Med 356 (19):1944-1956.
Dahlstrom KR, Anderson KS, Sturgis EM (2017) Human Papillomavirus-Associated Oropharyngeal Cancer. JAMA Oncology 3(2):161.
De Simone M, et al. (2016) Transcriptional Landscape of Human Tissue Lymphocytes Unveils Uniqueness of Tumor-Infiltrating T Regulatory Cells. Immunity 45(5):1135-1147.
Draper LM, et al. (2015) Targeting of HPV-16+ Epithelial Cancer Cells by TCR Gene Engineered T Cells Directed against E6. Clin Cancer Res 21(19):4431-4439.
Dunne EF, et al. (2014) CDC grand rounds: Reducing the burden of HPV-associated cancer and disease. MMWR Morb Mortal Wkly Rep 63(4):69-72.
Economopoulou, P. et al., "The emerging role of immunotherapy in head and neck squamous cell carcinoma (HNSCC): anti-tumor immunity and clinical application", Annals of Translational Medicine, May 2016, vol. 4, No. 9, article 173, 13 pages <DOI:10.21037/atm.2016.03.34>.
Ellis JR, et al. (1995) The association of an HPV16 oncogene variant with HLA-B7 has implications for vaccine design in cervical cancer. Nat Med 1(5):464-470.
Ferris RL, et al. (2016) Nivolumab for Recurrent Squamous-Cell Carcinoma of the Head and Neck. N Engl J Med 375 (19):1856-1867.
Gangadhar TC, et al. (2015) Preliminary results from a Phase I/II study of epacadostat (incb024360) in combination with pembrolizumab in patients with selected advanced cancers. Journal for ImmunoTherapy of Cancer 3(Suppl 2):O7.
Gillison ML, Chaturvedi AK, Anderson WF, Fakhry C (2015) Epidemiology of Human Papillomavirus-Positive Head and Neck Squamous Cell Carcinoma J Clin Oncol 33(29):3235-3242.
Gillison ML, et al. (2012) Prevalence of Oral HPV Infection in the United States, 2009-2010. JAMA 307(7):693.
González-Galarza FF, et al. (2015) Allele frequency net 2015 update: new features for HLA epitopes, KIR and disease and HLA adverse drug reaction associations. Nucleic Acids Res 43(Database issue):D784-8.
Gupta PK, et al. (2015) CD39 Expression Identifies Terminally Exhausted CD8+ T Cells. PLoS Pathog 11(10):e1005177.
Herbst RS, et al. (2014) Predictive correlates of response to the anti-PD-L1 antibody MPDL3280A in cancer patients. Nature 515(7528):563-567.
Hoof I, et al. (2009) NetMHCpan, a method for MHC class I binding prediction beyond humans. Immunogenetics 61(1):1-13.
International Preliminary Report on Patentability for Application No. PCT/US2018/061362 dated May 28, 2020 (9 pages).

(56) References Cited

OTHER PUBLICATIONS

International Search Report and Written Opinion for Application No. PCT/US2018/061362 dated Apr. 22, 2019 (16 pages).
Jemal A, et al. (2013) Annual Report to the Nation on the Status of Cancer, 1975-2009, Featuring the Burden and Trends in Human Papillomavirus (HPV)-Associated Cancers and HPV Vaccination Coverage Levels. JNCI: Journal of the National Cancer Institute 105(3):175-201.
Johnston RJ, et al. (2014) The immunoreceptor TIGIT regulates antitumor and antiviral CD8(+) T cell effector function. Cancer Cell 26(6):923-937.
Kenter GG, et al. (2009) Vaccination against HPV-16 oncoproteins for vulvar intraepithelial neoplasia. N Engl J Med 361(19):1838-1847.
Krishna S, Anderson KS (2016) T-Cell Epitope Discovery for Therapeutic Cancer Vaccines. Methods Mol Biol 1403:779-796.
Krishna, S et al., "Abstract 4559: Novel T-cell targets for HPV16-associated oropharyngeal cancer immune therapy", Cancer Research, AACR Annual Meeting Apr. 1-5, 2017, Jul. 2017, vol. 77, No. 13, abstract No. 4559 <DOI:10.1158/1538-7445.AM2017-4559>.
Lund O, et al. (2004) Definition of supertypes for HLA molecules using clustering of specificity matrices. Immunogenetics 55(12):797-810.
Mandal R, et al. (2016) The head and neck cancer immune landscape and its immunotherapeutic implications. JCI Insight 1(17):e89829.
Marur S, D'Souza G, Westra WH, Forastiere AA (2010) HPV-associated head and neck cancer: a virus-related cancer epidemic. Lancet Oncol 11(8):781-789.
Moutaftsi M, et al. (2006) A consensus epitope prediction approach identifies the breadth of murine TCD8-cell responses to vaccinia virus. Nat Biotechnol 24(7):817-819.
Mueller SN, Ahmed R (2009) High antigen levels are the cause of T cell exhaustion during chronic viral infection. Proc Natl Acad Sci U S A 106(21):8623-8628.
Olthof NC, et al. (2014) Comprehensive analysis of HPV16 integration in OSCC reveals no significant impact of physical status on viral oncogene and virally disrupted human gene expression PLoS One 9(2):e88718.

Olthof NC, et al. (2015) Viral load, gene expression and mapping of viral integration sites in HPV16-associated HNSCC cell lines. Int J Cancer 136(5):E207-18.
Ott PA, et al. (2017) An immunogenic personal neoantigen vaccine for patients with melanoma. Nature 547 (7662):217-221.
Pardoll DM (2012) The blockade of immune checkpoints in cancer immunotherapy. Nat Rev Cancer 12(4):252-264.
Parfenov M, et al. (2014) Characterization of HPV and host genome interactions in primary head and neck cancers. Proc Natl Acad Sci U S A 111(43):15544-15549.
Parikh F, et al. (2014) Chemoradiotherapy-induced upregulation of PD-1 antagonizes immunity to HPV-related propharyngeal cancer. Cancer Res 74(24):7205-7216.
Petrovic D, Dempsey E, Doherty DG, Kelleher D, Long A (2012) Hepatitis C virus—T-cell responses and viral escape mutations. Eur J Immunol 42(1):17-26.
Price DA, et al. (1997) Positive selection of HIV-1 cytotoxic T lymphocyte escape variants during primary infection. Proc Natl Acad Sci U S A 94(5):1890-1895.
Rammensee H-G, et al. (1999) SYFPEITHI: database for MHC ligands and peptide motifs. Immunogenetics 50 (3-4):213-219.
Ramos, C. et al., "Human Papillomavirus Type 16 E6/E7-Specific Cytotoxic T Lymphocytes for Adoptive Immunotherapy of HPV-Associated Malignancies", preprint, final form published in Journal of Immunotherapy, Jan. 2013, vol. 36, No. 1, pp. 66-76 <DOI:10.1097/CJI.0b013e318279652e>.
Ressing ME, et al. (1995) Human CTL epitopes encoded by human papillomavirus type 16 E6 and E7 identified through in vivo and in vitro immunogenicity studies of HLA-A*0201-binding peptides. J Immunol 154(11):5934-5943.
Riemer AB, et al. (2010) A conserved E7-derived cytotoxic T lymphocyte epitope expressed on human papillomavirus 16-transformed HLA-A2+ epithelial cancers. J Biol Chem 285(38):29608-29622.
Rizvi NA, et al. (2015) Cancer immunology. Mutational landscape determines sensitivity to PD-1 blockade in non-small cell lung cancer. Science 348(6230):124-128.

\* cited by examiner

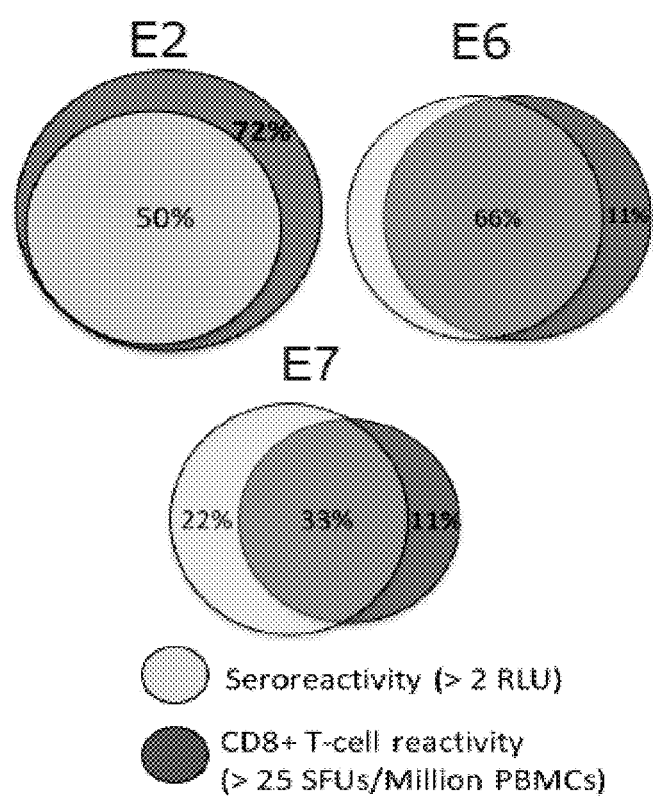

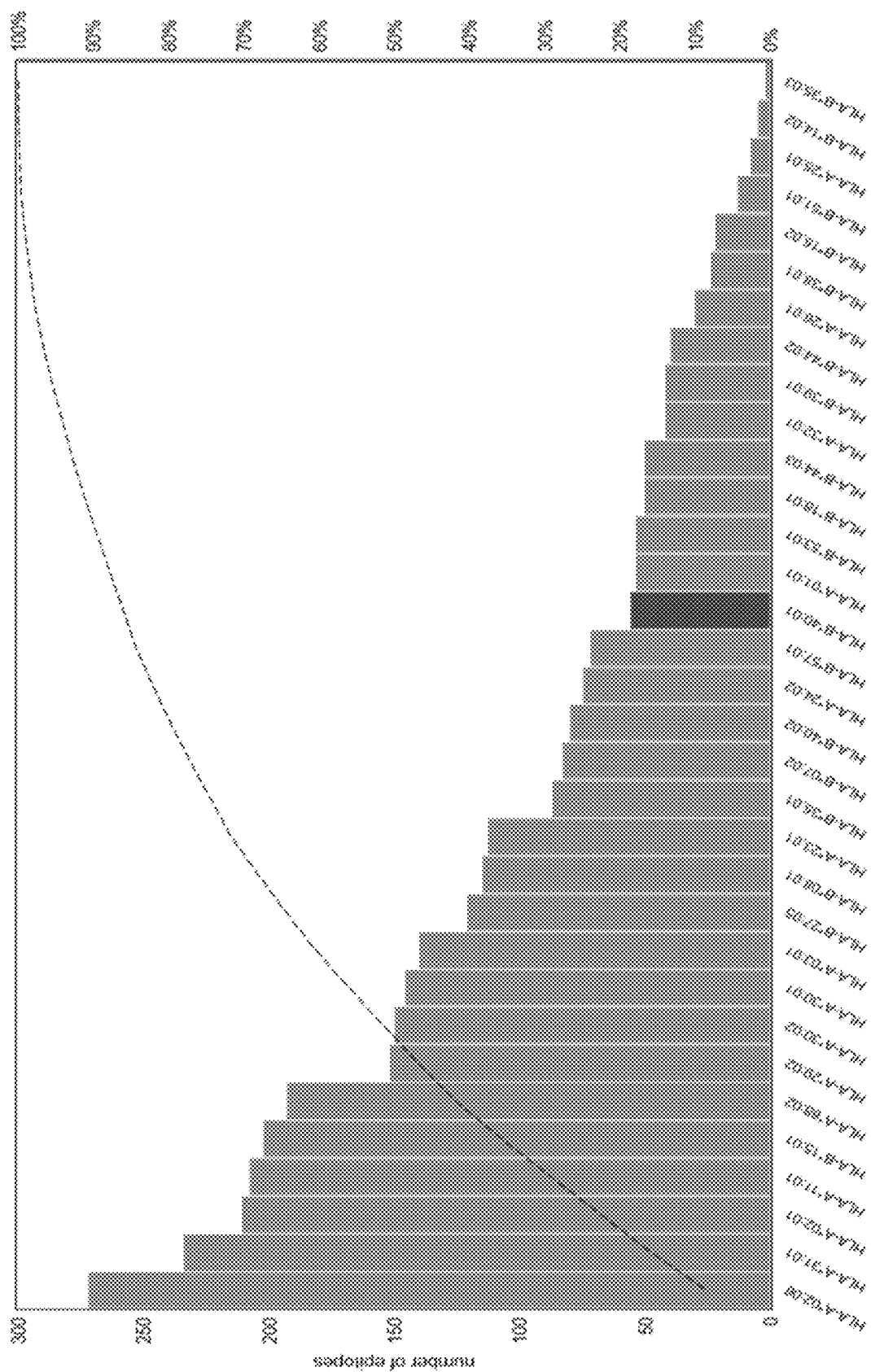

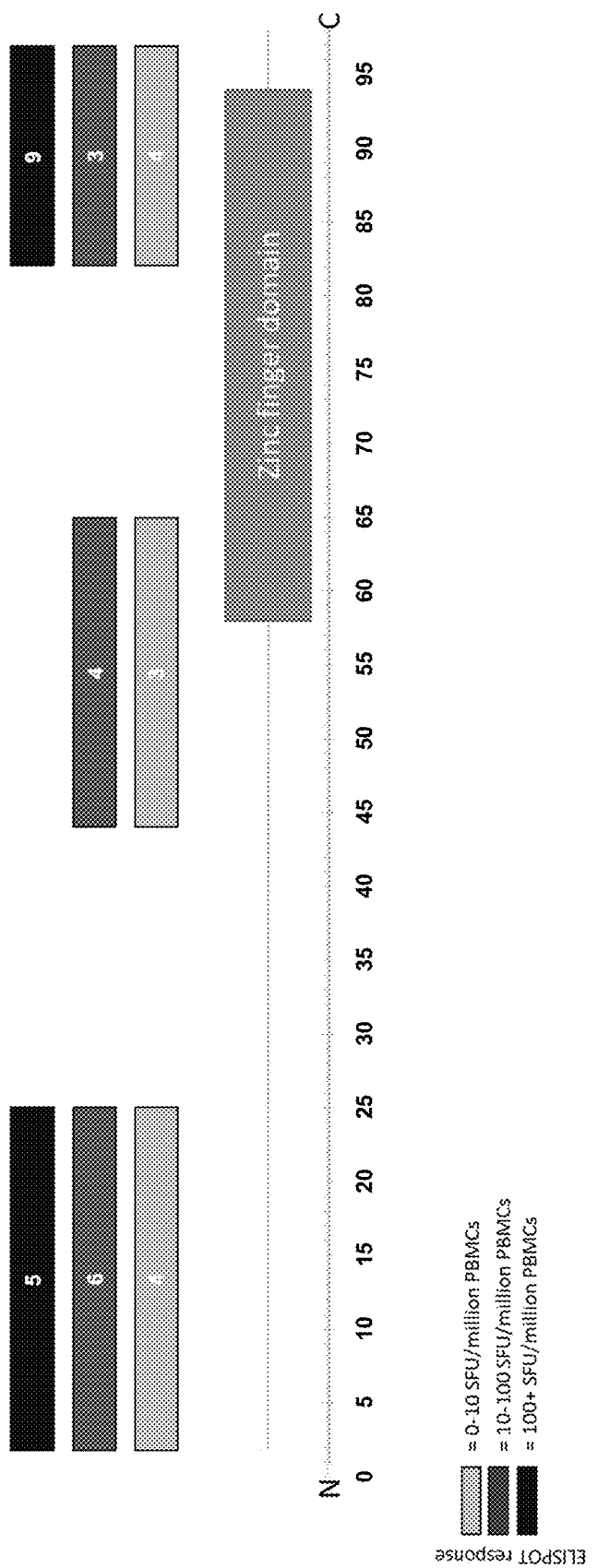

MATERIALS AND METHODS RELATING TO IMMUNOGENIC EPITOPES FROM HUMAN PAPILLOMAVIRUS

CROSS-REFERENCE TO RELATED APPLICATIONS

This application claims the benefit of U.S. Provisional Patent Application No. 62/586,517, filed on Nov. 15, 2017, the entire content of which is fully incorporated herein by reference.

SEQUENCE LISTING

The present specification makes reference to a Sequence Listing (submitted electronically as a .txt file named "208192-9044_ST25.txt." The .txt file was generated on Nov. 13, 2018 and is 10,491 bytes in size. The entire contents of the Sequence Listing are hereby incorporated by reference.

TECHNICAL FIELD

Embodiments of the present disclosure pertain generally to cancers associated with human papillomavirus subtype 16 (HPV16) infections. More particularly, the present disclosure provides novel immunogenic epitopes from HPV16 E2, E6 and E7 antigens restricted by common human leukocyte antigen (HLA) alleles for the diagnosis and treatment of HPV16-associated cancers.

BACKGROUND

Head and neck squamous cell carcinoma (HNSCC) is the sixth most common cancer worldwide with close to 600,000 cases diagnosed annually. A subset of HNSCCs caused by the human papillomavirus (HPV), (HPV+ HNSCCs), are molecularly and clinically distinct from non-HPV associated HNSCCs (HPV− HNSCCs). In the United States, 70-80% of HPV+ HNSCCs are caused by the oncogenic HPV type 16 (HPV16). Incidence of HPV+ HNSCC increased 225% from 1984-2004 and has now surpassed the incidence of cervical cancer. Although HPV vaccines effectively prevent HPV-related cancers, the impact of vaccination on HNSCC incidence may not occur until 2060, likely due in part to slow vaccine uptake, and the decades between infection and clinical HPV+ HNSCC diagnosis. As a result, over 600,000 cases are predicted in the interim, providing a strong rationale for the development of novel therapeutic strategies against HPV+ HNSCC.

The recent development of clinically effective tumor immunotherapies, such as checkpoint blockade (CKB) using PD-1/PD-L1 inhibitors, has led to FDA approval of nivolumab and pembrolizumab for HNSCC. It is now established that the clinical response to CKB is correlated with tumor neo-epitope load. Tumor-specific neo-epitopes have been directly targeted using therapeutic vaccines and/or adoptive T-cell therapy (ACT), and have been shown to enhance cytotoxic T-cell targeting of multiple solid tumors. Thus, there is a renewed interest in defining the human leukocyte antigen (HLA) restricted antigenic repertoire of tumor infiltrating lymphocytes (TILs) to develop targeted therapeutic vaccines, to identify T-cell receptors (TCR) for ACT, and to monitor clinical responses to complex cancer immunotherapies.

SUMMARY

Embodiments of the present disclosure pertain generally to cancers associated with human papillomavirus subtype 16 (HPV16) infections. More particularly, the present disclosure provides novel immunogenic epitopes from HPV16 E2, E6 and E7 antigens restricted by common human leukocyte antigen (HLA) alleles for the diagnosis and treatment of HPV16-associated cancers.

Embodiments of the present disclosure include an immunogenic composition for treating a subject having a HPV16-associated disease. In accordance with these embodiments the composition includes a synthetic polypeptide encoding a cytotoxic T lymphocyte (CTL) epitope derived from E2, E6, or E7 human papillomavirus subtype 16 (HPV16) antigens and a pharmaceutically acceptable carrier or excipient. In some embodiments, the immunogenic composition is for treating a subject with head and neck squamous cell carcinoma (HNSCC).

Embodiments of the present disclosure include a method of treating a subject having a HPV16-associated disease. In accordance with these embodiments, the method comprises administering an immunogenic composition described above wherein the administration of the composition induces an immune response against the HPV16-associated disease and treats the subject. In some embodiments the method is used to treat a subject with head and neck squamous cell carcinoma (HNSCC). In some embodiments, the immunogenic composition includes an immune checkpoint inhibitor which can include a programmed cell death protein 1 (PD-1) and an Indoleamine 2,3-dioxygenase 1 (IDO-1) inhibitor.

Embodiments of the present disclosure include an immune cell comprising a T-cell receptor (TCR) capable of binding a synthetic polypeptide encoding a cytotoxic T lymphocyte (CTL) epitope derived from E2, E6, or E7 human papillomavirus subtype 16 (HPV16) antigens.

Embodiments of the present disclosure include a method of detecting an HPV16-associated disease in a subject. In accordance with these embodiments, the method includes obtaining a biological sample comprising T cells from a subject, contacting the biological sample with a MHC class I peptide tetramer composition comprising at least one synthetic MHC class I molecule bound to at least one synthetic polypeptide encoding a cytotoxic T lymphocyte (CTL) epitope derived from E2, E6, or E7 human papillomavirus subtype 16 (HPV16) antigens and detecting the presence of T cells bound to the synthetic polypeptide. In some embodiments the detection comprises flow cytometry or fluorescence-activated cell sorting.

BRIEF DESCRIPTION OF THE DRAWINGS

FIGS. 1A-1L include representative analysis of CTL epitopes in HPV+HNSCC from HPV16 E2, E6, and D7 antigens. FIGS. 1A-1B show the distribution and the corresponding odds ratio of each HLA allele in HPV+HNSCC patients based on the median USA HLA allele frequencies (FIG. 1G). The HLA-frequency distribution of the HPV+ HNSCC patients (FIG. 1H) is similar to the median distribution throughout the US (FIG. 1G). The 59 candidate peptides were selected based on binding and total antigen-processing percentile scores (FIGS. 1I-1J). The distribution of all the HPV16-predicted binding peptides per each allele is shown in FIG. 1K. The results for the CTL-reactivity of predicted peptides as determined by IFNγ elispots of PBMCs stimulated for 10 days with candidate peptides and CKB antibodies (FIG. 1L) are shown grouped according to antigen (FIG. 1C) and from one representative HPV+HN-SCC PBMC (FIG. 1D). The correlation between PBMC T-cell reactivity and B-cell immunity (FIGS. 1E-1F) indicates that in HPV+HNSCC patients the E2 and E6 antigens are more CTL-reactive than E7.

FIGS. 2A-2H map the landscape of CTL-epitopes from HPV16 E2, E6, and E7 antigens in HPV+HNSCCs. FIG. 2A shows a summary of an IFN ELISPOT screen for all responding HPV+HNSCC patients against each tested peptide. Representative examples of individual patients are shown in FIGS. 2B-2D. FIG. 2E shows an example of an epitope that elicited a cross-reactive response to other alleles (A11-E2-1 (SEQ ID NO:5), A11-E2-2 (SEQ ID NO:13), A3-E2-2 (SEQ ID NO:12), A11-E6-1 (SEQ ID NO:31), A11-E6-2 (SEQ ID NO:40) and A3-E6-3 (SEQ ID NO:43) within the same supertype. The immunodominant regions of HPV16-E2, E6, and E7 are mapped in FIGS. 2F-2H.

DETAILED DESCRIPTION

Figure 1A:
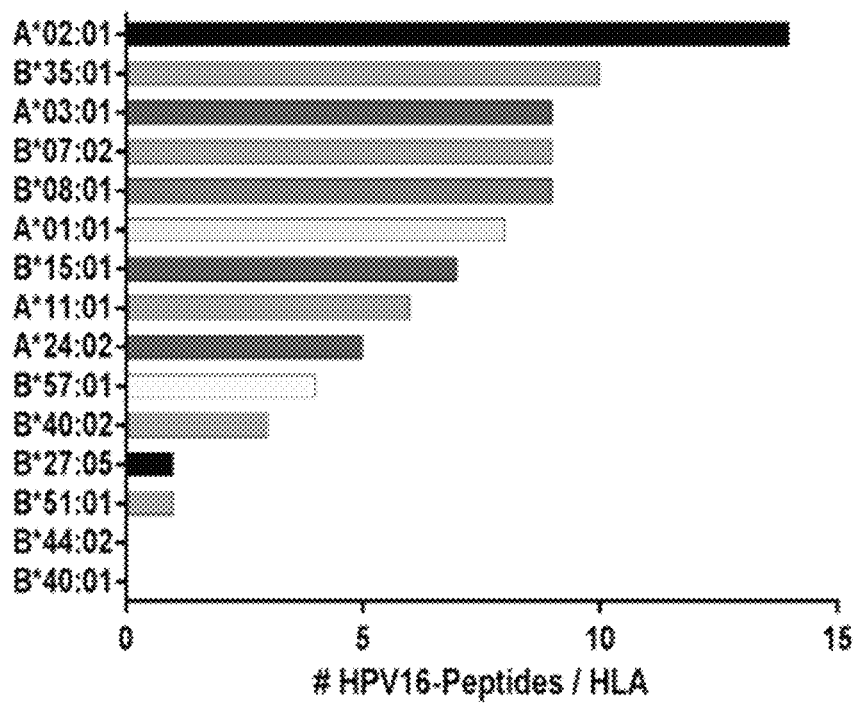

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Polypeptide" and "isolated polypeptide" as used herein refers to a polymer of amino acids or amino acid derivatives that are connected by peptide bonds. An isolated polypeptide is a polypeptide that is isolated from a source. An isolated polypeptide can be at least 1% pure, at least 5% pure, at least 10% pure, at least 20% pure, at least 40% pure, at least 60% pure, at least 80% pure, and at least 90% pure, as determined by one or more protein biochemistry techniques (e.g., SDS-PAGE).

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Treat," "treated," or "treating," as used herein, refer to a therapeutic method wherein the object is to slow down (lessen) an undesired physiological condition, disorder or disease, or to obtain beneficial or desired clinical results. In some aspects of the present disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Before any embodiments of the present disclosure are explained in detail, it is to be understood that the present disclosure is not limited in its application to the details of construction and the arrangement of components set forth in the following description or illustrated in the accompanying drawings. The present disclosure is capable of other embodiments and of being practiced or of being carried out in various ways.

Other aspects of the invention will become apparent by consideration of the detailed description and accompanying drawings.

Embodiments of the present disclosure relate generally to head and neck squamous cell carcinomas (HNSCCs) related to human papillomavirus subtype 16 (HPV16) infections. More particularly, the present disclosure provides novel immunogenic epitopes from HPV16 E2, E6 and E7 antigens restricted by common human leukocyte antigen (HLA) alleles for the diagnosis and treatment of HNSCC. The HPV16 epitopes identified in the present disclosure can be used in combination with blockade of HPV16+HNSCC-specific checkpoints for targeted immunotherapy.

HPV-associated cancers express multiple viral neoantigens. HPV integration into host genome in cervical cancer results in derepression of the oncogenic drivers E6 and E7. Immune therapies targeting E6 and E7 have thus been developed, including peptides, DNA, and ACT therapies. However, in comparison to cervical cancer, HPV+ HNSCCs have both lower rates of genome integration, and less interruption of the viral transcriptional regulatory gene E2. Thus, subsets of HPV+ HNSCCs also express E2 in addition to E6 and E7. It has been shown that high titers of serum antibodies against HPV16-E2, E6 and E7 are detectable in most HPV+ HNSCC patients, indicating immunogenicity and persistence of these antigens. Thus, it is hypothesized that patients with HPV+ HNSCC would have pre-existing HPV-specific CTLs, and that HPV-antigen expression levels would influence CTL-dysregulation in tumor microenvironment. The present disclosure identifies the T-cell antigenic landscape of globally frequent HLA class I alleles from HPV16 E2, E6 and E7. By phenotyping HPV-specific CTLs from HPV+ HNSCC patients, and analyzing the immune transcriptomes of 119 HNSCCs, intratumoral and peripheral CTL-dysfunction in HPV+ HNSCC are demonstrated. Also, CTL-dysfunction can be reversed using targeted HPV-specific T-cell expansion, and synergistic inhibition of IDO-1 and PD-1. Thus, the results of the present disclosure have implications for the development of effective T-cell therapies for HPV+HNSCC.

Strategies enhancing immune-based targeting of tumor cells have come to the forefront of cancer treatments. A subset of head and neck cancers (HNSCCs), caused by HPV16, is an ideal candidate for T-cell cancer immunotherapies. In the present disclosure, immunogenic CD8+ T-cell (CTL) epitopes from 3 HPV16-antigens were identified, and T-cell dysfunction mechanisms in HPV+HNSCC were evaluated. Several novel CTL-epitopes from HPV16-genes E2, E6 and E7 were identified across multiple HLA-alleles in peripheral blood CTLs of HPV+ HNSCC patients. It was also found that tumoral viral load largely drives T-cell infiltration and subsequent CTL-exhaustion observed in HPV+HNSCC. Among other things, the present disclosure demonstrates the usefulness of host immune control of HPV, and identifies combination PD-1/OO-1 inhibition as an efficient and useful strategy to enhance CTL-targeting of HPV+ HNSCC.

HPV-driven malignancies can be a useful model system for cancer immunotherapy, due to 1) a long lead time from infection to malignancy; 2) emerging immune and viral biomarkers for early detection; 3) the persistent tissue expression of viral oncogenes; and 4) epidemiologic evidence of the central role of T-cell control of viral persistence. However, the dynamics of viral persistence within immunocompetent individuals and the mechanisms of tumor immune escape remain largely unknown, in particular for HPV+ HNSCC. The emerging epidemic of HPV+ HNSCC and lack of screening modalities represents a major clinical challenge and opportunity for targeted T-cell immunotherapy.

Embodiments of the present disclosure have expanded the spectrum of HPV+ HNSCC-specific immune therapeutic targets at the CTL-epitope level and at the target tumor cell-modulatory level. Previous studies that have attempted to define CTL-immunogenicity from HPV16 have primarily focused on a limited number of HLA-alleles (e.g., A*02:01) and peptides from E6 and E7 (Tables 1-4), with limited data on immunogenic targets in in HPV+HNSCC. The 15 HLA alleles used in the present disclosure are predicted to include 10/12 of HLA supertypes and over 95% of the global population. Viral immune escape by altering HLA-binding CTL epitopes has been documented in HIV-1 and HCV infections, but not as well for DNA viruses such as HPV, where the mutation rates are markedly lower.

Figure 1B:
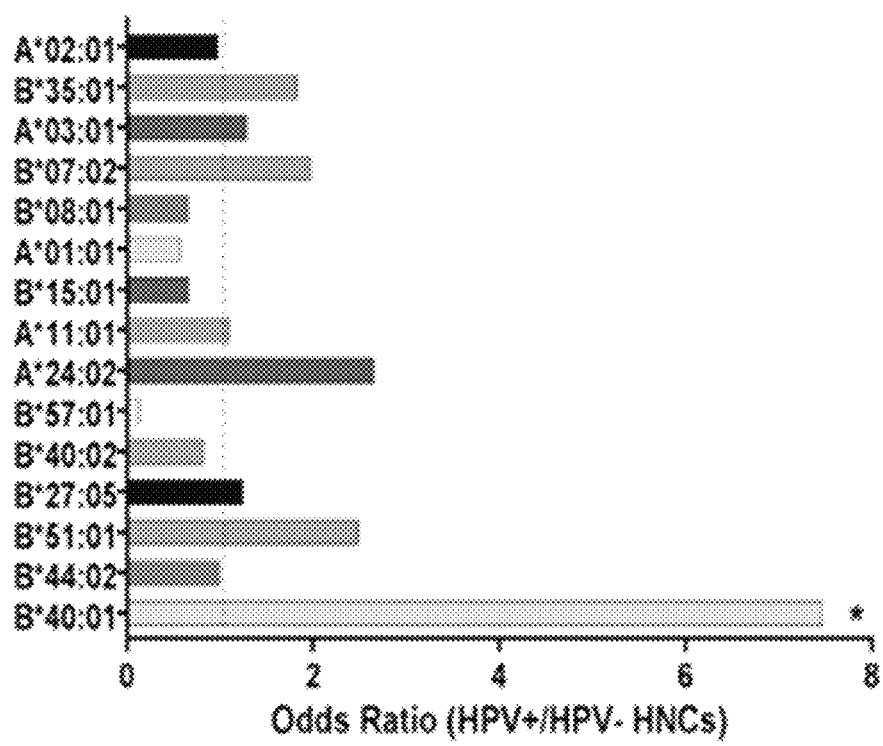
Figure 1C:
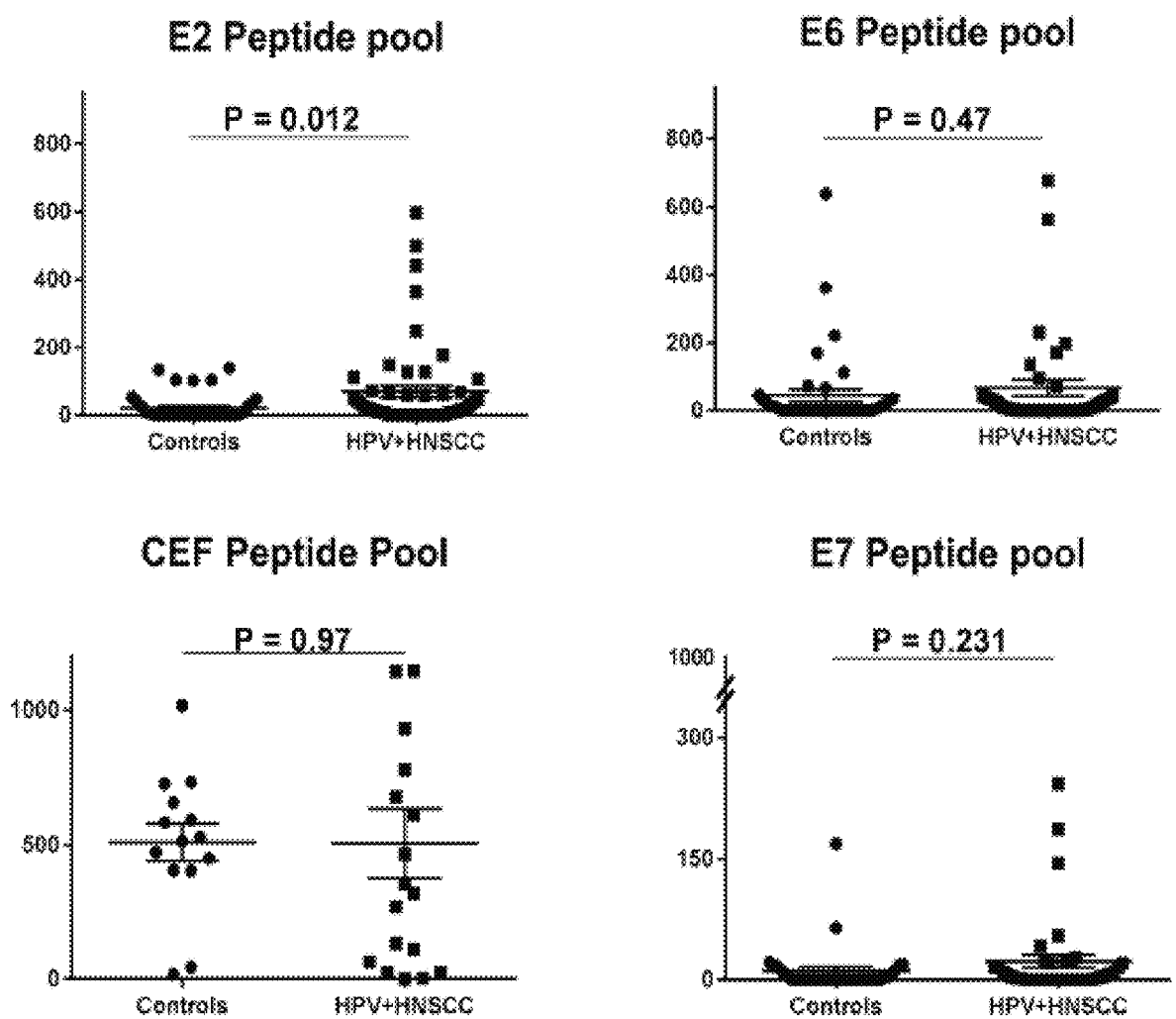
Figure 1D:
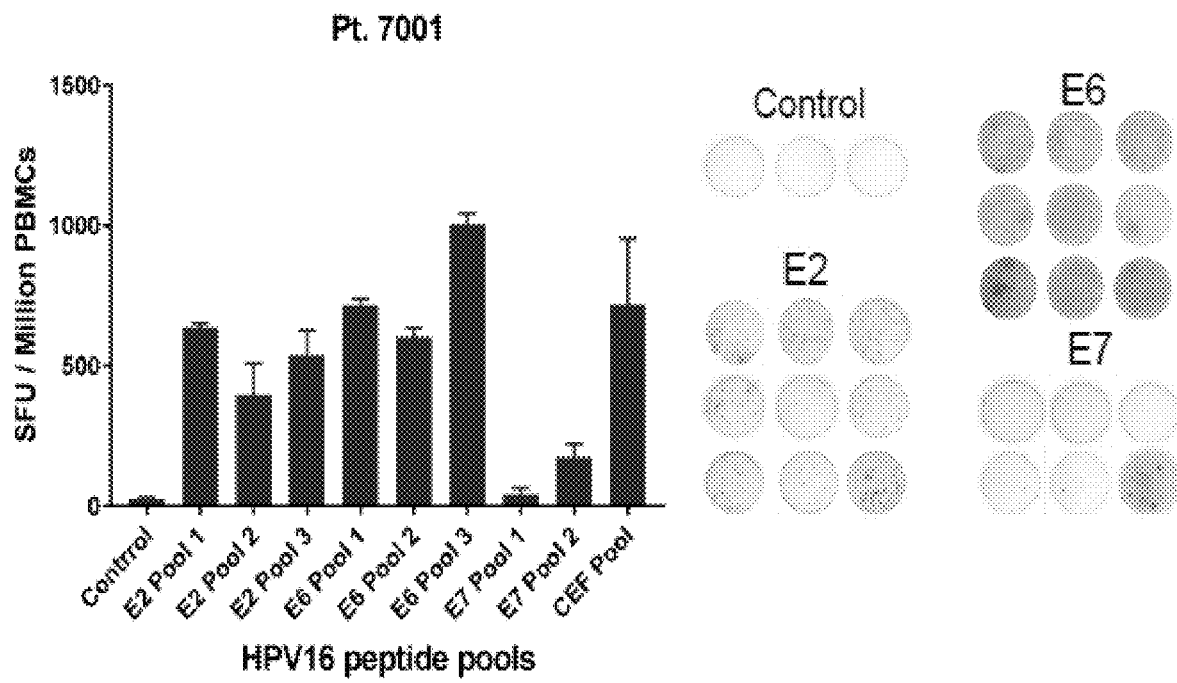

The present disclosure has identified several immunogenic CTL-epitopes from the 3 HPV16-antigens (FIG. 2; Tables 1-4). Addition of PD-1 and CTLA-4 CKB antibodies aided the ability amplify and detect low-frequency HPV-CTL-response in both healthy and HPV+PBMCs ex vivo (FIGS. 1C-1D). These results demonstrate that HPV16-E2 and E6 induce more CTL responses than HPV16-E7 (FIGS. 1 and 2). HPV16-E6 and E7 have been the dominant targets for T-cell based immune therapies against HPV thus far. In contrast, E2-specific CTL-reactivity has been unexplored as an immunotherapeutic target in HPV+ HNSCCs due to the assumption that E2-locus is interrupted by viral integration, similar to that observed in cervical cancer. However, several recent whole genome studies in HNSCCs have indicated that viral breakpoints in HPV+ HNSCCs are distributed throughout the genome, including integration in the E1 region. E2 is also a larger antigen >3-times the size of E6, E7, possibly explaining the bigger spectrum of CTL-epitopes from the protein.

Figure 1E:
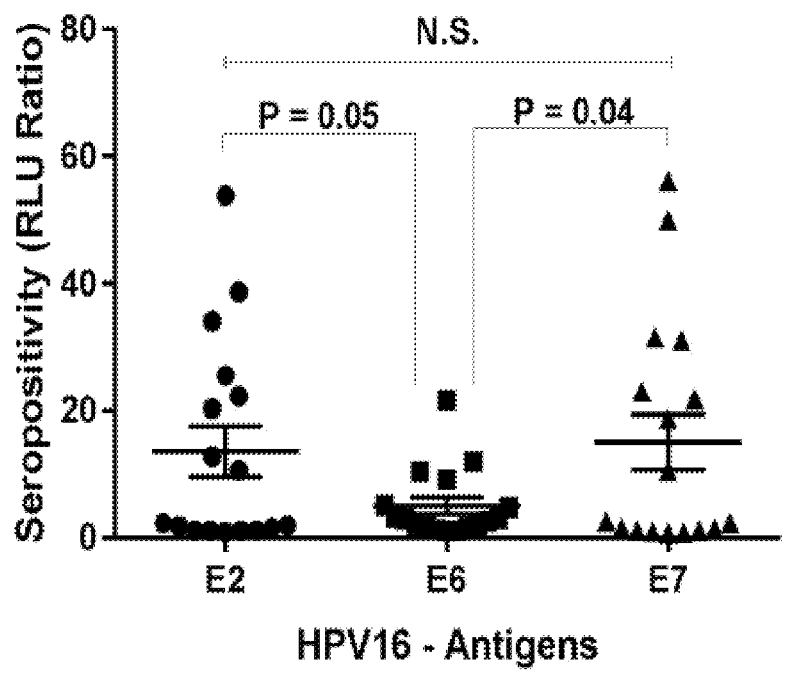
Figure 2A:
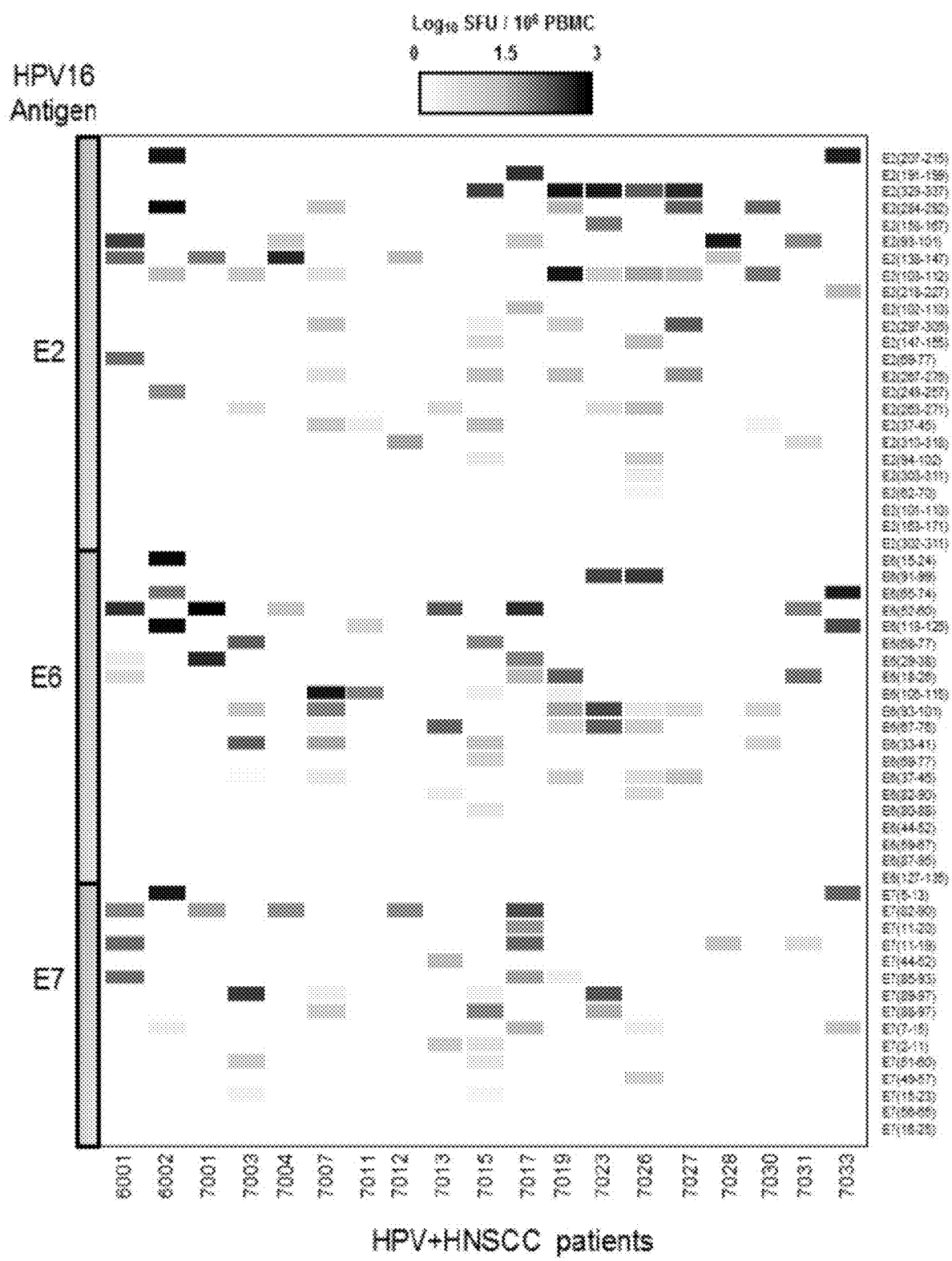
Figure 2B:
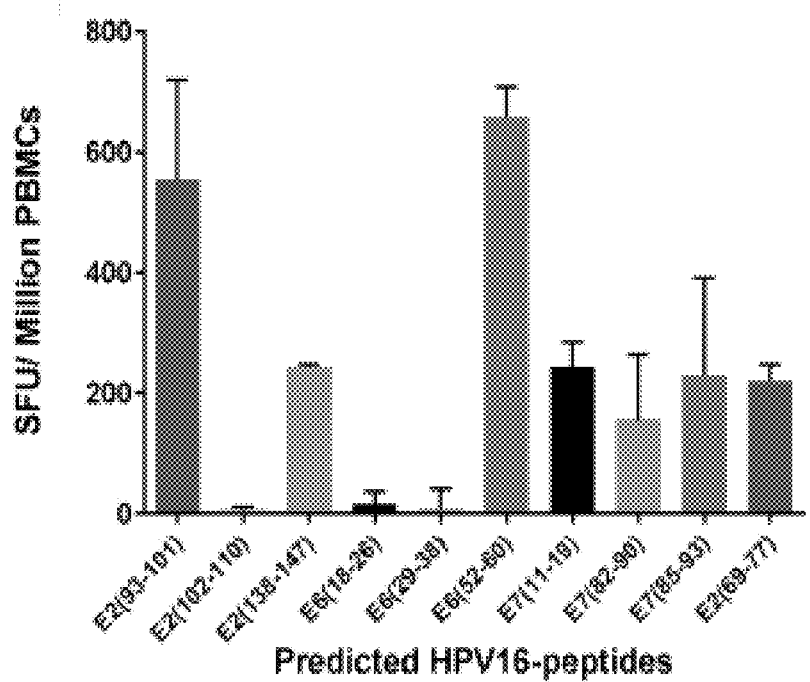
Figure 2C:
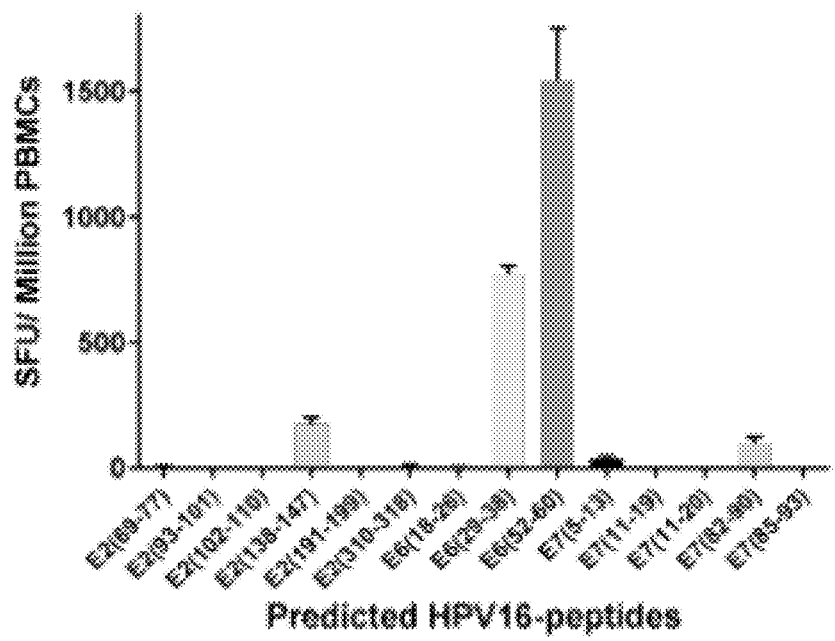
Figure 2D:
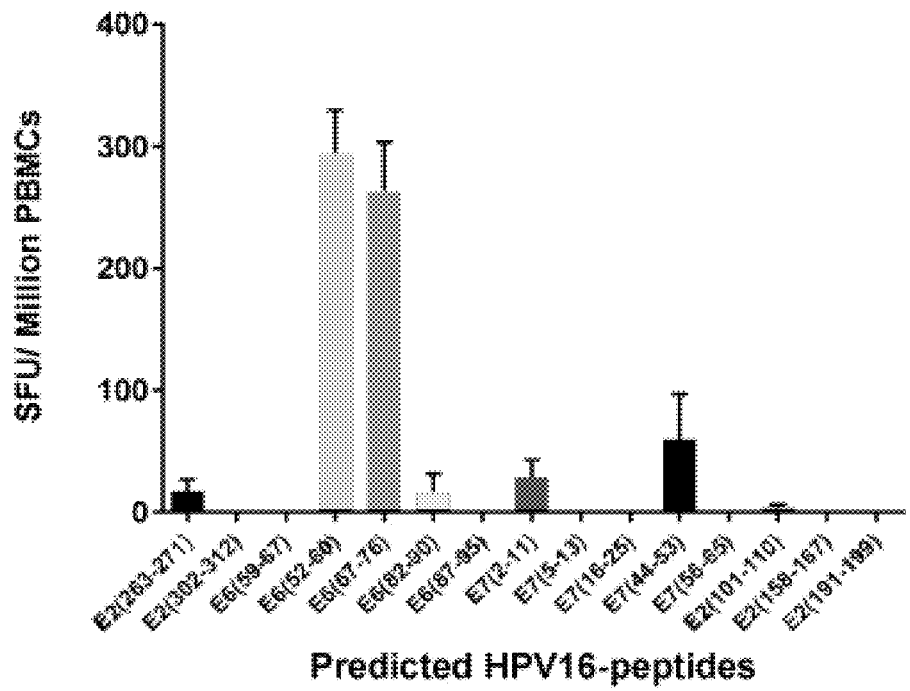
Figure 3A:
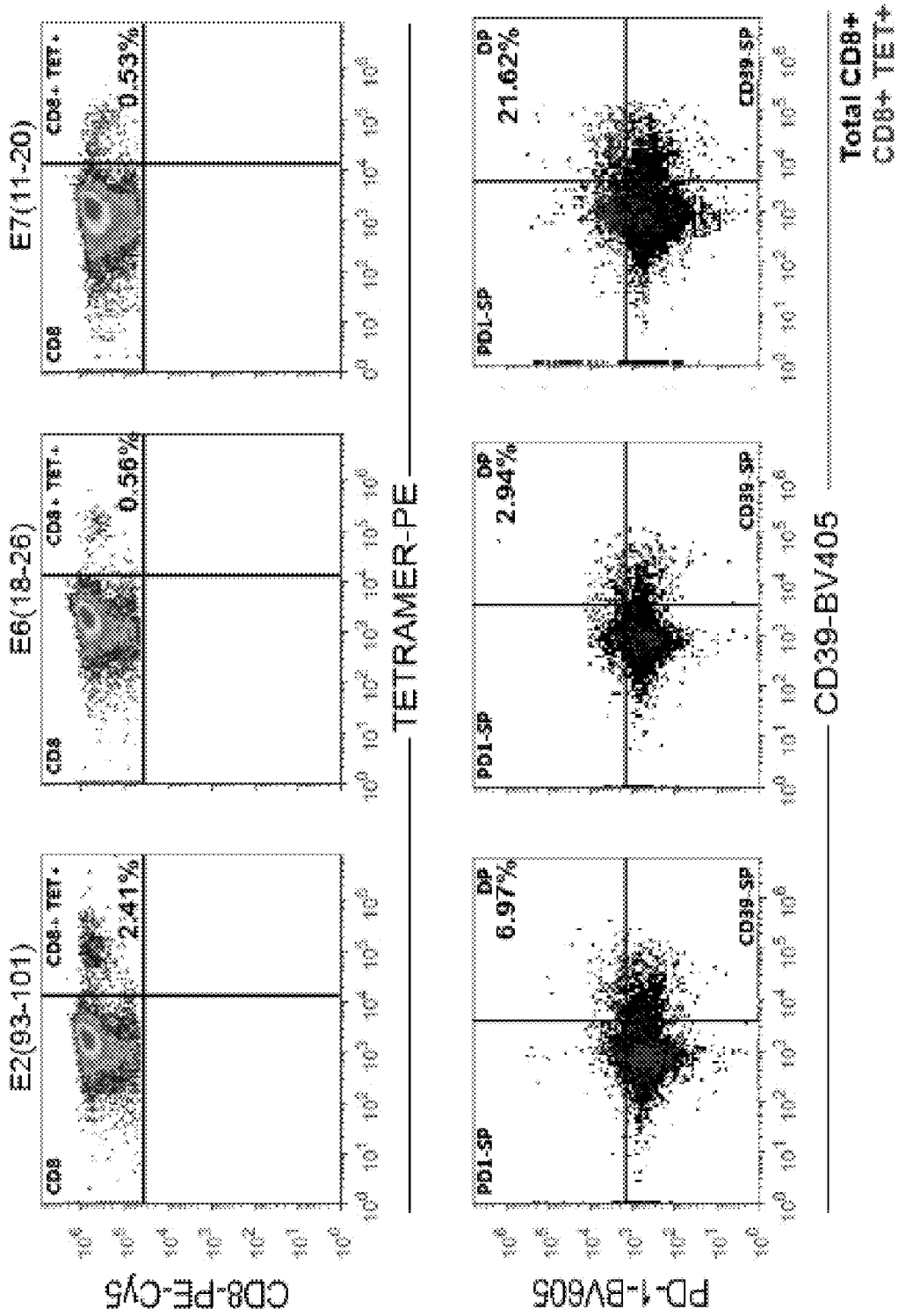
FIGS. 3A-3D show that HPV16-specific T-cells can acquire dysfunctional phenotype in HPV+HNSCC patients. Total and HPV-CTL dysfunction was quantified (FIGS. 3B-3C) using flow cytometry from patients stimulated with transfected APCs for detection of HPV16-Tetramer+ CD8+ Tcells and CD8=PD1+CD39+ or CD8+Tetramer+PD1+ CD39+, as represented in FIG. 3A. Unsupervised hierarchical clustering of the results for all 5 HPV+HNSCC patients (FIG. 3D) indicate that E7-CTL dysfunction is distinct from E2/E6-CTL-dysfunction.
Figure 3B:
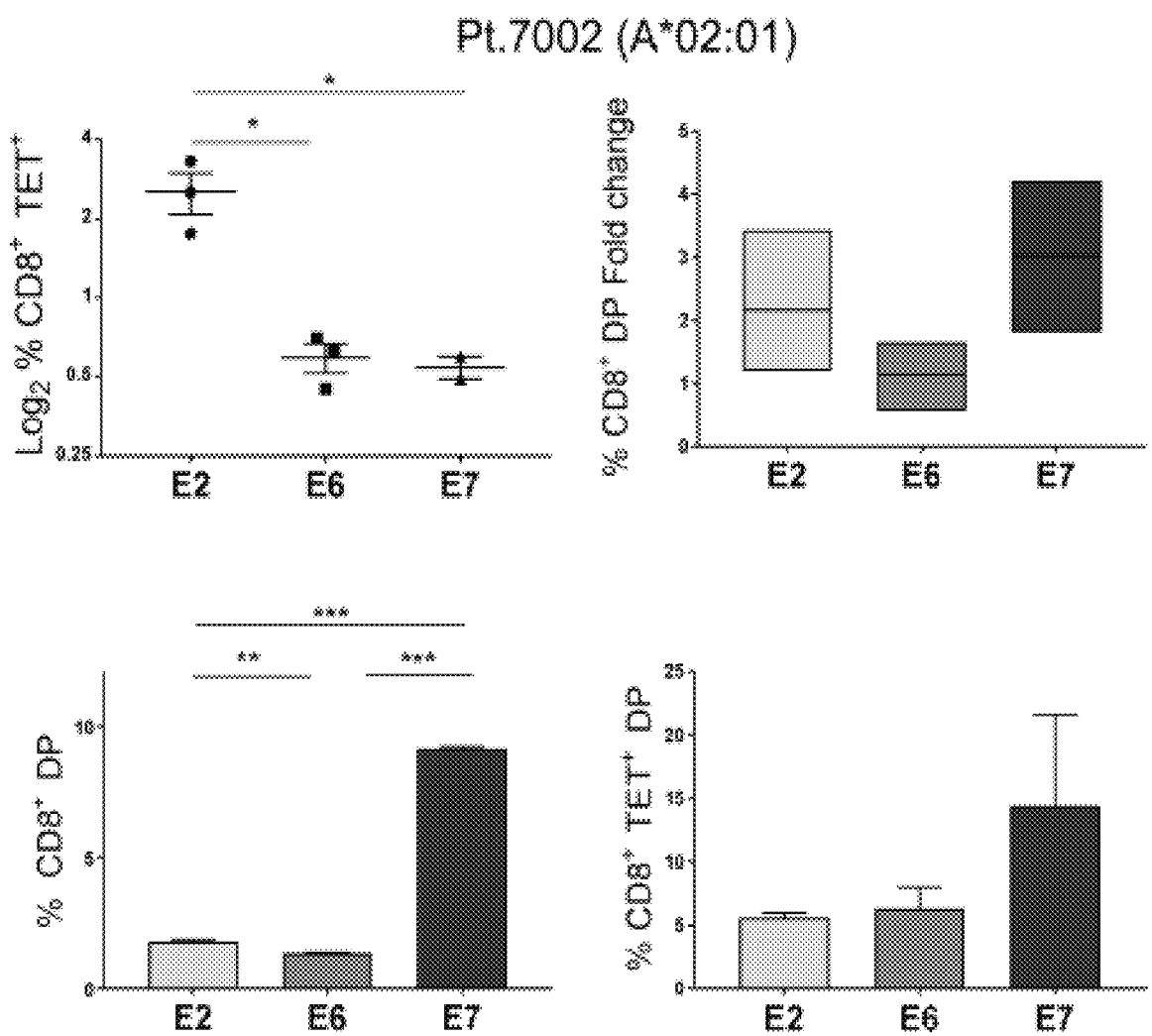
Figure 3C:
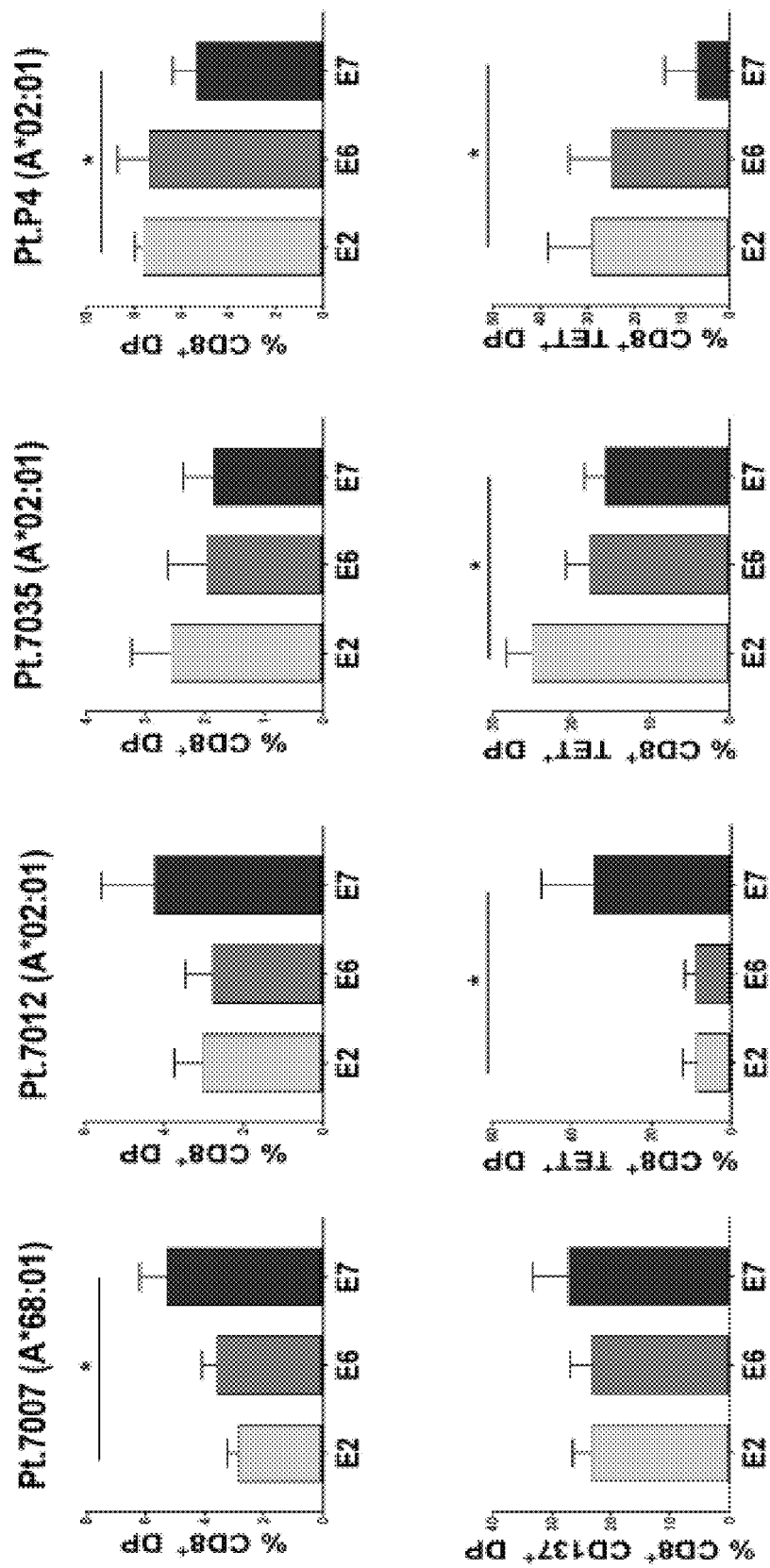
Figure 3D:
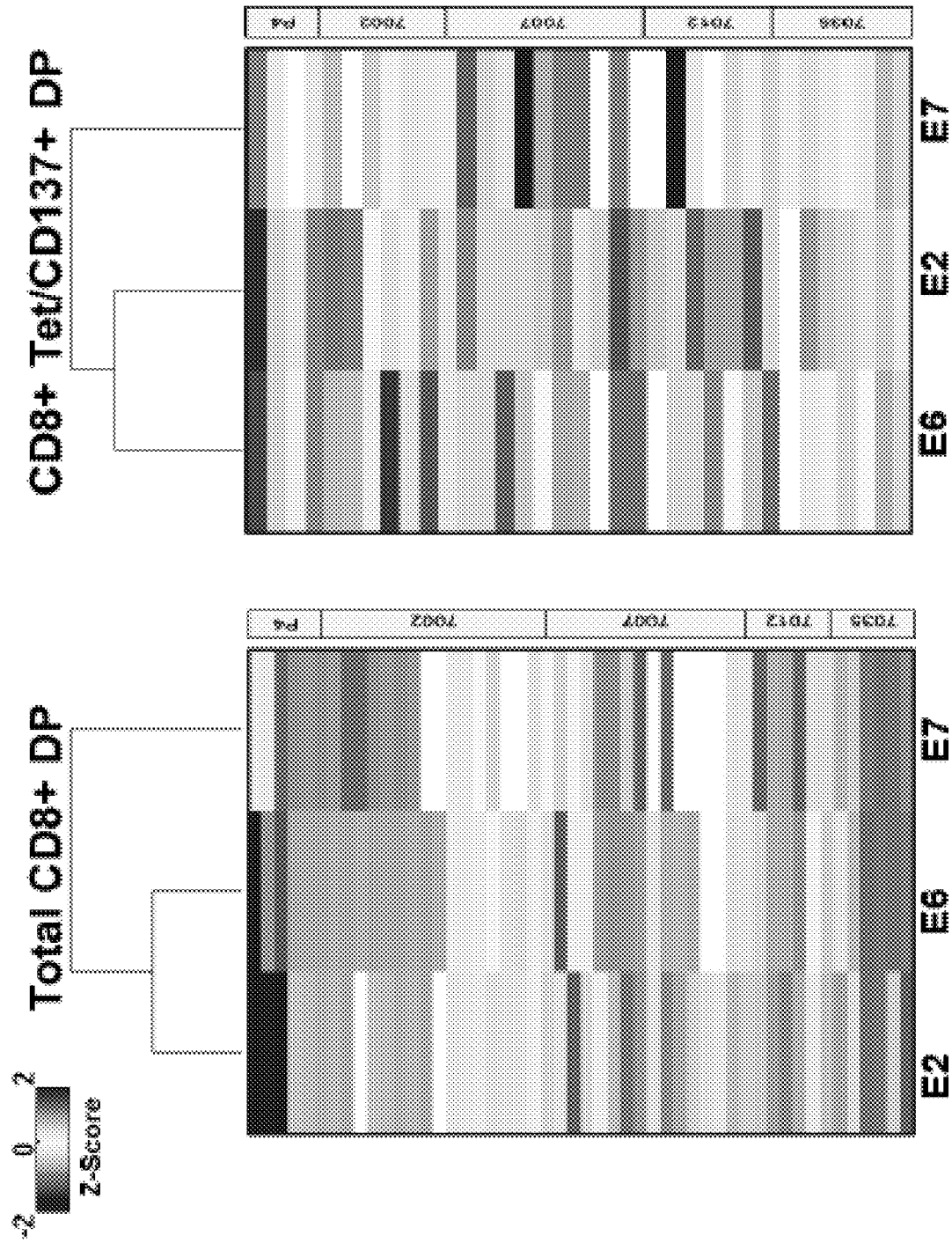

Despite the addition of CKB antibodies in the ex vivo T-cell stimulation protocol, low levels of E7-CTLs were detected compared to E2 and E6-CTLs. However, the prediction of previously described epitopes from E7 and the successful identification of novel CTL-epitopes from E2 and E6 across various HLA-alleles (FIG. 2A), argues against a sub-optimal prediction strategy. The presence of high levels of serum titers against E7 in HPV+ HNSCC patients indicates that the antigen is presented and is immunogenic at least in context of B-cell immunity (FIGS. 1E-1F). Gene expression analysis of HPV+ HNSCC tissue and cell lines showed that E7-antigen load is high in patient tumors, consistent with several other studies. However, E7-CTLs tended to exhibit higher levels of PD1+CD39+ or PD1+TIM3+ DPEx-phenotypes compared to E2 and E6-CTLs after ex vivo stimulation in 3/5 independent HPV+ HNSCC patients (FIG. 3). In particular, E7-CTL dysfunction rarely occurred in concert with E2/E6 CTL dysfunction within the same patient (FIGS. 3B-3D).

While other studies have shown high levels of immune infiltration in HPV+ HNSCCs, results of the present disclosure demonstrate that HPV-antigen load likely drives high CTL-infiltration and CTL-dysfunction (FIG. 4A), arguing for better response to immune CKB therapies. These data thus provide mechanistic insights into this clinical response, wherein, high HPV-antigen load likely drives T-cell infiltration into HPV+ HNSCCs causing immune selection pressure for HPV-CTL dysfunction (in particular E7-CTLs), and that immune checkpoint blockade can at least partially reverse this effect in HPV+ HNSCCs (e.g., ~32% ORR).

Figure 4A:
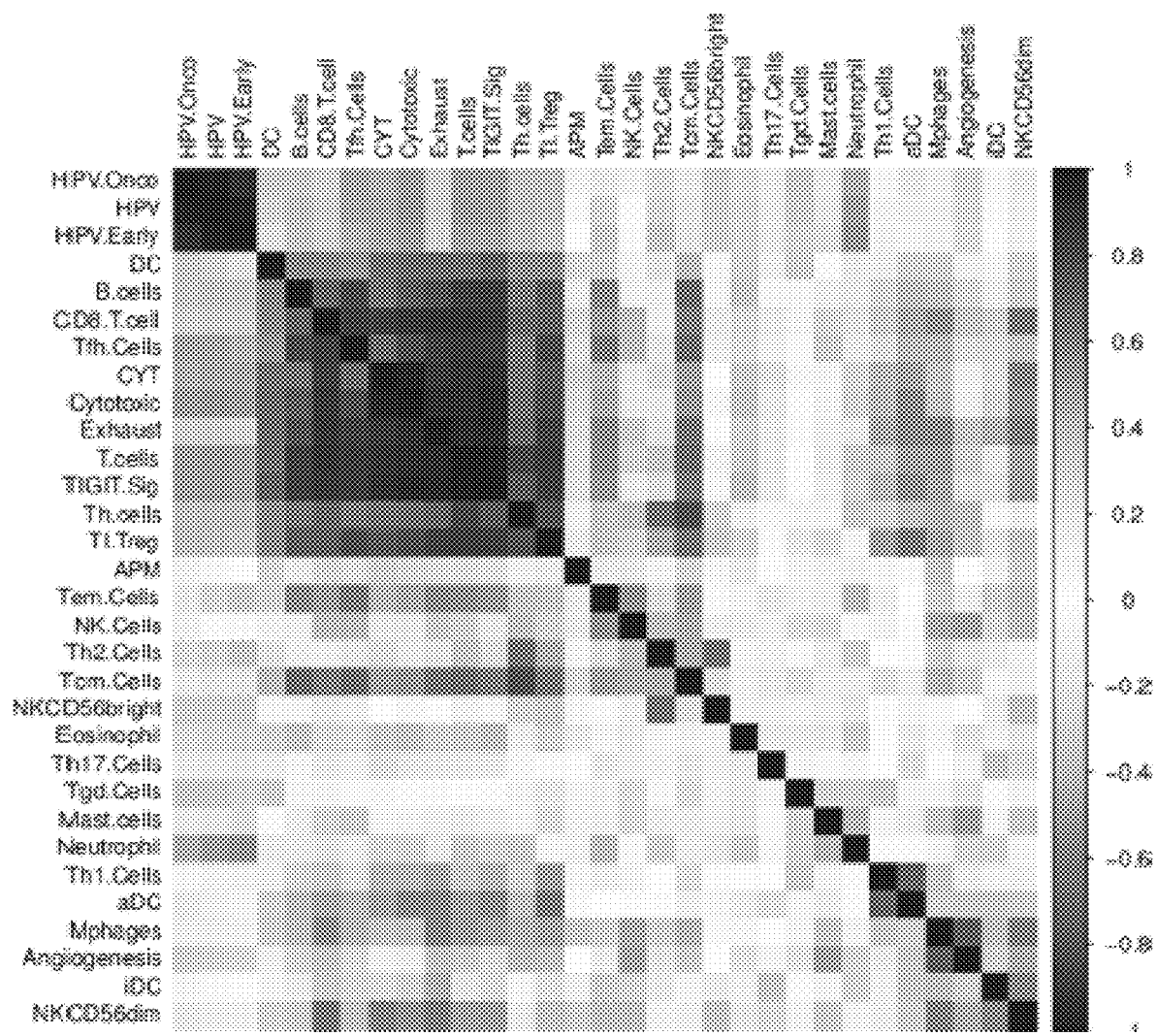
FIGS. 4A-4D demonstrate the correlation between T-cell exhaustion signatures with HPV16-antigen expression. Immunogenic analysis of publicly available HNSCC transcriptomes revealed four clusters in the HPV+ and HPV− subsets (FIG. 4D). An unclustered correlation matrix of the different single-sample gene set enrichment analysis signatures (FIG. 4A) revealed correlation with signatures in distinct modules, including one correlating with a previously described exhaustion gene set (FIG. 4B). The summary of the classification of HPV gene levels in 40 HPV+HNSCC tumors into moderate/low or high exhaustion (FIG. 4C) suggests that HPV-specific CTLs have T-cell exhaustion at tumor sites.
Figure 4B:
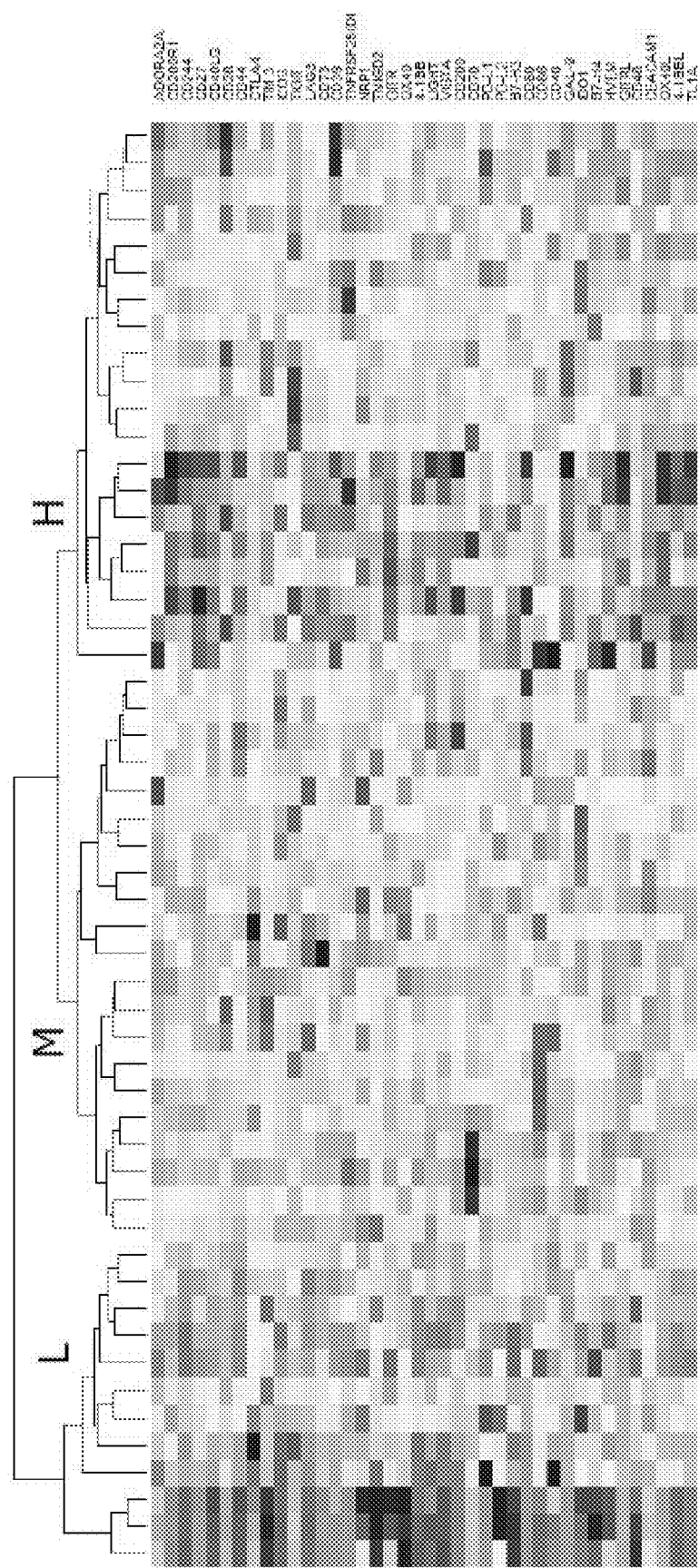
Figure 4C:
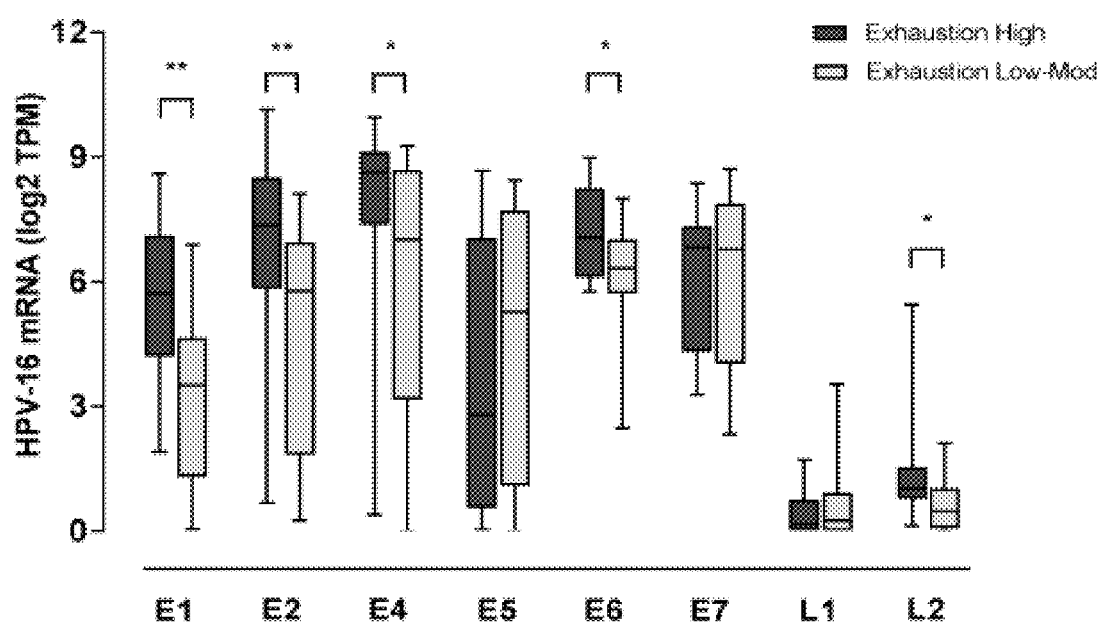
Figure 4D:
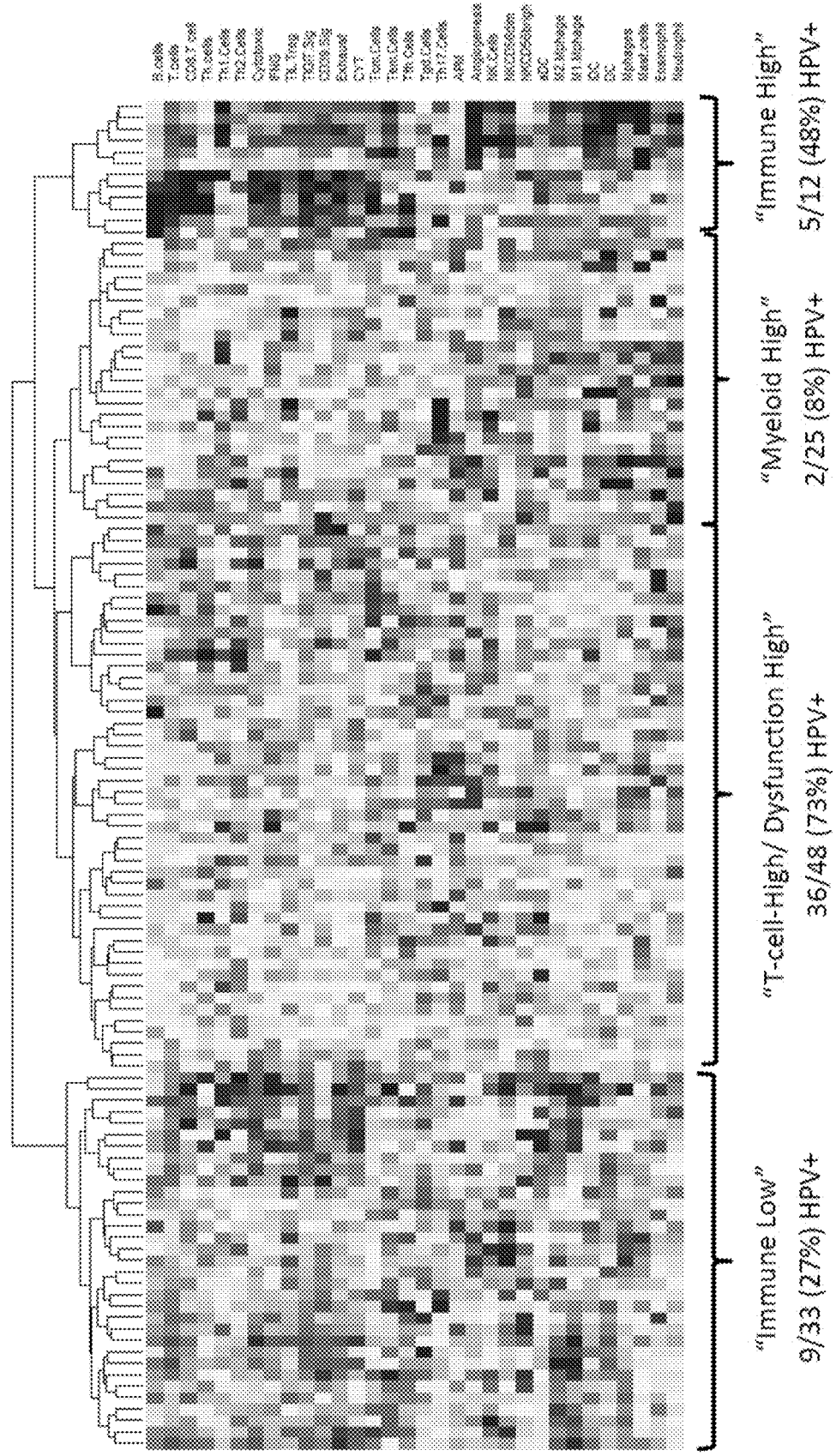
Figure 5A:
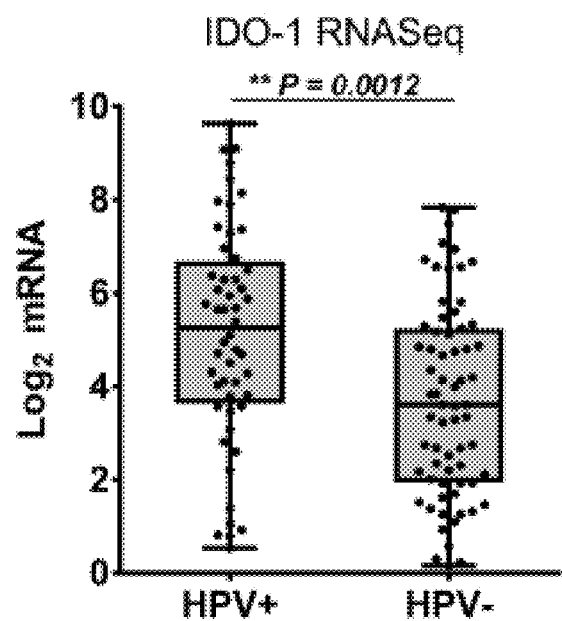
FIGS. 5A-5H demonstrate that IDO-1 is an HPV-specific immune target and can enhance HPV-T-cell cytotoxicity. IDO-1 was one of the highest differentially expressed genes from the exhaustion set (FIG. 5E) in HPV+HNSCCs compared to HPV−HNSCCs (FIG. 5A) and is also highly expressed in the HPV-malignancy cervical cancer (FIG. 5F). The specific correlation of IDO1 expression with E7-protein expression in HPV16+cell lines (FIGS. 5B-5C and 5G) suggests a link to immune selection pressure from TILs. PD-1 protein expression on the same cell lines showed no correlation with E7-antigen expression (FIG. 5H). Treatment with an IDO-1 inhibitor individually, and in combination with an anti-PD-1 antibody, increased the sensitivity to E7-CTL mediated cytotoxicity (FIGS. 5D-5E) in a HPV+ HNSCC cell line with high expression of IDO-1, E7 and PD-L1. These results demonstrate that inhibition of IDO-1 in combination with PD-1 inhibition can sensitize HPV+ HNSCCs to HPV-CTL mediated cytotoxicity.
Figure 5B:
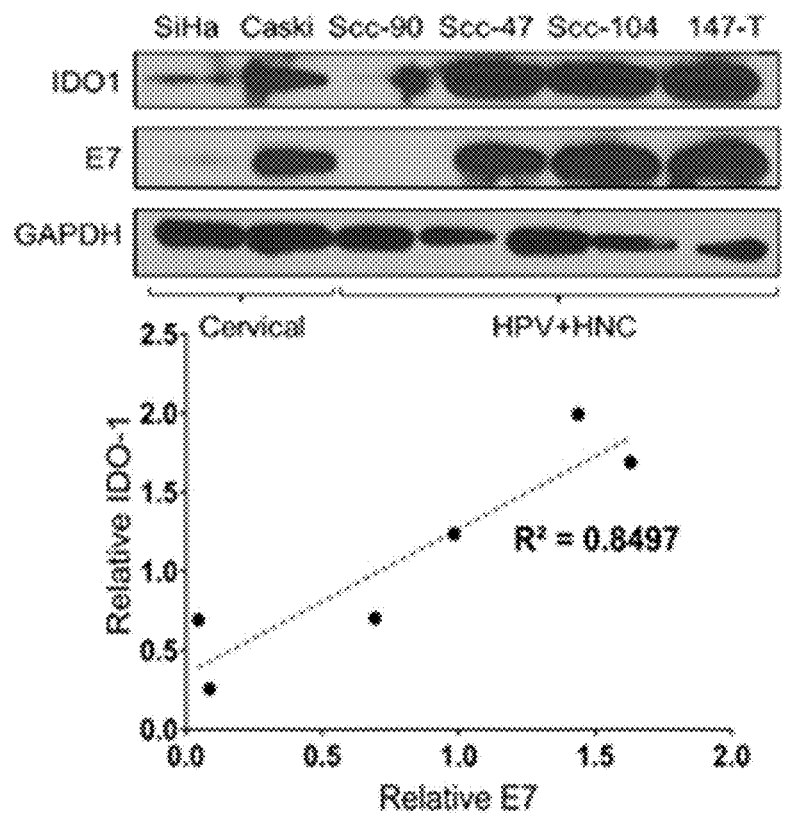
Figure 5C:
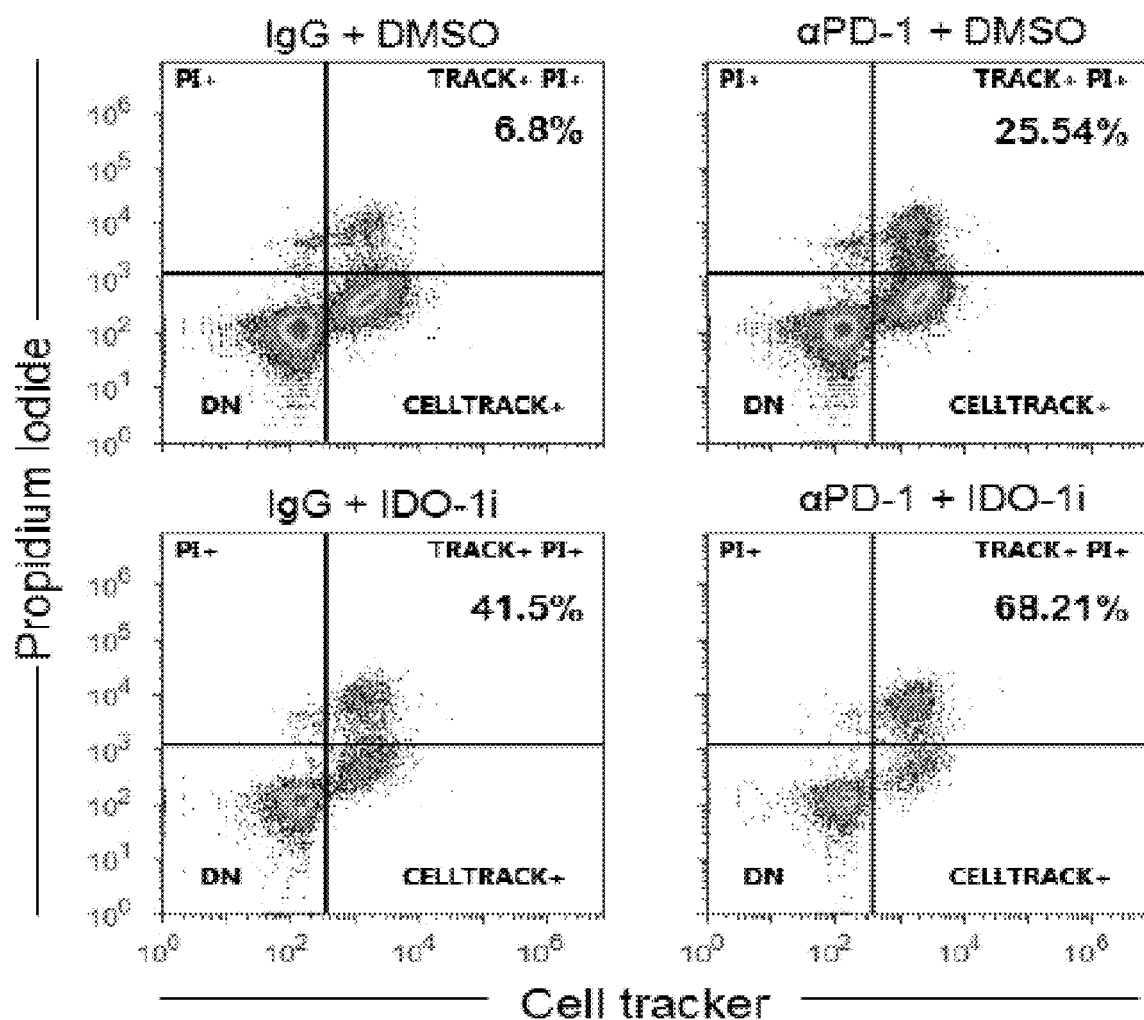
Figure 5D:
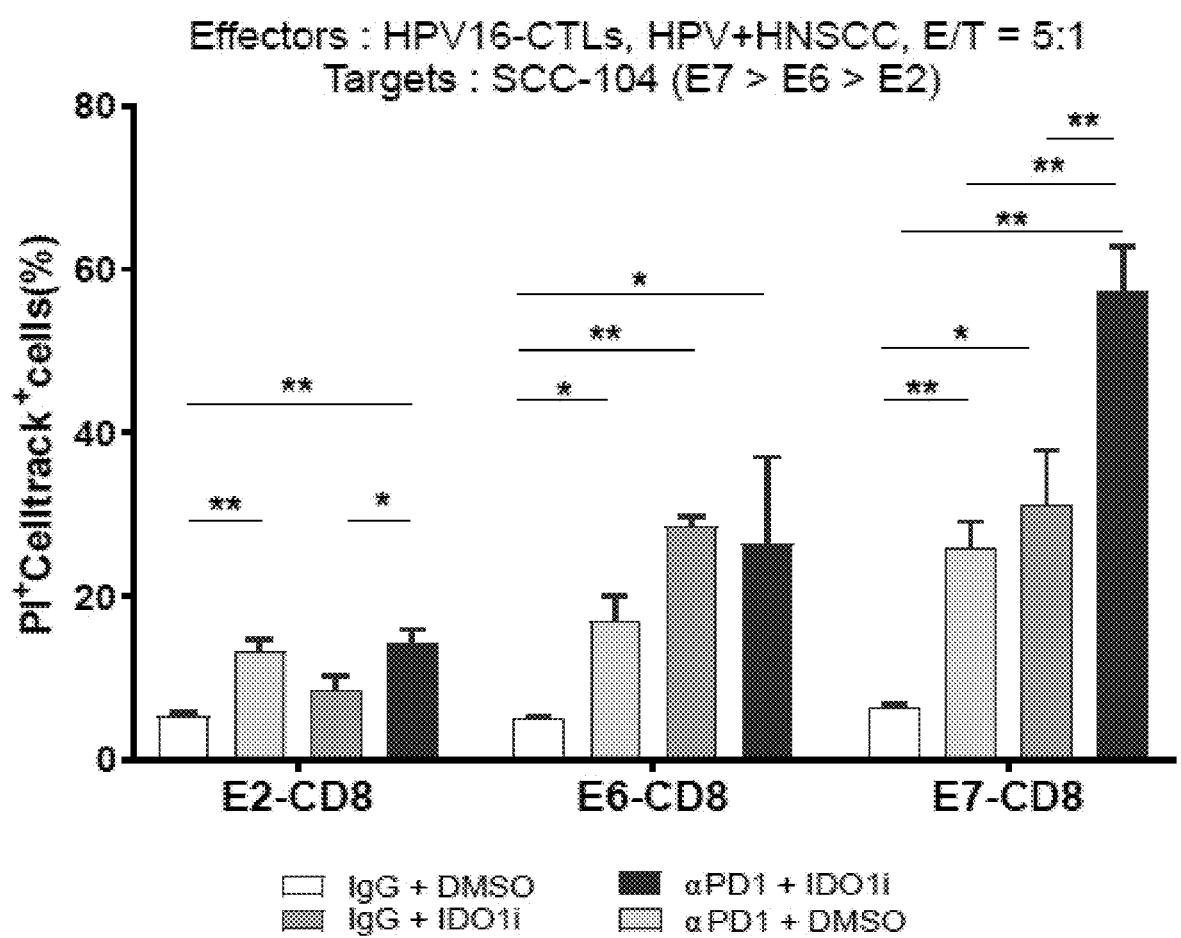
Figure 5E:
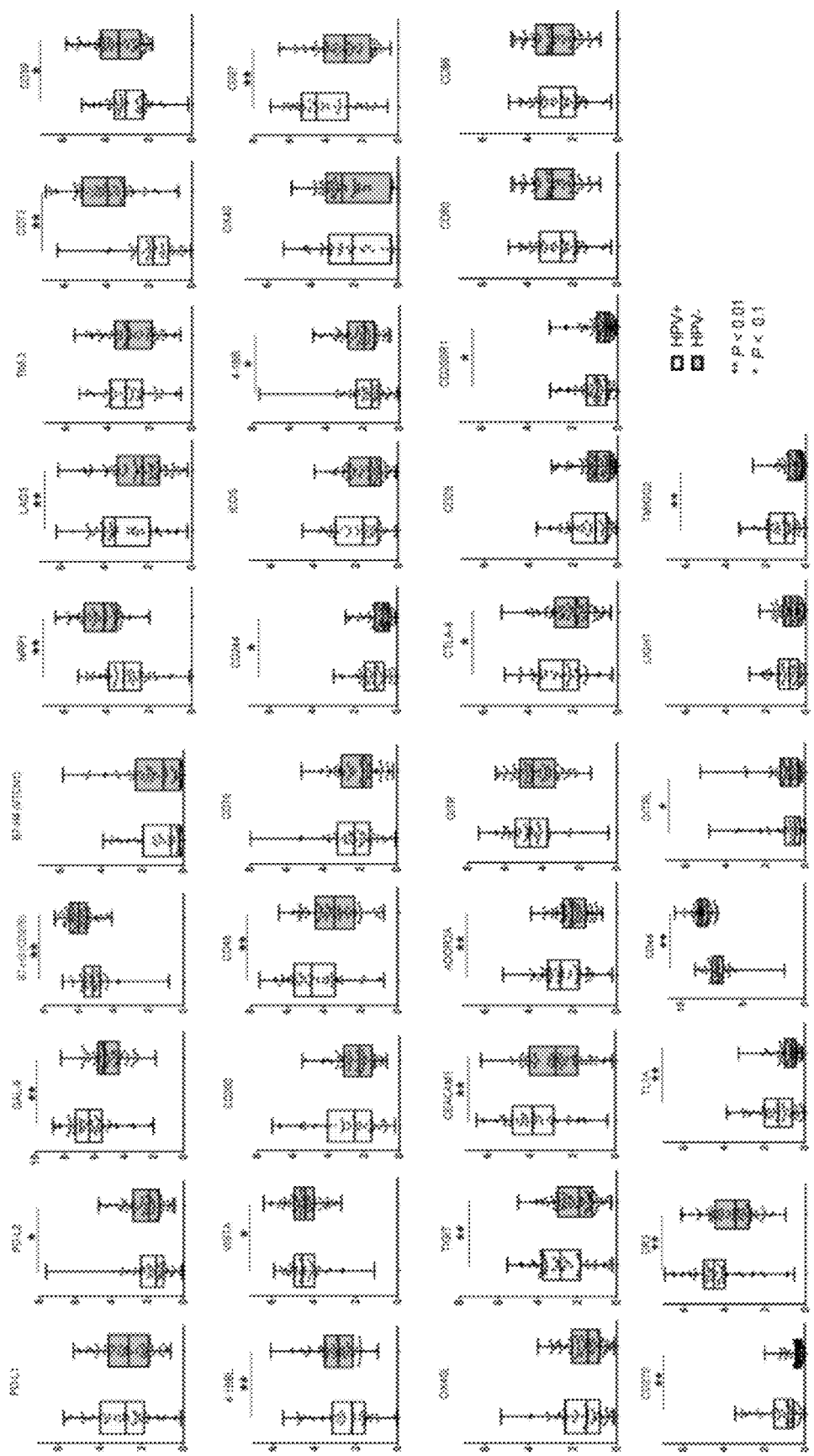

In addition to the PD-1 checkpoint, it was demonstrated both by computational and experimental in vitro assays that IDO-1 is highly expressed in HPV+ HNSCC and other HPV-driven malignancies (FIG. 5A). HPV+ HNSCCs expressing IDO-1 might be driven by HPV-specific-CTL infiltration in response to high tumoral HPV antigen load (FIGS. 4 and 5). In vitro, this resistance to CTL-targeting by HPV+ HNSCCs is apparent in the absence of PD-1/IDO-1 inhibition, where only ~5% of SCC-104 cells were sensitive to CTL-cytotoxicity regardless of the antigen-specificity of the HPV-CTLs (FIG. 5E). In contrast, inhibition of IDO-1 alone or in combination with PD-1 blockade significantly enhances tumor cell cytotoxicity of E7-CTL (and, to a lesser extent, E2 and E6-CTL) derived from patients with HPV+ HNSCCs (FIG. 5E). These data demonstrate that IDO-1/PD-1 blockade may have a significant effect to activate pre-existing HPV-specific CTL in the majority of HPV+ HNSCCs.

Embodiments of the present disclosure pertain generally to cancers associated with human papillomavirus subtype 16 (HPV16) infections. More particularly, the present disclosure provides novel immunogenic epitopes from HPV16 E2, E6 and E7 antigens restricted by common human leukocyte antigen (HLA) alleles for the diagnosis and treatment of HPV16-associated cancers. The HPV16 epitopes identified in the present disclosure can be used for identification of HPV16 infections and for targeted immunotherapy when used in combination with various immune checkpoint inhibitors.

Human papillomavirus (HPV) is the most common sexually transmitted infection globally. Most people have been unknowingly infected at some point during their lives because many of the infections cause no symptoms and are cleared by the immune system without intervention. When certain subtypes of HPV infection become persistent and unable to be cleared by the immune system it can lead to cancer. HPV subtypes 16 and 18 are considered high-risk for the development of cancer. HPV subtype 16 has been implicated in the majority of HPV-associated cervical cancers, anal cancers, head and neck cancers, vaginal cancers, vulvar cancers, penile cancers, and rectal cancers. A subset of HNSCCs are caused by HPV (HPV+HNSCC), with HPV16 responsible for 70-80% of those cases. Embodiments of the present disclosure pertain to any HPV16-associated diseases, including but not limited to, head and neck squamous cell carcinoma (HNSCC).

The present disclosure identified several novel immunogenic CD8+ T-cell (CTL) epitopes from 3 HPV16 antigens. In one embodiment of the present disclosure, at least one synthetic polypeptide encoding one of the CTL epitopes from E2, E6, or E7 HPV16 antigens are included in an immunogenic composition for treating a HPV16-associated disease. The CTL epitope(s) from the HPV16 E2 antigen can include RLECAIYYK (SEQ ID NO:4), VYLTAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAPILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24). The CTL epitope from the HPV16 E6 antigen can include IILECVYCK (SEQ ID NO:26), ISEYRHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43). The CTL epitope from the HPV16 E7 antigen can include LQPETTDLY (SEQ ID NO:46), HGDTPTLHEY (SEQ ID NO:47), TPTLHEYML (SEQ ID NO:51), and QPETTDLYCY (SEQ ID NO:52).

The immunogenic compositions disclosed herein can also include one or more pharmaceutically acceptable excipients. As would be appreciated by one of skill in this art based on the present disclosure, excipients can be chosen based on the route of administration, and can be formulated in dosages appropriate for each route of administration. Suitable excipients include diluents, thickening agents, buffer agents, preservatives, surface active agents, adjuvants, detergents, emulsifiers, stabilizers, immunostimulants, and/or others.

Embodiments of the present disclosure also include a method of treating the subject infected with a HPV16-associated disease by administering an immunogenic composition described herein to induce an immune response in the subject. In accordance with these embodiments, the method includes treatment of any HPV16-associated disease, including but not limited to cervical cancer, anal cancer, head and neck cancer, vaginal cancer, vulvar cancer, penile cancer, and rectal cancer.

In some embodiments, the immunogenic composition includes an immune checkpoint inhibitor. An immune checkpoint inhibitor includes any agent capable inhibiting the function of an immune checkpoint protein and/or pathway. Known immune checkpoint proteins/pathways include PD1 and its ligands PD-L1 and PD-L2, and in addition, IDO-1, CTLA-4, LAG-3, BTLA, B7H3, B7H4, TIMS, KIR. Cancer cells possess mechanisms to exploit these checkpoints and avoid being attacked by the immune system. There are a number of immunotherapeutic agents (immune checkpoint inhibitors) that are known to inhibit immune checkpoint proteins thereby initiating an immune response. Immune checkpoint inhibitors can include antibodies that specifically recognize immune checkpoint proteins. A number of PD1, PDL-1, PD-L2, IDO-1, CTLA-4, LAG-3, BTLA, B7H3, B7H4, 4-1BB (CD137), TEVI3 and KIR inhibitors are known. Examples of PD-1 inhibitors include without limitation humanized antibodies blocking human PD-1 such as Pembrolizumab (formerly Lambrolizumab), or Pidilizumab as well as fully human antibodies such as nivolumab (previously known as MDX-1 106 or BMS-936558). Examples of IDO-1 inhibitors include Epacadostat, Navoximod, Norharmane, and Indiximod. In one embodiment of the present disclosure, the checkpoint inhibitor is the IDO-1 inhibitor Epacadostat. In another embodiment the checkpoint inhibitor is an anti-PD-1 antibody.

Cancer immunotherapy can also include adaptive cell transfer (ACT). ACT involves the transfer of cells into a patient. The cells may originate from the patient or another individual. In some cases, T-cells are isolated from a patient, re-engineered based on the cancer diagnosis, and re-introduced back into the patient to bolster the immune response to the cancer cells. There are several types of immunotherapies that use ACT including tumor-infiltrating lymphocytes (TILs), high affinity T-cell receptors (TCRs), and chimeric antigen receptor (CARs). Both TCR- and CAR-based therapies re-engineer the T-cells to express a modified cell surface receptor capable of recognizing a specific tumor antigen. When these T-cells are reintroduced into the patient, they can recognize and kill cancer cells expressing that specific tumor antigen. One of the differences between TCR- and CAR-based therapies is the type of molecules they recognize. CAR T-cells recognize proteins expressed on the cell surface. TCRs recognize tumor-specific proteins on the inside of cells. When tumor-specific proteins are broken into fragments they show up on the cell surface with another protein called major histocompatibility complex (MHC). TCRs can be engineered to recognize a tumor-specific protein fragment/MHC combination.

Embodiments of the present disclosure also include an immune cell comprising a T-cell receptor (TCR) capable of binding a synthetic polypeptide encoding a CTL epitope derived from E2, E6, or E7 HPV 16 antigen. The CTL epitope from the HPV16 E2 antigen can include RLECAIYYK (SEQ ID NO:4), VYLTAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAPILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24). The CTL epitope from the HPV16 E6 antigen can include IILECVYCK (SEQ ID NO:26), ISEYRHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43). The CTL epitope from the HPV16 E7 antigen can include LQPETTDLY (SEQ ID NO:46), HGDTPTLHEY (SEQ ID NO:47), TPTLHEYML (SEQ ID NO:51), and QPETTDLYCY (SEQ ID NO:52).

One of the reasons HPV is well-suited for immunotherapy treatment is the early presence of emerging immune and viral biomarkers which allow for early detection. In studies of T-cell responses to viral infection, the predefined antigen repertoire encoded by the virus genome determines the specificity of virus-responsive T cells, which are often present in detectable frequencies following infection. Similarly, in chronic viral infections such T cells are detectable through life. Knowledge of those antigens for a virus and identifying cells expressing the T-cell receptor specific for that given antigen would allow early detection of infection.

Embodiments of the present disclosure include a method of detecting a HPV16-associated disease by quantifying T-cells that are specific for a given HPV antigen within a biological sample using an MHC tetramer assay. MHC tetramers exhibit a substantially higher affinity for a T-cell of interest than MHC monomers or dimers do, and are well-established reagents for the detection of antigen-specific T-cells by flow cytometry or fluorescence activated cell sorting (FACS). Tetramers bind to T-cells that are specific for both the MHC type and peptide being used in the tetramer. Usually cytotoxic T cells express CD8 on their surface, and are activated by binding to a complex of antigenic peptide and Class I MHC molecule. The MHC class I proteins in the present disclosure are bound by one of the synthetic polypeptides encoding epitopes derived from E2, E6, or E7 human papillomavirus subtype 16 (HPV16) antigens thereby only recognizing T-cells that have encountered the HPV16 virus. MHC tetramers are formed from individual MHC molecules, each bound by a synthetic peptide antigen. In some embodiments the individual MHC molecules each contain a ligand which binds to a polyvalent molecule binding partner to form a tetramer (i.e., a biotin ligand will bind to a streptavidin tetravalent molecule). In some embodiments, individual MHC molecules each contain a self-associating domain that naturally forms a tetramer when in solution.

Flow cytometry, also referred to as fluorescence activated cell sorting (FACS), provides a method for sorting a heterogeneous mixture of biological cells into two or more containers, one cell at a time, based upon the specific light scattering and fluorescent characteristics of each cell. This method can provide fast, objective and quantitative recording of fluorescent signals from individual cells as well as physical separation of cells of particular interest. In an MHC tetramer assay, the fluorescent label can be located on the MHC tetramer, which can allow separation of unlabeled T-cells from those containing the bound MHC tetramer thereby detecting the T-cells expressing the receptor able to identify the epitope specific to the disease antigen. Positive identification of T-cells expressing the epitope-specific receptor demonstrates the presence of the virus within the subject. Other methods for detecting and/or quantifying T cells can also be used, as would be recognized by one of ordinary skill in the art based on the present disclosure.

EXAMPLES

The following examples are illustrative of disclosed methods. In light of the present disclosure, those of skill in the art will recognize that variations of these examples and other examples of the disclosed method would be possible without undue experimentation.

Example 1

Frequency and specificity of HPV16 E2, E6 and E7-specific CTLs in HPV+ HNSCC. A systematic analysis was performed of potential CTL-epitopes from HPV16 E2, E6 and E7 antigens restricted by 15 globally frequent HLA class I alleles representative of major HLA supertypes (FIG. 1). A comprehensive CTL-epitope prediction strategy was used, developed by incorporating stringent selection criteria to control for inter-algorithmic variations. Fifty-nine candidate peptides (24 from E2, 20 from E6 and 15 from E7) were selected covering 13 of the 15 common HLA class-I alleles as candidate HPV-CTL peptides based on predicted HLA-affinity and antigen processing percentile scores (FIG. 1). Several previously described HLA-A*02:01-restricted HPV16 E6 and E7 epitopes were predicted with high scores (e.g., E6-KLP epitope, total percentile 94.6; Tables 1-4) confirming the prediction strategy.

Tables 1-4: Summary of all predicted candidate HPV16-E2, E6 and E7 epitopes, and cross-reactive epitopes. Peptide pool information from each antigen, relevant information for the epitope's information from HPV T-cell antigen database (cvc.dfci.harvard.edu/hpv/).

TABLE 1

E2 Epitopes

| Pool | Epitope label | Position | HLA | Super-type | Sequence | Epitope length | Epitope (HPVdb) | Ligand (HPVdb) | Accession Number (HPVdb) | Conservation (HPVdb) | Most Common HPV16-variants (HPVdb) | Previous HLA described for (HPVdb) | HPVdb Reference | IEDB.ANN bind | IEDB.NetMHC bind | Syfpeithi bind | IEDB.ANN bind per-prot | per-cen-tile prot | per-cen-tile tile | bind total per-cen-tile |
|---|---|---|---|---|---|---|---|---|---|---|---|---|---|---|---|---|---|---|---|---|
| Pool 1 | A01-A03-B57-E2 | E2 (329-338) | HLA-B*15:01 | B62 | KSAIVTLTY (SEQ ID NO: 1) | 9 | Yes | Yes | T000016 | 78/ 82-95% | KSAIVTLR YD | DR | 11809698 | 0.8 | 78.78 | 15 | 0.96 | 0.8182 | 6282 | .54 |
| | | E2 (329-338) | HLA-B*57:01 | B58 | KSAIVTLTY | 9 | Yes | Yes | T000017 | 78/ 82-95% | KSAIVTLR YD | DR | 11809699 | 0.55 | 116.59 | 14 | 1.15 | 0.6481 | 7881 | .96 |
| | | E2 (329-338) | HLA-A*01:01 | A01 | KSAIVTLTY | 9 | Yes | Yes | T000018 | 78/ 82-95% | KSAIVTLR YD | DR | 11809700 | 0.55 | 128.89 | 22 | 0.28 | 0.6 | 88.9789 | .92 |
| | | E2 (329-338) | HLA-A*11:01 | A03 | KSAIVTLTY | 9 | Yes | Yes | T000019 | 78/ 82-95% | KSAIVTLR YD | DR | 11809701 | 1.35 | 151.72 | 15 | 0.61 | 0.5382 | 3984 | .93 |
| | | E2 (329-338) | HLA-A*03:01 | A03 | KSAIVTLTY | 9 | Yes | Yes | T000020 | 78/ 82-95% | KSAIVTLR YD | DR | 11809702 | 1.15 | 245.15 | 19 | 0.15 | 0.3285 | 9989 | .78 |
| | | E2 (329-338) | HLA-B*35:01 | B07 | KSAIVTLTY | 9 | Yes | Yes | T000021 | 78/ 82-95% | KSAIVTLR YD | DR | 11809703 | 3.1 | 266.25 | 11 | -0.09 | 0.2878 | 1285 | .46 |
| | A02-E2-1 | E2 (93-101) | HLA-A*02:01 | A02 | TLQDVSL EV (SEQ ID NO: 2) | 9 | Yes | No | T000011 | 100% | None | A0201 | 17325352 | 0.5 | 9.82 | 24 | 0.2 | 0.2990 | 8892 | .64 |
| | A02-E2-2 | E2 (138-147) | HLA-A*02:01 | A02 | YICEEAS VTV (SEQ ID NO: 3) | 10 | Yes | No | T000012 | 58/ 82-70% | YICEDTSV TV | A0201 | 17325352 | 0.8 | 125.98 | 26 | -0.73 | -0.6992 | .5 | 89.87 |
| | A03-E2-1 | E2 (37-45) | HLA-A*02:01 | A03 | RLECAIY YK (SEQ ID NO: 4) | 9 | Not Found | * | * | * | * | * | * | 0.65 | 50.91 | 17 | -0.34 | -0.5684 | 4987 | .15 |
| | | E2 (37-45) | HLA-A*03:01 | A03 | RLECAIY YK | 9 | Not Found | * | * | * | * | * | * | 0.4 | 152.21 | 24 | -0.73 | -1.0490 | 8187 | .45 |
| | A11-E2-1 | E2 (284-292) | HLA-A*11:01 | A03 | NTTPIVH LK (SEQ ID NO: 5) | 9 | Yes | Yes | T000014 | 79/ 82-96% | NTTSIVHL K | DR | 11809698 | 0.6 | 34.72 | 24 | -0.12 | -0.2890 | 8292 | .97 |
| | A24-E2-2 | E2 (101-110) | HLA-A*24:02 | A24 | VYLTAPT GCI (SEQ ID NO: 6) | 10 | Not Found | * | * | * | * | * | * | 1.05 | 162.38 | 24 | -1.06 | -0.8790 | 5986 | .68 |
| | B07-E2-1 | E2 (207-215) | HLA-B*07:02 | B07 | SPEIIRQ HL (SEQ ID NO: 7) | 9 | Not Found | * | * | * | * | * | * | 0.7 | 73.94 | 21 | 0.13 | 0.1288 | 0691 | .91 |

TABLE 1-continued

E2 Epitopes

| Pool | Epitope label | Position | HLA | Super-type | Sequence | length | Epitope | Ligand | Accession Number | Conservation | Most Common Mutations in sequence | HLA | HPVdb-Reference | IEDB.NetMHC bind | bind | Syf-peithi bind | IEDB.ANN cen-prot | per-prot | per-cen-tile | total tile |
|---|---|---|---|---|---|---|---|---|---|---|---|---|---|---|---|---|---|---|---|---|
| | B08-B27-E2 | E2 (303-311) | HLA-B*08:01 | B08 | YRFKKHCTL (SEQ ID NO: 8) | 9 | Yes | Yes | T000015 | 31/82-38% | YRPKKHCKDRL | * | 11809698 | 0.3 | | 11.1 | 20 | 0.51 | 1.2887 | 3485.27 |
| | | E2 (303-311) | HLA-B*27:05 | B27 | YRFKKHCTL | 9 | Yes | Yes | T000016 | 31/82-38% | YRPKKHCKDRL | * | 11809699 | 0.3 | | 119.83 | 27 | 0.89 | 0.2593 | 5791.65 |
| | | E2 (303-311) | HLA-B*40:02 | B44 | YRFKKHCTL | 9 | Yes | Yes | T000017 | 31/82-38% | YRPKKHCKDRL | * | 11809700 | 2.8 | | 695.16 | 14 | -1.2 | -0.5180 | 6381.6 |
| E2 Pool 2 | A01-E2-1 | E2 (147-155) | HLA-A*01:01 | A03 | VVEGQVDYY (SEQ ID NO: 9) | 9 | Not Found | * | * | * | * | * | * | 34.5 | | 228.27 | 26 | 0.39 | 0.2581 | 1886.22 |
| | A02-E2-3 | E2 (69-77) | HLA-A*02:01 | A02 | ALQAIELQL (SEQ ID NO: 10) | 9 | Yes | No | T000010 | 82/82-100% | None | A0201 | 17325352 | 3.6 | | 213.45 | 23 | 0.17 | -0.2788.8 | 91.59 |
| | A02-E2-5 | E2 (310-318) | HLA-A*02:01 | A02 | TLYTAVSST (SEQ ID NO: 11) | 9 | Yes | No | T000015 | 29/82-35% | KLYTAVSSDR, DR1, DR2, DR3 | * | 11809698 | 3.6 | | 656.75 | 21 | -2.19 | -2.1786 | 6974.57 |
| | A03-E2-2 | E2 (267-276) | HLA-A*03:01 | A03 | ILTAFNSSHK (SEQ ID NO: 12) | 10 | Not Found | * | * | * | * | * | * | 0.35 | | 25.3 | 27 | -0.71 | -0.5593 | 6291.19 |
| | A11-E2-2 | E2 (267-276) | HLA-A*11:01 | A03 | ILTAFNSSHK | 10 | Not Found | * | * | * | * | * | * | 0.95 | | 75.17 | 17 | -1.11 | -1.0284 | 3782.15 |
| | | E2 (103-112) | HLA-A*11:01 | A03 | LTAPTGCIKK (SEQ ID NO: 13) | 10 | Not Found | * | * | * | * | * | * | 0.45 | | 64.89 | 26 | -0.59 | -0.6392 | 6690.77 |
| | | E2 (103-112) | HLA-A*03:01 | A03 | LTAPTGCIKK | 10 | Not Found | * | * | * | * | * | * | 1.1 | | 234.38 | 14 | -1.3 | -1.1881 | 5179.02 |
| | B07-E2-2 | E2 (218-227) | HLA-B*07:02 | B07 | HPAATHTKAV (SEQ ID NO: 14) | 10 | Not Found | * | * | * | * | * | * | 0.35 | | 16.59 | 20 | 0.01 | 0.1887 | 3291.71 |
| | B08-E2-1 | E2 (62-70) | HLA-B*08:01 | B08 | LAVSKNKAL (SEQ ID NO: 15) | 9 | Not Found | * | * | * | * | * | * | 1.3 | | 232.92 | 27 | -0.84 | -0.3893 | 1691.08 |
| | | E2 (62-70) | HLA-B*35:01 | B07 | LAVSKNKAL | 9 | Not Found | * | * | * | * | * | * | 4.3 | | 666.47 | 13 | -1.47 | -0.8479 | 2478.36 |

TABLE 1-continued

E2 Epitopes

| ID | HLA | Position | Epitope | Len | Found | | | | | Epitope ID | Match% | Peptide | DR | | IEDB ID | Score1 | Score2 | Score3 | Score4 | Score5 |
|---|---|---|---|---|---|---|---|---|---|---|---|---|---|---|---|---|---|---|---|---|
| B35-E2-1 | HLA-B*35:01 | E2 (263-271) | DSAPILTAF (SEQ ID NO: 16) | 9 | Not Found | * | * | * | * | * | | | | * | | 2.6 | 166.28 | 12 | 0.55 | 0.0979 | 2685.07 |
| A01-E2-2 | HLA-B*15:01 | E2 (94-102) | LQDVSLEVY (SEQ ID NO: 17) | 9 | Not Found | * | * | * | * | * | | | | * | | 0.8 | 243.23 | 21 | -0.3 | 87.9190.42 |
| E2 Pool 3 / A03 | HLA-A*01:01 | E2 (94-102) | LQDVSLEVY | 9 | Not Found | * | * | * | * | * | | | | * | | 41 | 259.3 | 27 | -0.2 | 0.2779 | 8986.12 |
| A02-E2-4 | HLA-A*02:01 | E2 (102-110) | YLTAPTGCI (SEQ ID NO: 18) | 9 | Not Found | * | * | * | * | * | | | | * | | 4.4 | 470.3 | 22 | -1.22 | -1.4187 | 4581.98 |
| A02-E2-6 | HLA-A*02:01 | E2 (191-199) | QVILCPTSV (SEQ ID NO: 19) | 9 | Not Found | * | * | * | * | * | | | | * | | 4.6 | 672.2 | 18 | -1.86 | -1.6483 | 6476.2 |
| A02-E2-6 | HLA-A*02:01 | E2 (297-306) | TLKCLRYRFK (SEQ ID NO: 20) | 10 | Yes | * | * | * | T000017 | 80/ 82-98% | ILKCLRYRF | DR, DR1, DR2, DR3 | * | 11809698 | 53.5 | 24400.31 | 9 | -3.11 | -3.0742 | 8440.94 |
| A02-E2-6 | HLA-A*03:01 | E2 (297-306) | TLKCLRYRFK | 10 | Yes | * | * | * | T000018 | 80/ 82-98% | ILKCLRYRF | DR, DR1, DR2, DR3 | * | 11809699 | 0.45 | 85.36 | 21 | -0.67 | -0.6288 | 1487.78 |
| | HLA-A*11:01 | E2 (297-306) | TLKCLRYRFK | 10 | Yes | * | * | * | T000019 | 80/ 82-98% | ILKCLRYRF | DR, DR1, DR2, DR3 | * | 11809700 | 1.05 | 86.84 | 16 | -0.89 | -0.6383 | 4384.04 |
| A24-E2-1 | HLA-A*24:02 | E2 (302-312) | RYRFKKHCTL (SEQ ID NO: 21) | 10 | Yes | * | * | * | T000015 | 31/ 82-38% | RYRFKKHCKL | DR, DR1, DR2, DR3, DR4 | * | 11809698 | 0.55 | 120.86 | 20 | 0.11 | 0.3287 | 1890.66 |
| | HLA-B*27:05 | E2 (302-312) | RYRFKKHCTL | 10 | Yes | * | * | * | T000015 | 31/ 82-38% | RYRFKKHCKL | DR, DR1, DR2, DR3, DR4 | * | 11809698 | 10.6 | 122.95 | 15 | 0.73 | 0.3279 | 3283.46 |
| B07-E2-3 | HLA-B*07:02 | E2 (249-257) | NPCHTTKLL (SEQ ID NO: 22) | 9 | Not Found | * | * | * | * | * | | | | * | | 1.1 | 1802.85 | 21 | -1.43 | -1.5586 | 7480.14 |

TABLE 1-continued

E2 Epitopes

| | | | | | | | | | | | | |
|---|---|---|---|---|---|---|---|---|---|---|---|---|
| B08-E2-2 (163-171) | HLA-B*15:01 | B62 | GIRTYFVQF (SEQ ID NO: 23) | 9 | Not Found | * | * | * | * | 0.3 | 110.82 | 16 | 0.27 | 0.6783 | 6786.49 |
| E2 (163-171) | HLA-B*08:01 | B08 | GIRTYFVQF | 9 | Not Found | * | * | * | * | 1.8 | 365.55 | 18 | -0.35 | 0.1584 | 7988.95 |
| B35-E2-2 (158-167) | HLA-B*15:01 | B62 | YYVHEGIRTY | 10 | Not Found | * | * | * | * | 8.75 | 59.78 | 14 | 1.11 | 1.0579 | 0878.85 |
| E2 (158-167) | HLA-B*35:01 | B07 | YYVHEGIRTY (SEQ ID NO: 24) | 10 | Not Found | * | * | * | * | 0.8 | 485.11 | 13 | 0.3 | 0.1480 | 5486.64 |

TABLE 2

E6 Epitopes

| Epitope label | Pool | Position | HLA | Sequence | Super-type | Epitope length | Epitope (HPVdb) | Ligand (HPVdb) | Accession Number (HPVdb) | Conservation (HPVdb) | Most Common HPV16-variants (HPVdb) | Previous HLA described for (HPVdb) | HPVdb-Reference | IEDB. bind | NetMHC. bind | Syfpeithi bind | IEDB.ANN. prot | bind per-prot | total per-cen-tile | per-cen-tile |
|---|---|---|---|---|---|---|---|---|---|---|---|---|---|---|---|---|---|---|---|
| A24-E6 | Pool-B08-E6 | E6 (82-90) | HLA-A*24:02 | EYRHCYS L (SEQ ID NO: 25) | A24 | 9 | Yes | No | T000063 | 46/118 39% | EYRYY CYSL | A2402 | 22032938 | 1.3 | 573.3 | 19 | -0.68 | -0.86 | 89.14 | 87.52 |
| | | E6 (82-90) | HLA-B*08:01 | EYRHCYS L | B08 | 9 | Yes | No | T000064 | 46/118 39% | EYRYY CYSL | A2402 | 22032939 | 1.3 | 588.7 | 18 | -0.69 | -0.4 | 88.12 | 88.7 |
| A03-E6-1 | | E6 (33-41) | HLA-A*03:01 | IILECVYC K (SEQ ID NO: 26) | A03 | 9 | No | Yes | L000026 | 102/118 87% | IILQC VYCK | A11 | 7511661 | 0.7 | 265.9 | 23 | -1.28 | -1.21 | 93.59 | 86.41 |
| | | E6 (33-41) | HLA-A*11:01 | IILECVYC A03 | A03 | 9 | No | Yes | L000026 | 102/118 87% | IILQC VYCK | A11 | 7511661 | 0.55 | 35.9 | 18 | -0.41 | -0.49 | 88.74 | 89.83 |
| A01-E6-1 | | E6 (80-88) | HLA-A*01:01 | ISEYRHYC Y (SEQ ID NO: 27) | A01 | 9 | No | Yes | L000031 | 70/118 59% | ISEYR YYCY | A1 | 7511661 | 0.25 | 107.9 | 27 | 0.82 | 1.33 | 97.89 | 90.34 |
| B35-B57-E6 | | E6 (59-67) | HLA-B*15:Y | IVYRDGNP Y (SEQ ID NO: 28) | B62 | 9 | No | Yes | L000022 | 112/118 95% | IVYKD GNPY | A3 | 7511661 | 0.7 | 46.1 | 18 | 0.88 | 0.76 | 88.69 | 86.85 |
| | | E6 (59-67) | HLA-B*35:01 | IVYRDGNP Y | B07 | 9 | No | Yes | L000022 | 112/118 95% | IVYKD GNPY | A3 | 7511661 | 0.9 | 36.9 | 12 | 0.98 | 1.07 | 82.57 | 81.55 |
| | | E6 (59-67) | HLA-B*57:01 | IVYRDGNP Y | B58 | 9 | No | Yes | L000022 | 112/118 95% | IVYKD GNPY | A3 | 7511661 | 2.75 | 6475.6 | 4 | -1.27 | -0.97 | 69.53 | 72.97 |
| A02-E6-1 | | E6 (18-26) | HLA-A*02:01 | KLPQLCTE A (SEQ ID NO: 29) | A02 | 9 | Yes | No | T000057 | 70/118 59% | KLPDL CTEL | A0201 | 17589293 | 1.8 | 227 | 24 | -0.43 | -0.1 | 94.26 | 94.61 |
| B07-E6-1 | | E6 (15-24) | HLA-B*07:02 | RPRKLPQL B07 (SEQ ID NO: 30) | B07 | 10 | Yes | No | T000052 | 65/118 55% | RPIKL PDLCT | DP017 | 17955486 | 1.5 | 496.2 | 22 | -2.03 | -1.56 | 92.16 | 81.18 |
| A11-E6-1 | | E6 (93-101) | HLA-A*11:01 | TTLEQQYN K (SEQ ID NO: 31) | A03 | 9 | No | Yes | L000020/ L000021 | 117/118 99% | TALEQ QYNK | A3/A11 | 7511661 | 0.3 | 27.5 | 21 | -0.44 | -0.38 | 91.86 | 92.02 |

TABLE 2-continued

E6 Epitopes

| Pool | Epitope label | Position | HLA Supertype | Sequence | type | length | Epitope | Ligand | Accession Number | Conservation | Most Common Mutations in sequence | Previous HLA described for | HPVdb-Reference | IEDB bind | NetMHC bind | Syfpeithi bind | IEDB.ANN. prot bind | total per prot tile | per cen tile |
|---|---|---|---|---|---|---|---|---|---|---|---|---|---|---|---|---|---|---|---|
| E6-Pool-E6-2 | A03-E6-2 | (68-77) | HLA-A*11:01 | AVCDKCLKFY (SEQ ID NO: 32) | A03 | 10 | Yes | No | T000042 | 101/118 86% | AVCDK CLKLY | DP | 17955486 | 2.5 | 533.8 | 15 | 0.03 | 0.4284 | 7389.21 |
|  | A24-E6-2 | (87-95) | HLA-A*24:02 | CYSLYGTTL (SEQ ID NO: 33) | A24 | 9 | Yes | No | T000054 | 78/118 64% | CYSVY GTTL | A2402 | 22032938 | 0.75 | 189.4 | 20 | -0.21 | 0.0390 | 5993.56 |
|  | B08-E6-1 | (44-52) | HLA-B*15:01 | LLRREVYDF (SEQ ID NO: 34) | B62 | 9 | Yes | No | T000069 | 114/118 97% | LRRRE VYDF | DP | 17955486 | 1.2 | 87.9 | 20 | 0.4 | -0.1190 | 5192.44 |
|  | E6 | (44-52) | HLA-B*08:01 | LLRREVYDF | B05 | 9 | Yes | No | T000069 | 114/118 97% | LRRRE VYDF | DP | 17955486 | 1.5 | 427 | 19 | -0.29 | -0.3689 | 1791.08 |
|  | B07-E6-2 | (65-74) | HLA-B*07:02 | NPYAVCDKCL (SEQ ID NO: 35) | B07 | 10 | Yes | No | T000042 | 105/118 90% | SPYAV CDKCL | DP | 17955486 | 4.1 | 2833.6 | 21 | -1.43 | -1.5388.7 | 81.61 |
|  | A02-E6-2 | (29-38) | HLA-A*02:01 | TIHDILECV (SEQ ID NO: 36) | A02 | 10 | Yes | No | T000029 | 77/118 65% | TIHEI ILECV | A0201 | 15609329 | 2.65 | 320.2 | 23 | -1.2 | -1.1392.9 | 86.64 |
|  | A01-E6-2 | (69-77) | HLA-A*01:01 | VCDKCLKF (SEQ ID NO: 37) | A01 | 9 | Yes | No | T000067 | 104/118 97% | VCDKC LKLY | DP | 17955486 | 0.95 | 4559.1 | 26 | -0.98 | -1.1393 | 6487.96 |
|  | B35-E6-1 | (67-76) | HLA-B*35:01 | YAVCDKCLKF (SEQ ID NO: 38) | B07 | 10 | Yes | No | T000042 | 102/118 87% | YAVCD KCLKL | DP | 17955486 | 0.5 | 578.6 | 9 | -0.3 | -0.4479.3 | 84.8 |
|  | E6 | (67-76) | HLA-B*15:01 | YAVCDKCLKF | B62 | 10 | Yes | No | T000042 | 102/118 87% | YAVCD KCLKL | DP | 17955486 | 14.3 | 341.8 | 9 | -0.07 | -0.6674.8682.17 | |

TABLE 2-continued

E6 Epitopes

| | | | * | * | * | * | * | * | * | * | * | * | * |
|---|---|---|---|---|---|---|---|---|---|---|---|---|---|
| E6-pool-3 | B07-E6-3 (119-126) | HLA-B*07:02 CPEEKQRH (SEQ ID NO: 39) | 9 | Not Found | * | * | * | * | * | 2.5 | 893.3 | 20 | -1.47 -1.9189 5480.44 |
| | A11-E6-2 (37-47) | HLA-A*11:01 CVYCKQQLLR (SEQ ID NO: 40) | 10 | Yes | No | T000041 | 116/118-CVYCKQQLRR 98% | DP0210 | 17955486 | 1.9 | 348.8 | 24 | -0.85 -1.0194 1489.25 |
| | E6 (37-47) | HLA-A*03:01 CVYCKQQLLR (SEQ ID NO: 40) | 10 | Yes | No | T000041 | 116/118-CVYCKQQLRR 98% | DP0210 | 17955486 | 1.15 | 377.7 | 21 | -0.88 -0.3691 3490.04 |
| | B08-E6-2 (127-135) | HLA-B*08:01 DKKQRFHNI (SEQ ID NO: 41) | 9 | Yes | No | T000062 | 114/118-DKKQTFHNI 94% | DR1 | 17412975 | 0.2 | 210.8 | 24 | -1.04 -0.8 94.8 89.73 |
| | A02-E6-3 (52-60) | HLA-A*02:01 FAFRDLCIV (SEQ ID NO: 42) | 9 | Yes | No | T000055 | 114/118-FAFQDLCIV 97% | A0201 | 7538538 | 2.3 | 115 | 20 | -0.91 -1.0490 1386.48 |
| | A03-E6-3 (106-116) | HLA-A*03:01 LLIRCINCQK (SEQ ID NO: 43) | 10 | No | Yes | L000024 | 113/118-LLIRCINGQK 96% | A3 | 7511661 | 0.9 | 79.4 | 29 | -0.85 -1.1999 7191.88 |
| | E6 (106-116) | HLA-A*11:01 LLIRCINCQK (SEQ ID NO: 43) | 10 | No | Yes | L000024 | 113/118-LLIRCINGQK 96% | A3 | 7511661 | 1.5 | 196.5 | 17 | -1.25 -1.5 87.3181.61 |
| | B35-E6-2 (82-90) | HLA-B*35:01 YGTTLEQQY (SEQ ID NO: 44) | 9 | Yes | No | T000037 | 117/118-YGTALEQQYN 99% | A24 | 16211234 | 3 | 395.1 | 11 | -0.11 0.0880 6187.77 |

TABLE 3

E7 Epitopes

| Epitope Pool Label | Position | HLA | Super-type | Sequence | Length | Epitope (HPVdb) | Ligand (HPVdb) | Accession Number (HPVdb) | Conservation (HPVdb) | Most Common HPV16-variants (HPVdb) | Previous HLA described for (HPVdb) | HPVdb Reference | IEDB.NetMHC bind | bind | Syf-peithi bind | IEDB.ANN bind prot | per-cen-tile prot | per-cen-tile tile | bind total per-cen-tile |
|---|---|---|---|---|---|---|---|---|---|---|---|---|---|---|---|---|---|---|---|
| E7-Pool-E7-1 | E7 (15-23) | HLA-B*15:01 | B62 | LQPETTDLY (SEQ ID NO: 46) | 9 | Not Found | * | * | * | * | * | * | 0.8 | 233.2 | 22 | 0.03 | 0.34 | 91.09 | 93.7 |
| A01-B35-B57-E7 | E7 (15-23) | HLA-A*01:01 | A01 | LQPETTDLY | 9 | Not Found | * | * | * | * | * | * | 1.85 | 7312.4 | 17 | -1.46 | -1.5 | 81.2 | 77.08 |
| A01-E7 | E7 (2-11) | HLA-A*01:01 | A01 | HGDTPTLHEY (SEQ ID NO: 47) | 10 | No | Yes | L000038 | 17/17-100% | None | A1 | 7511661 | 0.45 | 413.9 | 28 | -0.11 | -0.55 | 96.8 | 95.92 |
| | E7 (2-11) | HLA-B*35:01 | B07 | HGDTPTLHEY | 10 | No | Yes | L000038 | 17/17-100% | None | A1 | 7511661 | 2.05 | 3444.2 | 13 | -1.03 | -1.02 | 79.93 | 80.08 |
| | E7 (2-11) | HLA-B*57:01 | B58 | HGDTPTLHEY | 10 | No | Yes | L000038 | 17/17-100% | None | A1 | 7511661 | 31.35 | 11936 | 10 | -1.57 | -1.37 | 61.57 | 65.39 |
| A02-E7 | E7 (82-90) | HLA-A*02:01 | A02 | LLMGTLGIV (SEQ ID NO: 48) | 9 | Yes | No | T000107 | 17/17-100% | None | A0201 | 7538538 | 0.5 | 16 | 29 | -0.12 | -0.31 | 98 | 97.6 |
| | E7 (82-90) | HLA-B*15:01 | B62 | LLMGTLGIV | 9 | Yes | No | T000107 | 17/17-100% | None | A0201 | 7538538 | 8 | 860.8 | 10 | -1.85 | -2.29 | 76.83 | 69.57 |
| A03-E7-1 | E7 (51-60) | HLA-A*03:01 | A03 | HYNIVTFCCK (SEQ ID NO: 49) | 10 | Yes | No | T000112 | 17/17-100% | None | DR15 | 11267969 | 2.2 | 4049.9 | 11 | -2.21 | -2.13 | 77.57 | 69.21 |
| | E7 (51-60) | HLA-A*11:01 | A03 | HYNIVTFCCK | 10 | Yes | No | T000112 | 17/17-100% | None | DR15 | 11267969 | 3.3 | 1212.9 | 11 | -1.69 | -1.62 | 79.12 | 74.39 |
| A03/A11-E7-3 | E7 (88-97) | HLA-A*11:01 | A03 | GIVCPICSQK (SEQ ID NO: 50) | 10 | Yes | Yes | T000127/L000043 | 16/17-94% | GIVCPICSRK | A11 | 9366399/7511661 | 1.35 | 109 | 19 | -1.04 | -1.28 | 88.13 | 83.87 |
| | E7 (88-97) | HLA-A*03:01 | A03 | GIVCPICSQK | 10 | Yes | Yes | T000127/L000043 | 16/17-94% | GIVCPICSRK | A11 | 9366399/7511661 | 1 | 156.6 | 24 | -1.2 | -1.54 | 92.98 | 85.04 |
| B07-B08-B35-E7 | E7 (5-13) | HLA-B*07:02 | B07 | TPTLHEYML (SEQ ID NO: 51) | 9 | No | Yes | T000136/T000140 | 17/17-100% | None | A2 | 23211628 | 1.7 | 505.2 | 20 | -0.97 | -0.98 | 88.7 | 85.75 |
| | E7 (5-13) | HLA-B*08:01 | B08 | TPTLHEYML | 9 | No | Yes | T000136/T000140 | 17/17-100% | None | A2 | 23211628 | 4.4 | 1881.9 | 17 | -1.54 | -1.58 | 84.01 | 78.11 |
| | E7 (5-13) | HLA-B*35:01 | B07 | TPTLHEYML | 9 | No | Yes | T000136/T000140 | 17/17-100% | None | A2 | 23211628 | 4.1 | 1139.5 | 20 | -1.32 | -0.58 | 87.47 | 85.25 |

TABLE 3-continued

E7 Epitopes

| Pool | Epitope Label | Position | HLA | Super-type | Sequence | Length | Epitope | Ligand | Accession Number | Conservation | Most Common HPV16-variants | Previous HLA described for | HPVdb-Reference | IEDB.bind bind | IEDB.NetMHC bind | Syf-peithi bind | IEDB.ANN bind | per-prot | total per-cent prot | per-cent tile |
|---|---|---|---|---|---|---|---|---|---|---|---|---|---|---|---|---|---|---|---|---|
| B35-E7-1 | | E7 (16-25) | HLA-B*44:02 | B44 | QPETTDLYCY (SEQ ID NO: 52) | 10 | Not Found | * | * | * | * | * | * | 4.05 | 647.1 | 12 | -0.19 | -0.1180.2 | 87.47 |
| | E7 | (16-25) | HLA-B*35:01 | B07 | QPETTDLYCY | 10 | Not Found | * | * | * | * | * | * | 0.6 | 653 | 22 | -0.2 | 0.1890.8793.54 |
| E7-Pool-2 | A02-B07-B08-B35 | E7 (7-15) | HLA-A*02:01 | A02 | TLHEYMLDL (SEQ ID NO: 53) | 9 | Yes | No | T000104 | 16/17-94% | TLHEYMLD V | B8 | 15609316 | 2.1 | 64.9 | 24 | -0.28 | -0.1692.6794.37 |
| | E7 | (7-15) | HLA-B*07:02 | B07 | TLHEYMLDL | 9 | Yes | No | T000105 | 16/17-94% | TLHEYMLD V | B8 | 15609317 | 17 | 21631.5 | 12 | -2.8 | -2.6 61.7355.34 |
| | E7 | (7-15) | HLA-B*08:01 | B08 | TLHEYMLDL | 9 | Yes | No | T000106 | 16/17-94% | TLHEYMLD V | B8 | 15609318 | 6.3 | 3016.1 | 18 | -1.95 | -1.4483.5676.75 |
| | E7 | (7-15) | HLA-B*35:01 | B07 | TLHEYMLDL | 9 | Yes | No | T000107 | 16/17-94% | TLHEYMLD V | B8 | 15609319 | 36 | 18002.2 | 11 | -2.72 | -2.7956.8851.96 |
| B08-B07-B35-B57- | E7 | (49-57) | HLA-B*07:02 | B07 | RAHYNIVTF | 9 | Yes | No | T000118 | 17/17-100% | None | A24/A0201 | 12384540 | 3.8 | 1801.2 | 9 | -0.6 | -0.7576.6580.99 |
| | E7 | (49-57) | HLA-B*08:01 | B08 | RAHYNIVTF | 9 | Yes | No | T000119 | 17/17-100% | None | A24/A0201 | 12384541 | 9 | 4103.7 | 13 | -0.95 | -1.1277.1778.33 |
| | E7 | (49-57) | HLA-B*15:01 | B62 | RAHYNIVTF | 9 | Yes | No | T000120 | 17/17-100% | None | A24/A0201 | 12384542 | 0.5 | 64.7 | 11 | 0.85 | 0.7580.8282.48 |
| | E7 | (49-57) | HLA-B*57:01 | B58 | RAHYNIVTF | 9 | Yes | No | T000121 | 17/17-100% | None | A24/A0201 | 12384543 | 0.6 | 233.8 | 14 | 0.29 | 0.2583.5388.48 |
| | E7 | (49-57) | HLA-B*35:01 | B07 | RAHYNIVTF | 9 | Yes | No | T000122 | 17/17-100% | None | A24/A0201 | 12384544 | 0.8 | 283.5 | 11 | 0.21 | 0.3580.5886.61 |
| A02-E7-2 | E7 | (85-93) | HLA-A*02:01 | A02 | GTLGIVCPI (SEQ ID NO: 55) | 9 | Yes | No | T000128 | 17/17-100% | None | A24/A0201 | 7538538 | 4.4 | 107.2 | 21 | -1.1 | -1.3789.0283.79 |
| A03/A11-E7-2 | E7 | (89-97) | HLA-A*03:01 | A03 | IVCPICSQK (SEQ ID NO: 56) | 9 | Yes | No | T000127 | 16/17-94% | GIVCPICS RK | A11 | 9366399 | 0.45 | 66.9 | 21 | -0.8 | -0.6790.3688.74 |
| | E7 | (89-97) | HLA-A*11:01 | A03 | IVCPICSQK | 9 | Yes | No | T000128 | 16/17-94% | GIVCPICS RK | A11 | 9366400 | 0.55 | 182 | 31 | -1.24 | -1.4299.7889.46 |
| A24-E7-1 | E7 | (56-65) | HLA-A*24:02 | A24 | TFCCKCDSTL (SEQ ID NO: 57) | 10 | Yes | No | T000111 | 15/17-91% | TFCCKCDF TL | DR3 | 11267969 | 4.4 | 5243 | 17 | -1.68 | -1.9281.7574.76 |

TABLE 3-continued

| | | | | | E7 Epitopes | | | | | |
|---|---|---|---|---|---|---|---|---|---|---|
| B35-E7-2 (44-53) | HLA-B*35:01 | B07 | QAEPDRAHY (SEQ ID NO: 58) | 9 | Yes | No | T000109 | 16/17-94% | QAKPDRAHY | B18 | 10940919 | 4.9 | 462.8 | 12 | 0.13-0.3380.0486.7 |
| E7 11-19 (11-19) | HLA-A*02:01 | A02 | YMLDLQPET (SEQ ID NO: 59) | 9 | Yes | No | T000125 | 16/17-94% | YMLDVQPE T | A2 | 7538538 | 0.4 | 30.4 | 21 | -0.59-0.4390.4 90.62 |
| E7 11-20 (11-20) | HLA-A*02:01 | A02 | YMLDLQPETT (SEQ ID NO: 60) | 10 | Yes | Yes | T000132 | 14/17-82% | YMLDVQPE TT | A2 | 15609329 | 1.45 | 236.8 | 19 | -1.62-1.4988.0180.55 |

TABLE 4

Cross-reactive Epitopes

| Patient | HLA | Epitope | Sequence | IC50 (ANN) | Predicted HLA |
|---|---|---|---|---|---|
| 7007 | A*68:01 | E2(267-276) | ILTAFNSSHK | 66.98 | A*03:01/A*11:01 |
|  | A*68:01 | E2(284-292) | NTTPIVHLK | 4.94 | A*11:01 |
|  | A*68:01 | E2(297-306) | TLKCLRYRFK | 182.15 | A*03:01/A*11:01 |
|  | A*68:01 | E2(37-45) | RLECAIYYK | 711.12 | A*03:01/A*11:01 |
|  | A*68:01 | E6(106-115) | LLIRCINCQK | 183.06 | A*03:01/A*11:01 |
|  | A*68:01 | E6(33-41) | IILECVYCK | 803.58 | A*03:01/A*11:01 |
|  | A*68:01 | E6(37-46) | CVYCKQQLLR | 72.47 | A*03:01/A*11:01 |
|  | A*68:01 | E6(93-101) | TTLEQQYNK | 58.08 | A*11:01 |
|  | A*68:01 | E7(51-60) | HYNIVTFCCK | 505.69 | A*03:01/A*11:01 |
|  | A*68:01 | E7(88-97) | GIVCPICSQK | 469.86 | A*03:01/A*11:01 |
|  | A*68:01 | E7(89-97) | IVCPICSQK | 72.24 | A*03:01/A*11:01 |
| 7015 | B*14:02 | E2(147-155) | VVEGQVDYY | 492.79 | A*01:01 |
|  | A*32:01 | E2(329-337) | KSAIVTLTY | 50.93 | A*01:01/A*03:01/A*11:01/B*15:01/B*35:01/B*57:01 |
|  | A*11:01 | E6(68-77) | AVCDKCLKFY | 219.88 | A*11:01 |
| 7019 | A*68:01 | E2(103-112) | LTAPTGCIKK | 85.73 | A*03:01/A*11:01 |
|  | A*68:01 | E2(284-292) | NTTPIVHLK | 4.94 | A*11:01 |
|  | A*68:01 | E2(297-306) | TLKCLRYRFK | 182.15 | A*03:01/A*11:01 |
|  | A*68:01 | E6(106-115) | LLIRCINCQK | 183.06 | A*03:01/A*11:01 |
|  | A*68:01 | E6(37-46) | CVYCKQQLLR | 72.47 | A*03:01/A*11:01 |
|  | A*68:01 | E6(93-101) | TTLEQQYNK | 58.08 | A*11:01 |
|  | A*32:01 | E7(85-93) | GTLGIVCPI | 12.13 | A*02:01 |
| 7027 | A*03:01 | E6(93-101) | TTLEQQYNK | 492.96 | A*11:01 |
| 7030 | A*03:01 | E6(93-101) | TTLEQQYNK | 492.96 | A*11:01 |

Within the 59 candidate HPV16-peptides, E2 had the lowest number of previously defined CTL-epitopes (3/24, 12%), while E6 and E7 had higher number of previously described CTL-epitopes (35% and 46% respectively). The number of predicted HPV16-peptides ranged from 15 peptides (A*02:01), to 0 peptides (B*40:01, B*44:02) among the selected HLA-alleles (FIG. 1A). To determine if lack of HLA-binding motifs in the 3 HPV-antigens can poise specific HLA-alleles as risk-factors for HPV+ HNSCCs, odds-ratio of HLA-allele frequencies in HPV+ HNSCCs (N=77) were calculated and compared to HPV- HNSCCs (N=64). HLA B*40:01, which had no predicted HPV16-peptides for E2, E6 and E7 had an odds-ratio of 7.48 compared to HPV-HNSCCs (FIGS. 1A-1B; P=0.059), and had poor-binding peptides for all HPV16-antigens (bottom 20th percentile compared to other HLAs; FIG. 1K) (Summary of strong HLA-binders from all HPV16-genes for TCGA-UM patient HLA-alleles not shown but available upon request; binding affinities for HLA-alleles from TCGA/UM cohort using ANN for all HPV16-genes, related to FIG. 1A and FIG. 1K, also not shown but available upon request). HLA-alleles A*24:02, B*07:02, and B*51:01 were also overrepresented (OR>=2) in HPV+HNSCCs, although they were not statistically significant. Of note, HLA-B*07:02 (OR=2, FIG. 1B), has been previously reported to be associated with poor clinical outcome in cervical cancer and escape HPV-specific T-cell (HPV-CTL) recognition. These results point to the importance of CTL-mediated control of HPV16 malignancies.

Figure 1G:
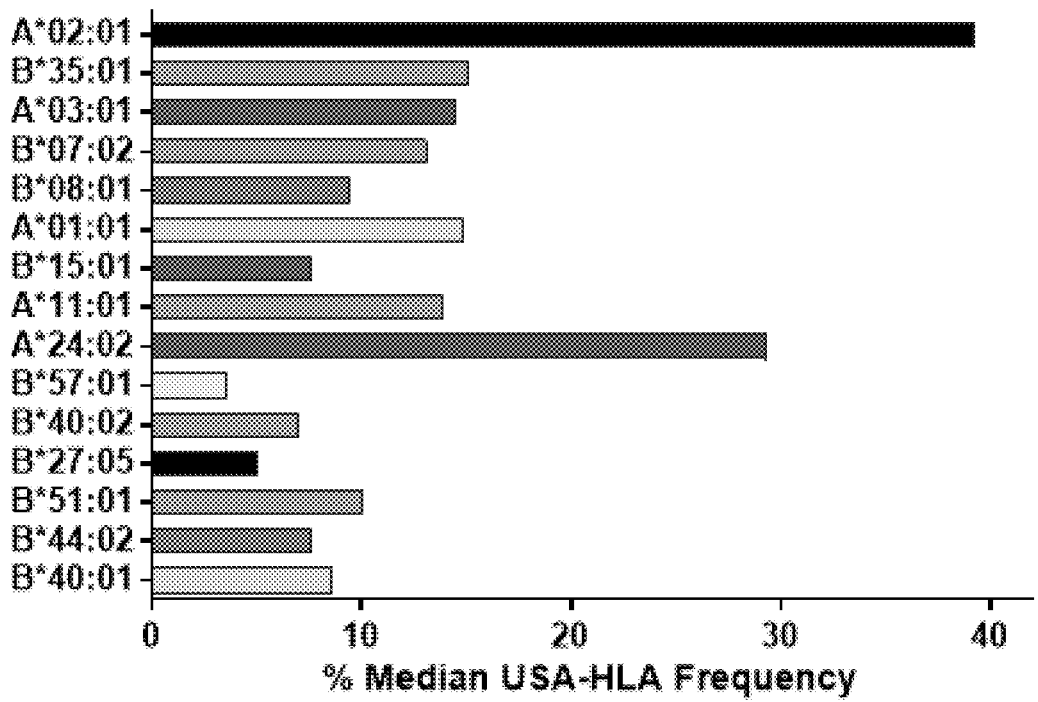
Figure 1H:
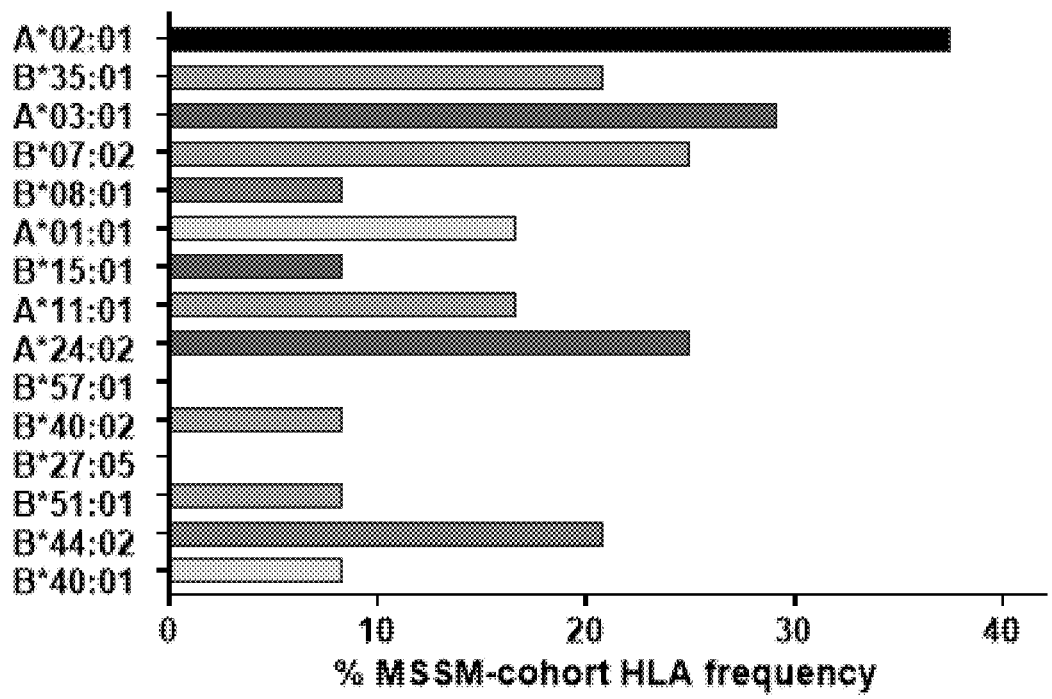
Figure 1I:
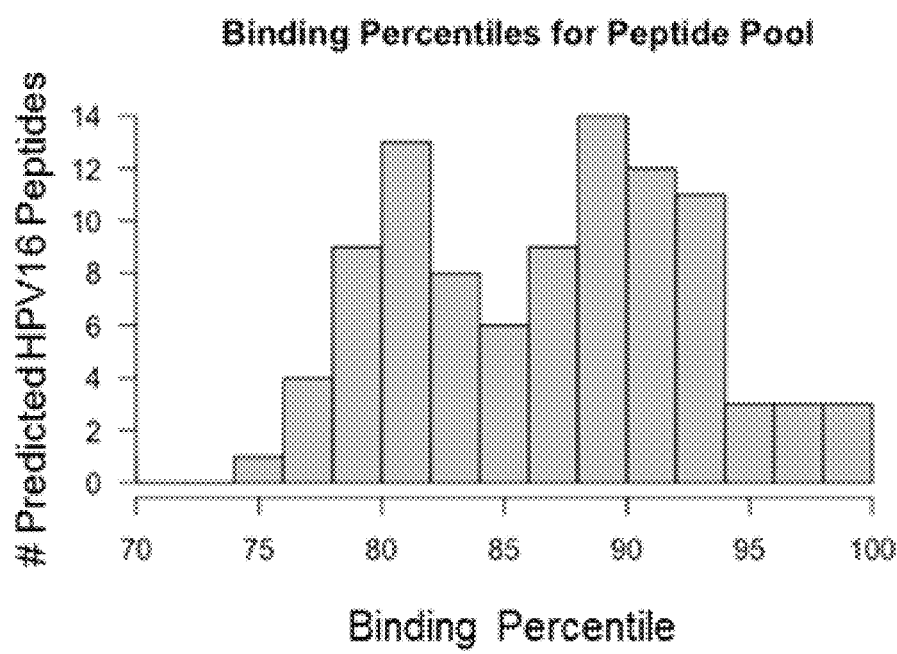
Figure 1J:
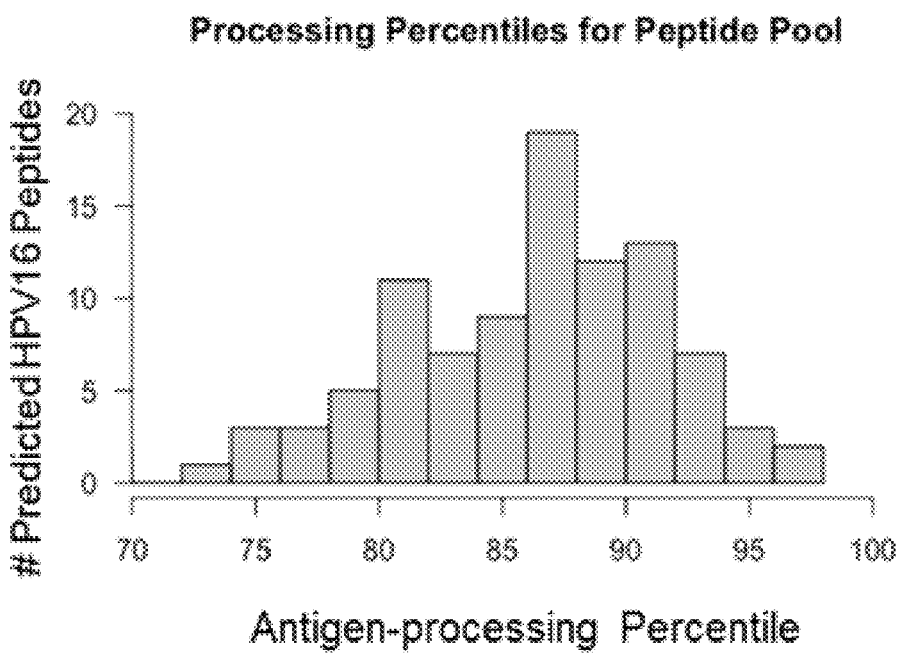
Figure 1L:
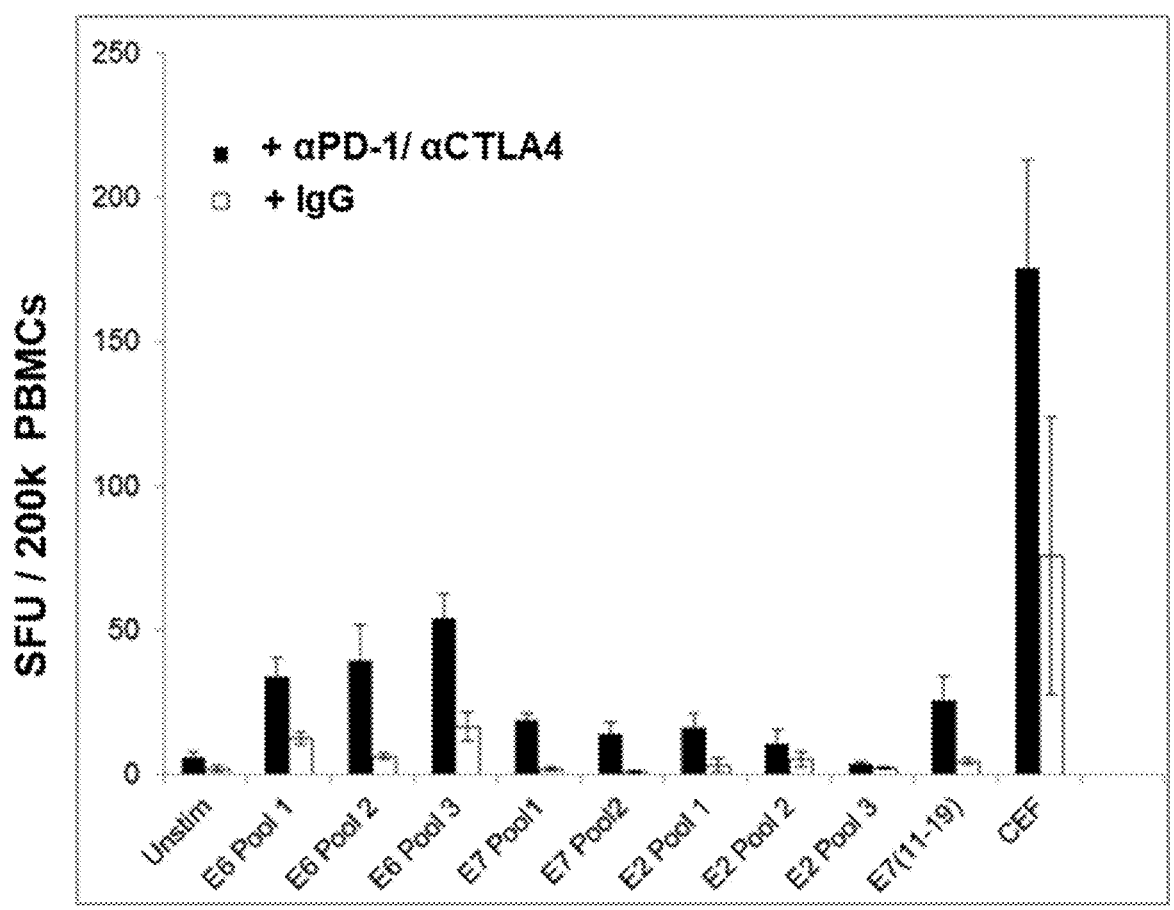
Figure 6A:
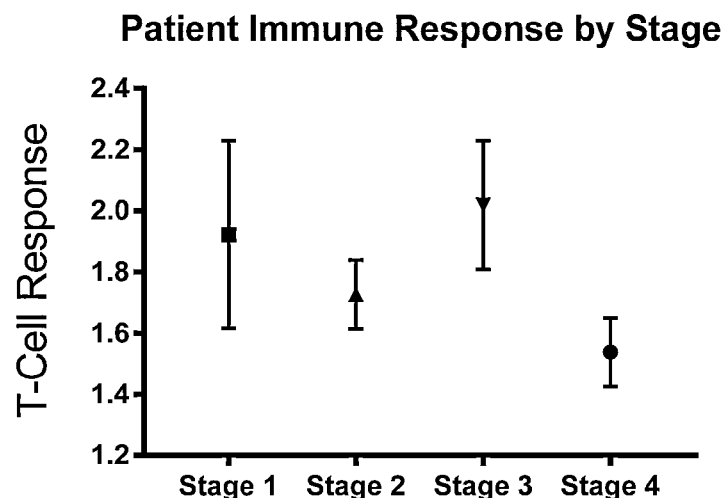
FIGS. 6A-6B show HPV-CTL responses in MSSM patients by tumor stage and age of diagnosis. HPV-antigen stimulated CTLs from HPV+HNSCC patients (N=18) after ex vivo stimulation classified by tumor stage (FIG. 6A) and age at time of diagnosis (FIG. 6B) with respect to T-cell response (Log scale).
Figure 6B:
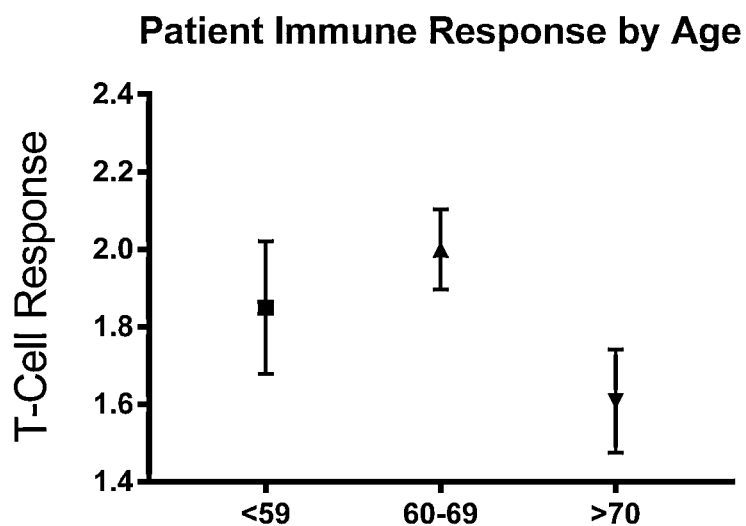
Figure 9:
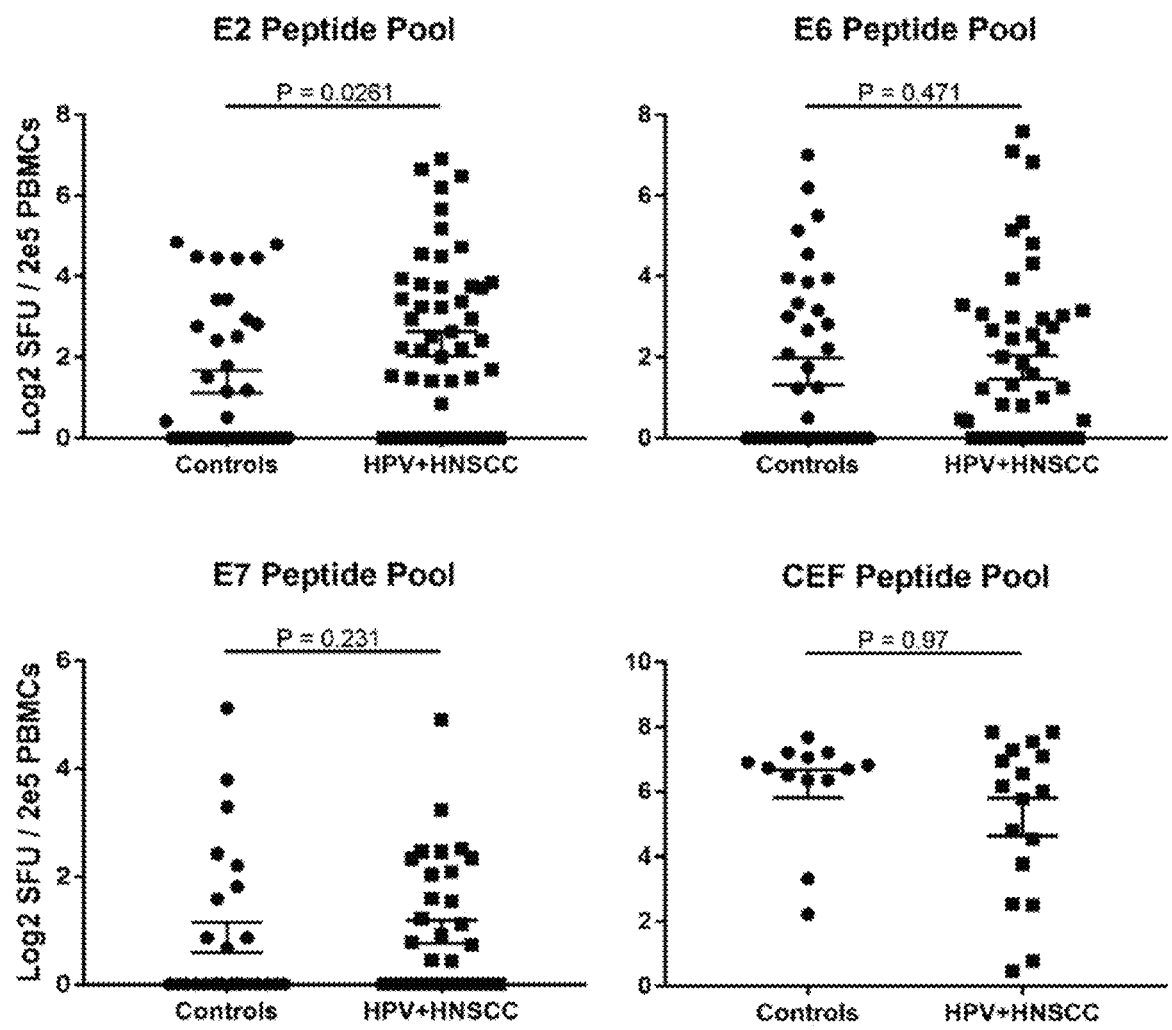
FIG. 9 shows a summary of CTL-reactivity in HPV+ HNSCC samples and healthy controls. Predicted HPV16-peptides were pooled according to antigen and tested for CTL reactivity by IFNγ Elispot. P-values from Wilcoxon rank-sum test are shown. CEF—Positive CTL-epitopes pool from CMV, EBV, Flu.

Because HPV-CTLs in peripheral blood mononuclear cells (PBMCs) are not abundant, PBMCs stimulated for 10 days were used with candidate peptides and CKB antibodies αCTLA4 and αPD-1 to enhance HPV-CTL reactivity (FIG. 1L). HPV-CTL frequency in PBMCs between HPV+ HNSCC patients (N=18) and healthy controls (N=14) were compared by interferon gamma (IFNγ) Elispots using anti-gen specific peptide pools (FIGS. 1C-1D and FIG. 9; Tables 1-4). The HLA-frequency distribution of this cohort largely mirrored median HLA-frequency distribution in the USA (FIG. 1H). IFNγ responses against HPV16-E2 were substantially more common (>3-fold higher) in HPV+ HNSCC PBMCs compared to healthy control PBMCs (Unpaired Welch's T-Test, P=0.012, FIG. 1C and FIG. 9). Moderate to high E6-reactivity was observed in HPV+ HNSCC patients (1.5 fold higher in HPV+ HNSCCs), while E7-reactivity was generally low (FIGS. 1C-1D and FIG. 9). To determine if PBMC T-cell reactivity correlates with B-cell immunity, IgG serologic responses to the E2, E6, and E7 antigens in the 18 patients were measured. E2 and E7-specific serum IgG titers were higher relative to E6 (>2-fold, P<0.05) in the patients (FIG. 1E). The majority of patients who had IgG to E2, E6 and E7 also had a measurable CTL response (E2=72%, E6=60%, E7=70%, respectively, FIG. 1F). There was strong concordance between seroreactivity and T-cell reactivity within same antigens (Chi-squared independence test, P=0.03). Lastly, a modest trend towards decreased HPV CTL-response with advanced age and tumor stage of the patient but these were not statistically significant (FIGS. 6A-6B). These results indicate that E2 and E6 antigens are more CTL-reactive than E7 in HPV+ HNSCC patients, and HPV-CTL response can be enhanced by CKB antibodies.

Mapping immunodominant epitopes of HPV16 E2, E6 and E7 in HPV+ HNSCCs. To identify novel CTL epitopes from E2, E6 and E7, a second IFNγ Elispot analysis was performed using individual predicted HPV16-peptides against patient-specific HLA-alleles (FIG. 2A). 51 out of 59 predicted peptides elicited a T-cell response in at least one patient, indicating a high degree of success (86%) of the prediction-validation strategy (FIG. 2A; Tables 1-4). Consistent with pooled-antigen Elispot results (FIGS. 1C-1D), sub-dominant E7-specific CTL-reactivity was observed relative to E2, E6 epitope-specific CTL-responses (FIG. 2A).

Figure 2E:
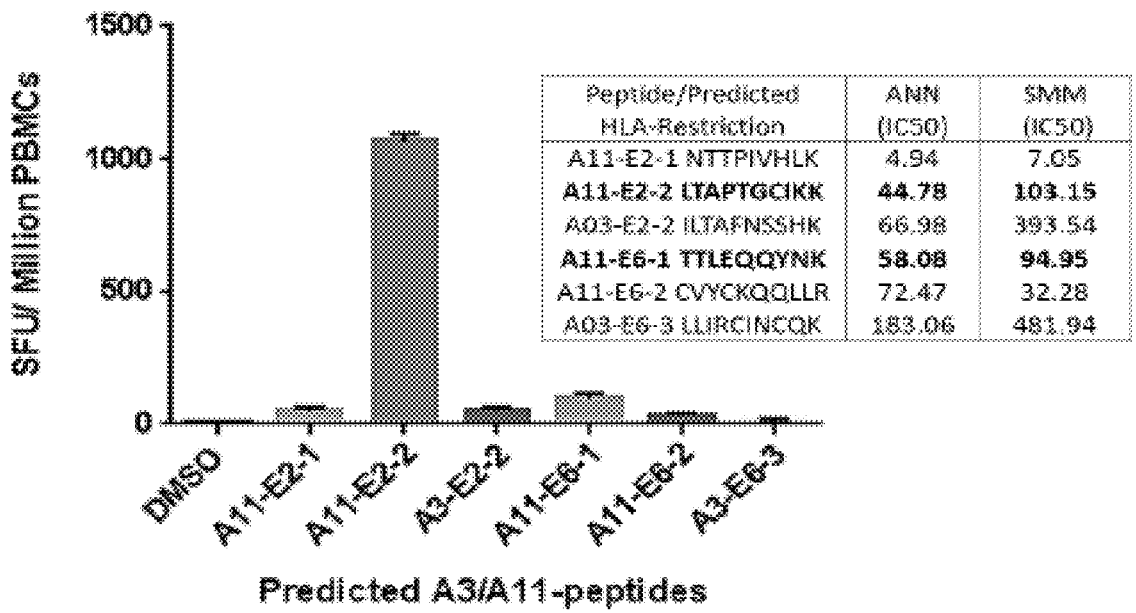
Figure 2F:
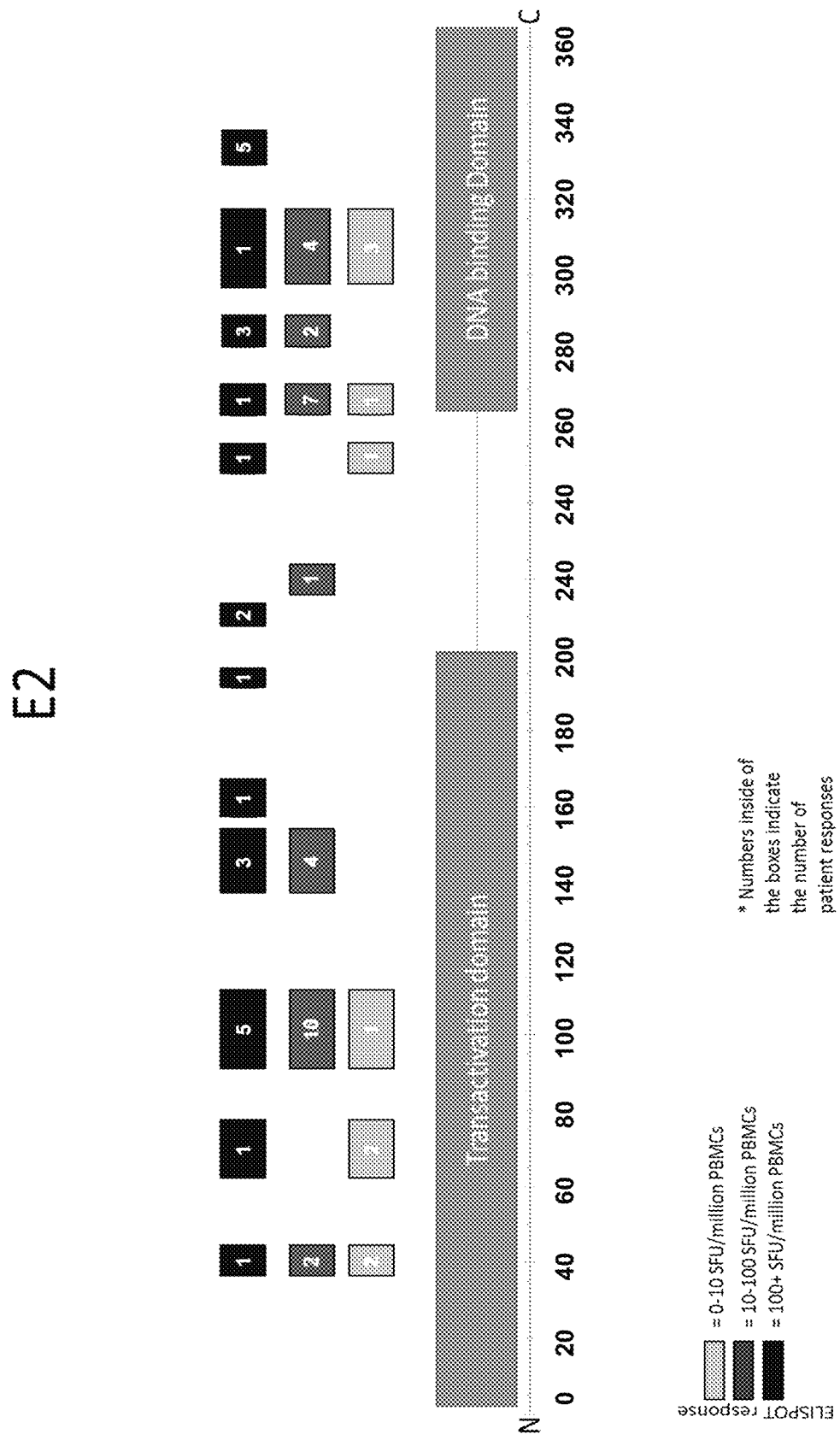
Figure 2G:
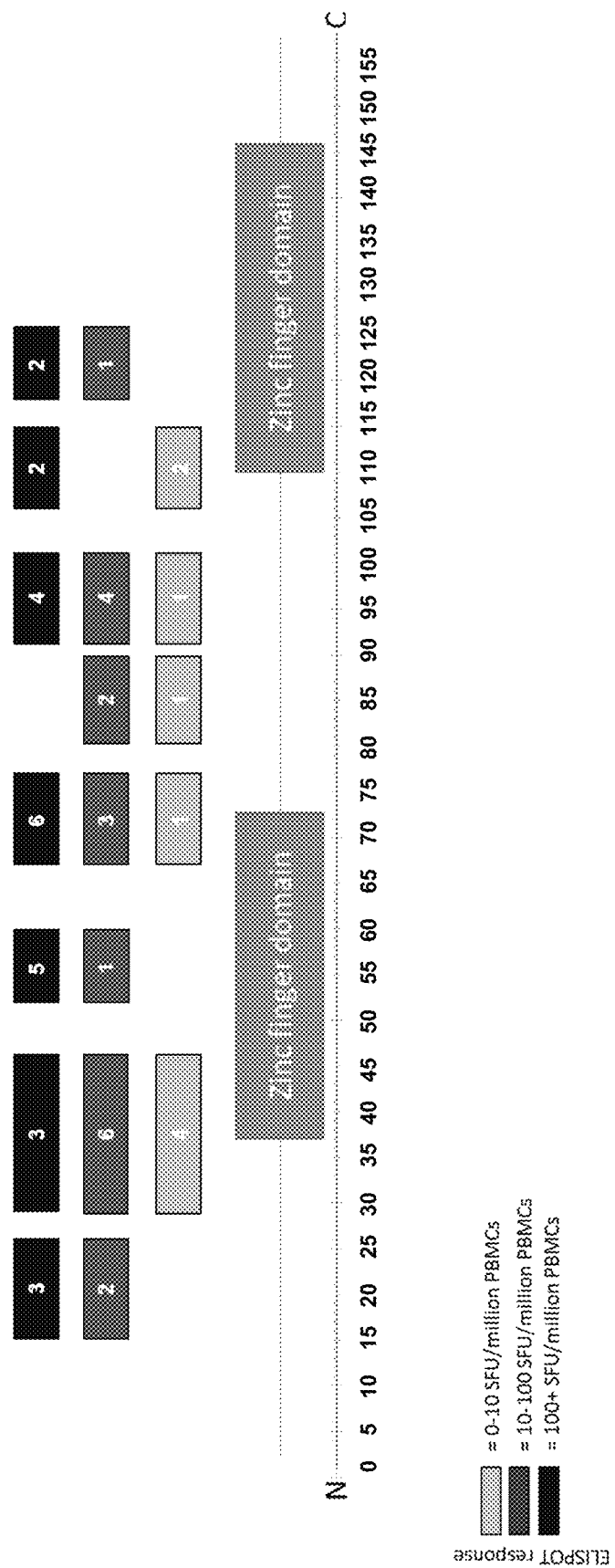

Sixteen epitopes had an average response frequency of >=100 mean spot forming units (SFUs)/10$^6$ PBMCs and were classified as strongly immunogenic (see, e.g., FIGS. 2B-2E; Tables 1-4). Twenty nine CTL-epitopes had an average response frequency between 10-100 SFU/10$^6$ PBMCs (moderately immunogenic), while 6 epitopes had an average response frequency<10 SFU/10$^6$ PBMCs (low immunogenic). The majority of moderate to highly immunogenic epitopes (77%) were novel, or had not been described with the observed HLA restriction (FIGS. 2B-2E; Tables 1-4). Sixteen unique epitopes that elicited a cross-reactive response to other alleles were observed within the same supertype supporting the strategy for HLA-supertype based epitope prediction (Tables 1-4). FIG. 2E shows a representative example, where an HLA-A*11:01 restricted E2-peptide had strong predicted binding affinity and elicited strong CTL-reactivity to HLA-A*68:01 (A3 supertype). Within the E2 antigen, most CTL-epitopes (52%) were clustered within the trans-activating DNA-binding domain, 23% in the hinge region, and 24% in the DNA-binding domain (FIG. 2F). Within E6, the immunodominant regions (70% of epitopes) encompassed amino acids 37-109 with 40% of epitopes arising in the first zinc finger domain (FIG. 2G). Interestingly, the zinc finger domain of E7 also had 42% of the CTL-epitopes (FIG. 2H).

HPV16 E2, E6 & E7 epitope distribution and immunogenicity in HPV+HNSCCs. FIG. 1 presents the analysis of CTL epitopes in HPV+HNSCC from HPV16 E2, E6, and D7 antigens. FIG. 1A shows the distribution of 59 predicted HPV16-peptides by each HLA-allele ranked from highest to lowest and FIG. 1B illustrates the odds-ratio of frequency distribution of each HLA-allele from FIG. 1A in HPV+ HNSCC patients (N=77) compared to HPV− HNSCC patients (N=64) *P=0.059. The predicted HPV16-peptides were pooled according to antigen (FIG. 1C; Tables 1-4) and tested for CTL-reactivity by IFNγ elispots. P-values from Unpaired Welch's T-test are shown. FIG. 1D is a representative example of a CTL-reactivity analysis from one HPV+ HNSCC PBMC. The quantified SFUs after background subtraction are shown in the left panel alongside the image results, done in triplicate. A rapid-ELISA test screening shows the seroreactivity of the HPV16-E2, E6, E7 antigens in HPV+HNSCC MSSM patients (FIG. 1E). FIG. 1F illustrates the seroreactivity and CTL-reactivity concordance for each HPV-antigen in responding HPV+HNSCC patients. Sizes of the circles are proportional to the number of responding HPV+HNSCC patients for each antigen.

FIGS. 1G-1J show the HLA Allele-Frequencies and predicted Scores of Candidates. FIG. 1G depicts the median USA HLA-allele frequencies that were obtained from Allele frequency net database. In FIG. 1H, the HLA-allele frequency distributions of MSSM-cohort are shown. The distribution of 59 predicted HPV16-peptides are binned according to total binding (FIG. 1I) percentile scores and according to total antigen-processing percentile scores (FIG. 1J). The distribution of all HPV16-predicted binding 9-11mer peptides from all 8 HPV16-antigens (IED-consensus IC50<500 nM) for HLA-A, B alleles in TCGA+UM cohort (n=694 peptides) is ranked by decreasing number of total predicted peptides per each allele (FIG. 1K). HLA-B*40:01 is shown in red. A pareto line representing cumulative distribution of peptide frequencies is shown as dashed line. The results from an assessment of ex vivo PBMC stimulation protocol (FIGS. 1-2) after 10 days with αPD1+αCTLA-4 blocking antibodies on day 1, compared to purified isotype IgG day 1 in healthy donor is shown in FIG. 1L.

Landscape of CTL-epitopes from HPV16 E2, E6 and E7 in HPV+HNSCCs. HPV+HNSCC PBMCs from the initial pooled antigen screen (FIG. 1C), were tested against individual HPV16-predicted peptides corresponding to the patient HLA-type. FIG. 2A is a summary of ELISPOT epitope deconvolution screen showing all responding HPV+ HNSCC patients (each column) against tested HPV16-peptides (each row) in log scale. Within each antigen, peptides are ranked from most number of CTL responses (top) to the least (bottom). The results for examples of individual responding patients after background subtraction are presented in FIGS. 2B-2D, B-HLA-A*02:01+ patient; C-HLA-A*02:01/B*07:02+ patient; and D-HLA-A*24:02/B*35:01+ patient, respectively. HPV16-peptides predicted for the HLA-A3-supertype can stimulate a CTL response to a representative allele (A*68:01, FIG. 2E). Each peptide label indicates the HLA-allele from which the peptide was originally predicted. The inset shows binding affinities for predicted peptides for A*68:01 were determined and positive responders are shown in bold (FIG. 2E, inset). *P<0.1, **P<0.01, Unpaired two-tailed Welch's T-test. FIGS. 2F-2H depict the defined immunodominant regions of HPV16-E2, E6 and E7, respectively. All immunogenic CTL-epitopes identified in this study mapped onto the 3 HPV16-antigens. Protein domain information shown in blue was obtained from PAVE. The strength of immune response in the regions tested is indicated by the shaded boxes corresponding to various levels of the ELISPOT response as indicated in the legend. The numbers inset into the response box of each tested region indicate the number of unique HPV+HNSCC MSSM patient-specific responses.

Example 2

Figure 7A:
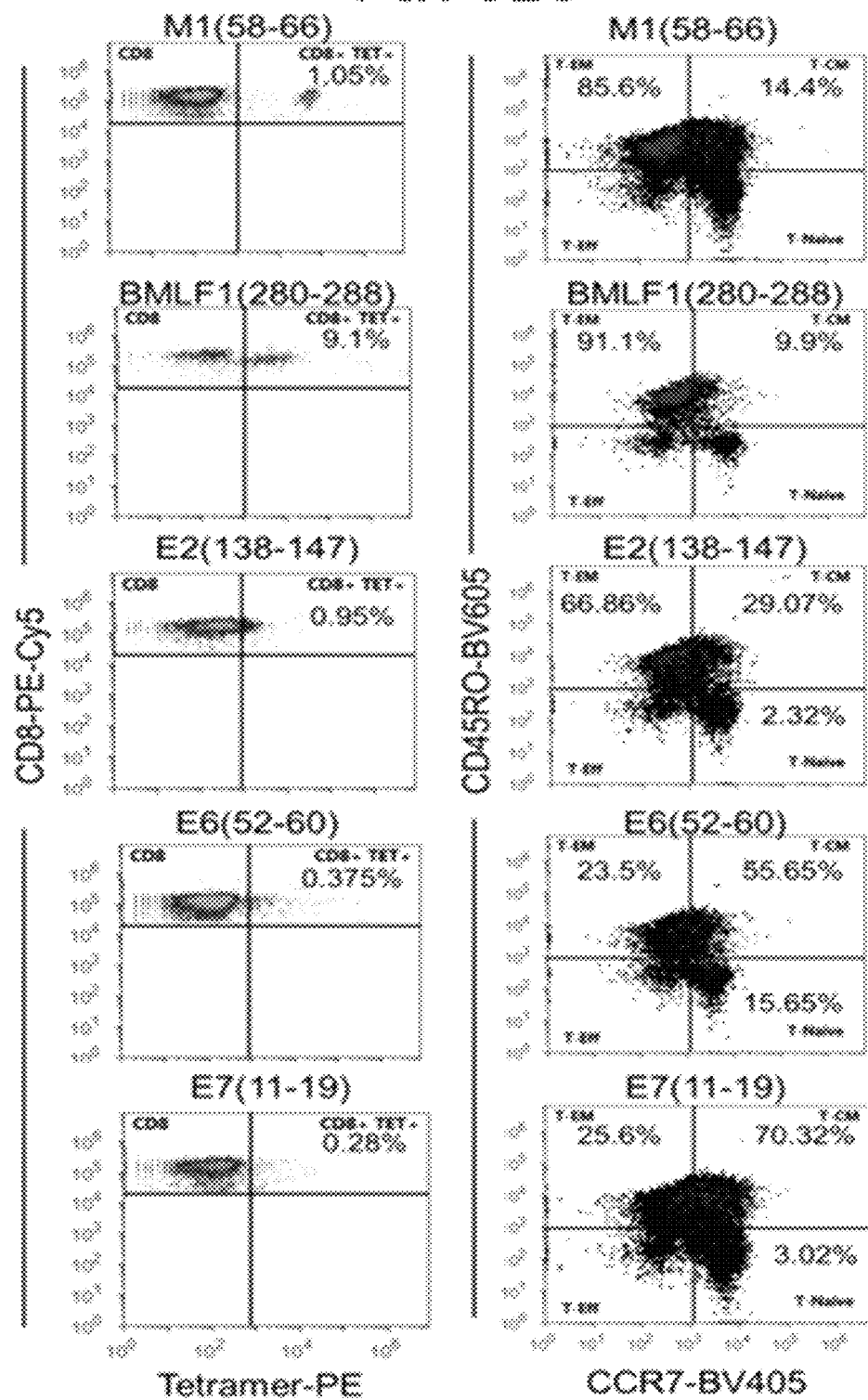
FIGS. 7A-7C show HPV-CTLs in HPV+HNSCC patients are present in the memory compartment. Memory phenotyping of HPV-antigen specific CTLs from HPV+HNSCC patients after ex vivo stimulation. Representative examples from two patients (FIG. 7A (Pt. 7028), FIG. 7B (Pt. 7012)) are shown. Chronic antigen (BMLF1) specific CTLs show increased $DP^{Ex}$ dysfunctional phenotypes compared to acute antigen (FluM1) CTLs (FIG. 7C). CTLs were stimulated for representative HPV+HNSCC patient 7002, and total, antigen-specific CTLs were $DP^{Ex}$-phenotyped for FluM1 (top panel) and BMLF1 (bottom panel) CTLs. Total CD8+ phenotypes is shown in black; back-gated CD8+Multimer+ phenotypes are shown in red. % indicate CD8+ Multimer+ events in each gate.
Figure 7B:
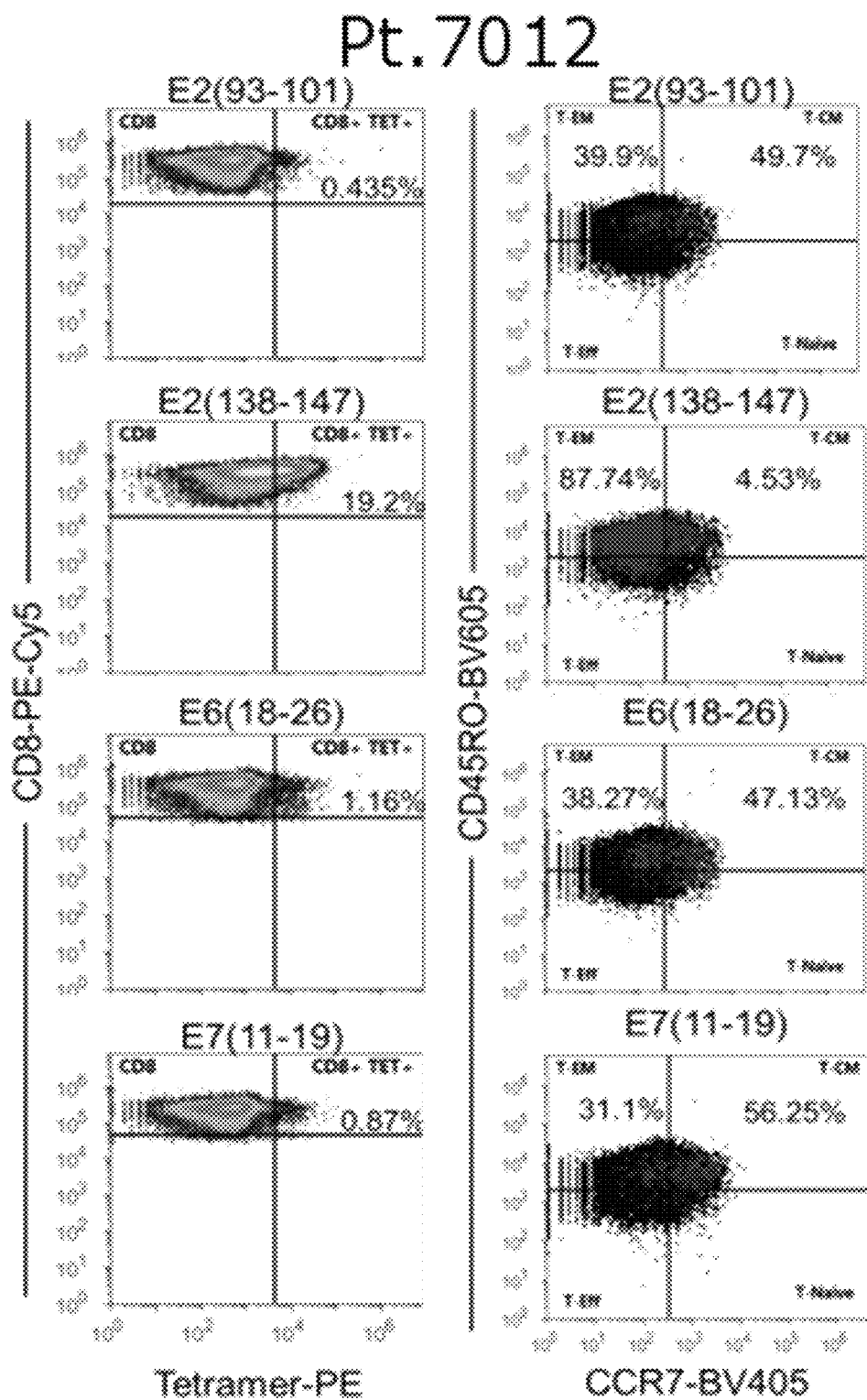

HPV-specific T-cells exhibit dysfunctional phenotype in HPV+ HNSCC patients. The first set of studies interrogated whether responding ex vivo stimulated HPV-specific peripheral CTLs in HPV+HNSCC patients were in naive or memory T-cell compartments. After one round of ex vivo stimulation by autologous antigen-presenting cells (APCs) presenting cognate HPV16-antigen, the majority (>79%) of HPV-specific CTLs detectable by antigen-specific multimers in HLAA*02:01+ patients exhibited memory phenotype distributed between Effector Memory (TEM, CD45ROhiCCR7lo) and Central Memory (TCM, CD45ROhiCCR7hi) compartments (representative examples in FIGS. 7A-7B).

While CTL dysfunction in chronic viral infections and cancers has been described, few studies have focused on the extent of T-cell exhaustion in HPV+HNSCC patients because of the difficulties in studying low-frequency HPV-CTLs. HPV-CTL dysfunction was assessed in HPV+HNSCC patients after ex vivo stimulation by autologous antigen-presenting cells (APCs) presenting cognate HPV16-antigen in the absence of CKB antibodies. The rationale included that activated HPV-specific PD1+ CTLs that are poised towards the exhaustion spectrum will become further dysfunctional after APC-stimulation and acquire additional inhibitory markers characteristic of profound dysfunction, such as CD39 and TIM-3.

Figure 7C:
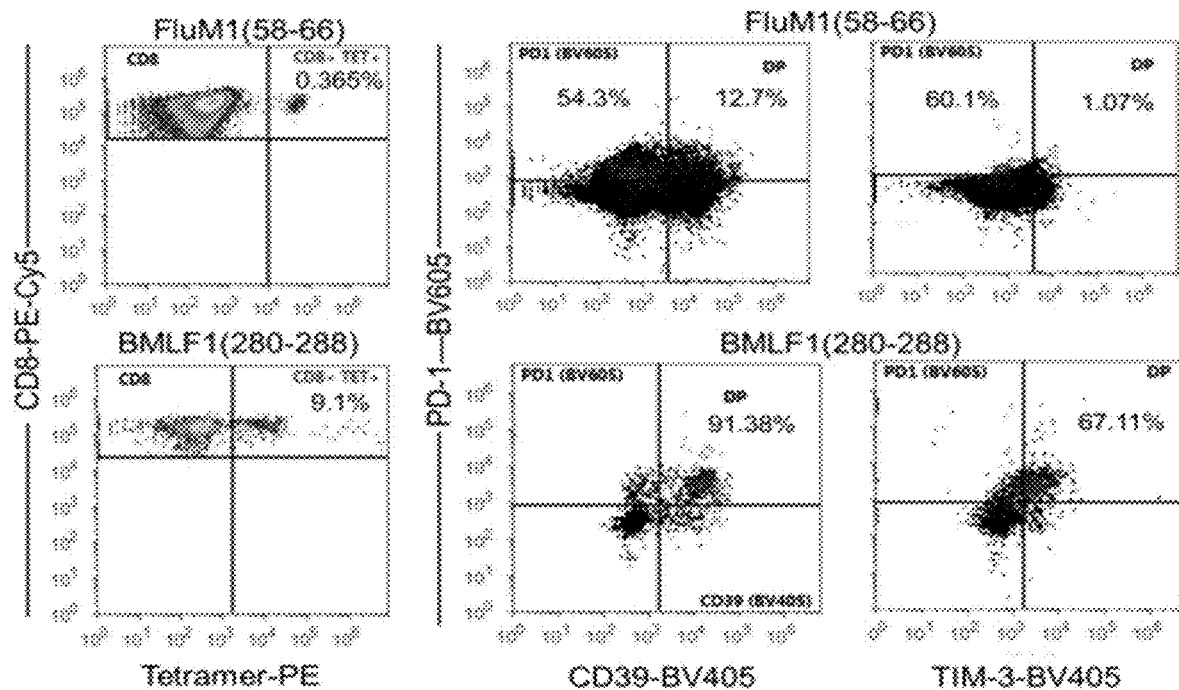

Chronic EBV-BMLF1 antigen specific HLA-A*02:01-restricted CTLs compared to acute Flu-M1 antigen specific CTLs, displayed a substantially higher DPEx-phenotype (CD39+PD-1+ 7.5 fold, TIM-3+PD-1+ 67-fold) indicating the validity of this approach (FIG. 7C). In four HLA-A*02:01+ patients with HPV-specific CTLs detectable by antigen-specific tetramers (FIGS. 3A-3C), and one HLA-A*68:01+ patient where CD137-positivity defined HPV-CTLs, total CD8+ and E2, E6 and E7-specific CTLs were phenotyped exhibiting CD8+CD39+ PD-1+ or CD8+TIM-3+ PD-1+ phenotype (DPEx-phenotype), indicating substantial exhaustion. As shown in the representative example Pt.7002, two weeks after stimulation, E2-CTLs were higher in frequency than E6 and E7-CTLs (FIGS. 3A-3B). Within the HPV16-antigens in Pt.7002, CTLs stimulated with E7-transfected APCs exhibited the highest levels of CD8+DPEx fold-change relative to mock-antigen transfected (2-4 fold; FIG. 3B) followed by E2 (1-3 fold; FIG. 3B) and E6 respectively. In 3/5 HPV+ HNSCC patients, total CD8+ DPEx and HPV-specific CD8+DPEx cells were higher in CTLs stimulated with E7-antigen (between 2-10 fold) relative to E2/E6 antigen-stimulated CTLs (Pts. 7002, 7007, 7012, FIGS. 3B-3C, Unpaired Welch's T-test, P<0.1), independent of HLA-status (e.g., HLA-A*68:01+ Pt. 7007) (FIG. 3C). In the other two patients, E2-CD8+DPEx was higher than E7-CD8+DPEx (2-3 fold, Pts. 7035, 7050, FIG. 3C, Unpaired Welch's T-test, P<0.1), indicating heterogeneity in HPV-specific CTL-dysfunction in HPV+ HNSCC. Interestingly, compared to E2 and E7-CTLs, E6-CD8+DPEx remained relatively low in most patients, and there was an inverse relationship within patients between E7-CD8+DPEx and E2/E6-CD8+DPEx (FIG. 3C). Unsupervised hierarchical clustering of DPEx-frequencies of total CD8+ as well as HPV-specific CD8+ T-cells revealed this trend where high E2-CD8+DPEx and E6-CD8+DPEx co-occurred in patients who had relatively lower E7-CD8+DPEx and vice versa (Tukey's multiple comparisons test, E2 vs. E7, P=0.014, E6 vs. E7, P=0.084, E2 vs. E6, P=NS) (FIG. 3D). These results indicate that in most HPV+ HNSCC patients, E7-CTL dysfunction is distinct and might be either temporally or mechanistically unrelated to E2/E6 CTL-dysfunction.

HPV16-antigen load correlates with T-cell exhaustion. To provide a broader analysis of immune dysfunction from the tumor side in HPV+ HNSCCs, immune signature analysis was performed of publicly available HNSCC transcriptomes (TCGA, UM-cohorts N=119, 51 HPV+, 68 HPV−). Previously-validated immune signatures were used representing tumor infiltrating immune cell subsets and performed single-sample gene set enrichment analysis to score the HPV+ and HPV− subsets. HPV+HNSCC patients in general had higher immune infiltration scores compared to HPV−HNSCCs (FIG. 4D), with 36/51 (70%) of HPV+ HNSCC samples represented in the T-cell-high gene cluster, and few HPV+ HNSCC samples (17%) with very low immune cell infiltration scores, confirming and expanding the findings in previous studies. (Gene signatures for ssGSEA used in the present disclosure not shown but available upon request; HPV-gene sets and immune signatures for immunogenomic analyses also not shown but available upon request.)

To assess the impact of HPV gene expression on immune cell infiltration, the Spearman correlation coefficients were calculated among ssGSEA scores for the entire gene sets across all patients, including HPV16 genes and performed an unsupervised clustering on the correlation matrix (FIG. 4A). HPV16-gene signatures formed a distinct module, correlating best with cytotoxic T-cell infiltration (CYT, Cytotoxic), B-cells, regulatory T-cell signatures (TIL, Treg), and dysfunctional T-cell signatures (Exhaustion, TIGIT signatures) (FIG. 4A). Interestingly, HPV-gene signatures also negatively correlated with neutrophils and other myeloid gene signatures, indicating that lymphocytes dominate the immune landscape of HPV+ HNSCCs (FIG. 4A; FIG. 4D). A previously described exhaustion gene set correlating with HPV-gene sets in this module was also observed (Spearman $\rho$=0.33; FIG. 4A). Unsupervised hierarchical clustering on expression levels of constituent genes within the exhaustion gene set revealed three main groups with low (L), moderate (M), and high (H) expression of immune regulatory gene expression within HPV16+HNSCC patients (FIG. 4B). Individual HPV16-gene expression was analyzed in the HPV16+HNSCC tumors (N=40) stratified into Exhaustion-high (EX-H) and Exhaustion moderate/low tumors (EX-ML) (FIG. 4C). EX-H HPV16+HNSCC tumors had higher gene expression of E1, E2, E4, E6 and L2 genes compared to the EX-ML subset (FIG. 4C; Unpaired Welch's T-test; E1, E2, P<0.01; E4, E6, L2, P<0.1). E7-expression was comparably high in both the subsets, while E5 known to down-regulate MHC-class I expression, remained low in the EX-H subset (FIG. 4C). These computational analyses along with previous experiments (FIG. 3) suggest that HPV-specific CTLs have T-cell exhaustion at tumor sites, driven by intra-tumoral HPV-antigen expression.

HPV16-specific T-cells acquire dysfunctional phenotype upon ex vivo stimulation. FIG. 3A shows representative flow cytometry plots from an HLA-A*02:01 HPV+HNSCC patient T-cells stimulated with autologous APCs transfected with cognate antigen. The top panel shows the detection of HPV16-Tetramer+ CD8+ T-cells with the percentages indicating tetramer+ events within the CD8-gate for the HPV16-eptiope indicated in top label. The bottom panel shows the detection of CD8+PD1+CD39+ (in black) or CD8+Tetramer+PD1+CD39+ (DP-phenotype, back gated in red). Percentages shown indicate back-gated CD8+Tetramer+DP. FIG. 3B is the quantification of total and HPV-CTL dysfunction. In the top left, each data point is a HPV16-epitope-specific tetramer from the CD8+ tetramer+ events from the 3 different HPV16-antigens. The fold change in total CD8+ DP % after CTL-stimulation with HPV16-antigen transfected APCs, compared to mock transfected APCs is represented in the top right panel. The lower panels are the percent total CD8+DP (left) and the percent CD8+Tetramer+ DP (right). FIG. 3C summarizes the percent Total CD8+DP (top) and the percent CD8+Tetramer+DP for all except Pt. 7007 (% CD8+CD137+DP) (bottom) for dysfunction experiments in 4 other HPV+HNSCC patients. Statistics were determined using an unpaired two-tailed Welch T-test as indicated in FIGS. 3B-3C, *P<0.1, P<0.01, *P<0.001. Unsupervised hierarchical clustering of the percent DP results from E2, E6 and E7 total CTLs (left) and HPV-specific CTLs (tetramer+, CD137+, right) for all five patient analyzed (indicated on the right). The percent DP was Z-normalized across the patients.

T-cell exhaustion signatures correlate with HPV16-antigen expression. 119 HNSCC transcriptomes (68 HPV−HNSCCs and 51 HPV+HNSCCS), were analyzed for immune cell infiltration by ssGSEA. In FIG. 4A, a clustered correlation matrix of immune signatures with HPV-gene sets (HPV—All 8 HPV genes; HPV.Early—E1, E2, E4, E5; HPV.Onco—E6, E7) is shown. (All gene sets are not shown but available upon request.) Gene set correlations (FIG. 4B) were clustered by hierarchical clustering creating distinct modules (L-low exhaustion; M-moderate; H-high exhaustion) for the 49 genes in the exhaustion gene set in HPV+ HNSCC. FIG. 4C extracts HPV gene levels ($Log_2$-transcripts per million TPM)) in 40 HPV16+HNSCCs from FIG. 4B and classifies them into exhaustion high (EX-HI in main text, N=15) and exhaustion low+moderate subsets (EX-ML in main text, N=25). Statistics were determined using an unpaired two-tailed Welch T-test as indicated, *P<0.1, **P<0.01. FIG. 4D is the unsupervised hierarchical clustering of validated normalized immune signatures in 119

HNSCC transcriptomes (TCGA+UM cohorts) by ssGSEA. Each column represents one HNSCC patient tumor ssGSEA scores. Four named clusters are indicated along the bottom with the number and percentages of HPV+HNSCCs found in each cluster.

Example 3

Figure 5F:
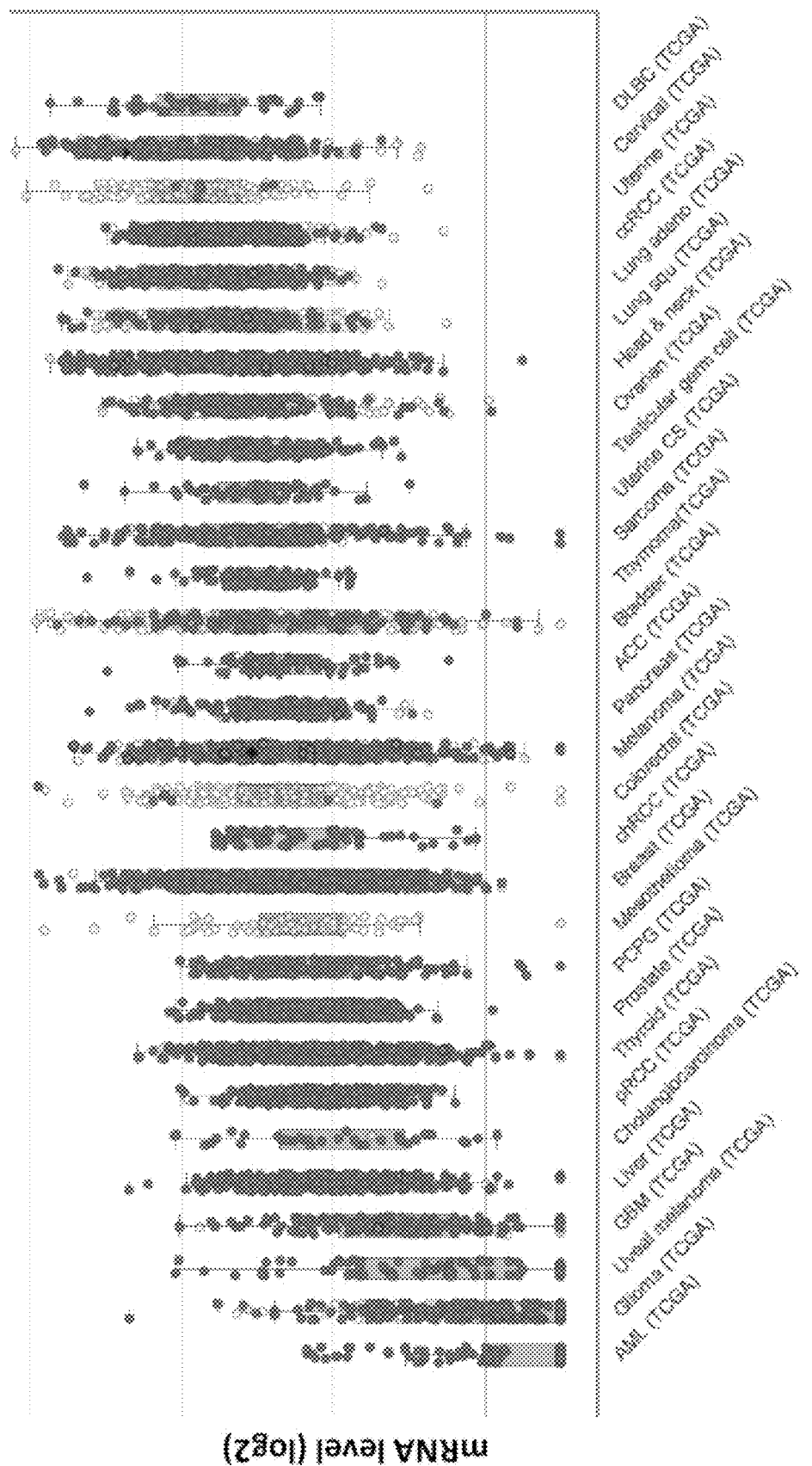
Figure 5G:
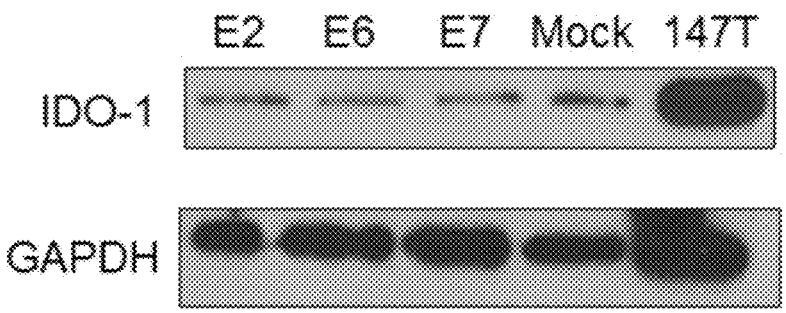
Figure 5H:
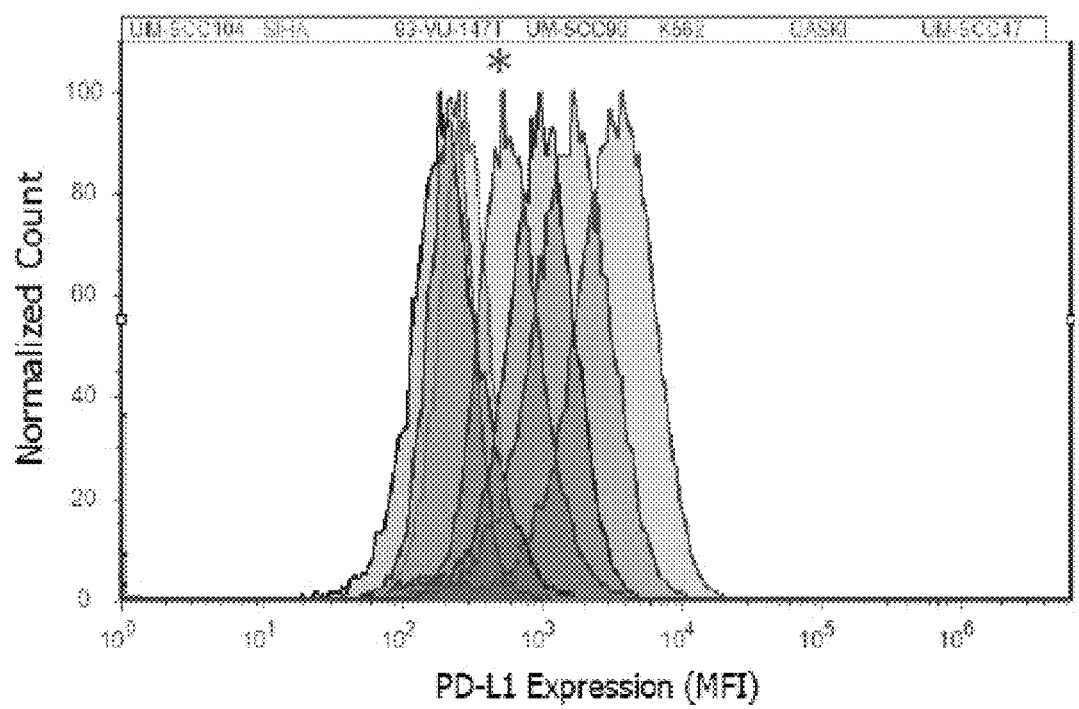
Figure 8A:
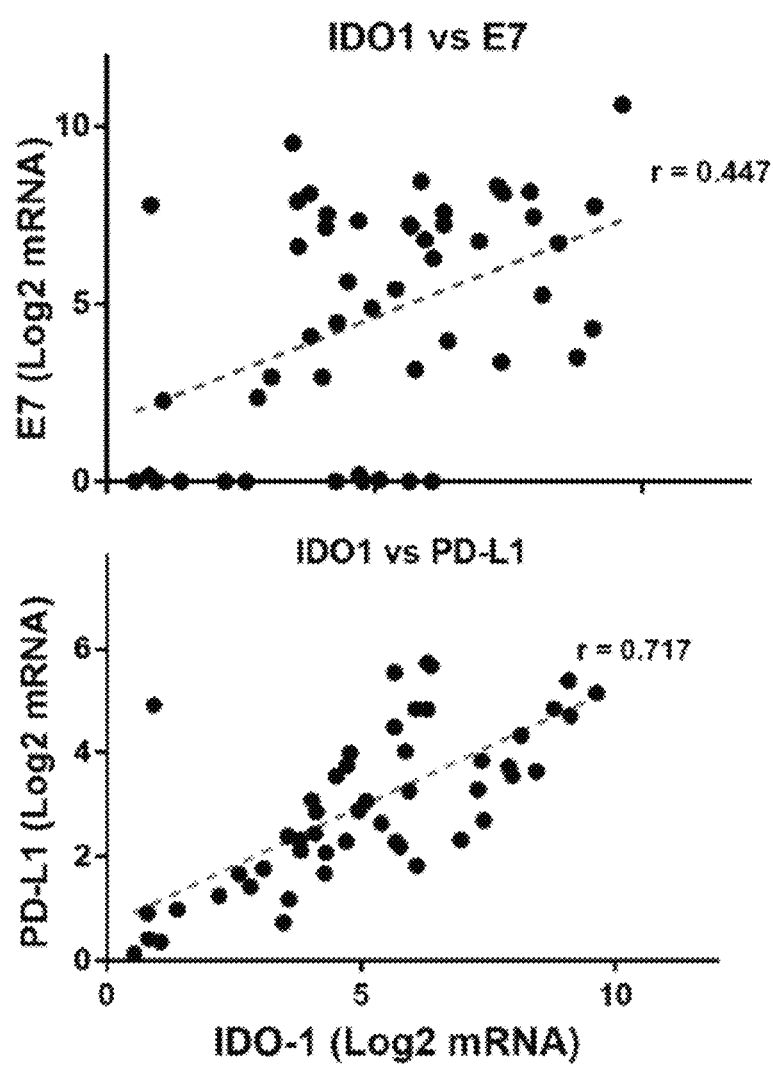
FIGS. 8A-8B show IDO-1 expression. IDO-1 transcript levels correlated with HPV-E7 (FIG. 8A, top panel) and PD-L1 (FIG. 8A, bottom panel) expression. Data derived from HPV+HNSCC samples analyzed in FIG. 4. Pearson correlation coefficients and best fit line (in red) are shown. ssGSEA correlations of IDO-1 with various genes in HPV+ HNSCC patients (FIG. 8B). Red line represents the best fit. Pearson correlations are shown
Figure 8B:
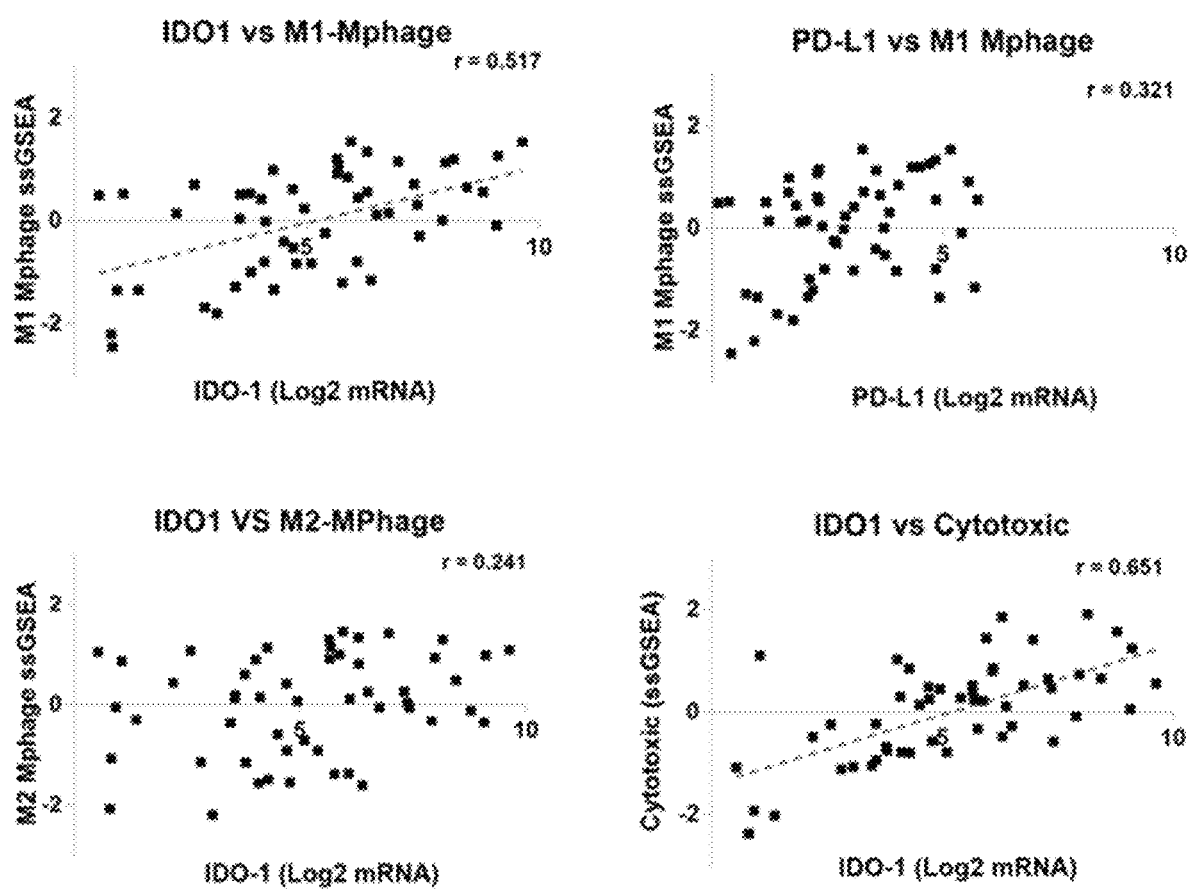

IDO-1 represents a novel HPV+ HNSCC specific immune target. Differential expression of constituent genes was analyzed within the exhaustion gene set between HPV+ HNSCCs and HPV− HNSCCs (FIGS. 5A and 5E). Several well-known T-cell regulatory genes were observed, such as LAG-3, GAL-9, CEACAM-1 and CTLA-4 overexpressed in HPV+ HNSCCs compared to HPV− HNSCCs, consistent with high T-cell infiltration and dysfunction as observed in the results (FIGS. 3-4 and FIG. 5E), and other studies. Interestingly, exhaustion genes NRP1 and CD73 were selectively upregulated in HPV− HNSCCs compared to HPV+ HNSCCs (FIG. 5E), indicating distinct types of T-cell dysfunction between the two HNSCC subtypes. Indoleamine 2,3-dioxygenase (IDO-1), an L-Tryptophan catabolizing enzyme was one of the highest differentially expressed gene (based on ranked P-value) from the exhaustion set HPV+ HNSCCs compared to HPV− HNSCCs (FIG. 5A; Mann-Whitney test, P=0.0012). A cross-cancer (N=30 types, 45708 total tumors) gene expression analysis from cBioPortal, revealed that IDO-1 is also highly expressed in the HPV-malignancy cervical cancer (FIG. 5F). Within the HPV+HNSCCs, IDO-1mRNA levels correlated with HPV16-E7 expression (FIG. 8A, Pearson r=0.447, P=0.001), and with tumor PD-L1 expression (FIG. 8A, Pearson r=0.71, P<0.0001). IDO-1 expression further correlated with M1 Macrophage signature (Pearson r=0.517, P<0.0001), and with cytotoxic signature (Pearson r=0.61, P<0.0001), but only modestly with M2-Macrophage signature (Pearson r=0.24, FIG. 8B). To validate the immune signature analysis indicating that HPV-antigen expression can impact immune regulatory gene expression such as IDO-1 (FIG. 4), immunoblotting was performed for IDO-1 expression in a panel of HPV16+ cancer cell lines (2 cervical, 4 HPV+ HNSCC). These showed variability in HPV16-E7 protein expression (FIGS. 5B-5C). IDO-1 expression followed a striking correlation with E7-protein expression in the same cell lines (R2=0.84, P=0.033, FIG. 5B). Transfection of the 3-HPV16-antigens into a non-HPV cell line (HEK-293-T) did not alter IDO-1 protein expression (FIG. 5G). These results suggest that tumor IDO-1 expression is linked to immune selection pressure from TILs rather than a direct molecular/biochemical consequence of the HPV-life cycle. Of note, PD-L1 protein expression on the same cell lines did not correlate with E7-antigen expression (Spearman ρ=0.17, P=NS; FIG. 5H).

IDO-1 inhibition enhances T-cell targeting of HPV+ HNSCCs. IDO-1 inhibitors are being evaluated in preclinical and clinical settings to enhance tumor immunity. The possibility of exploiting IDO-1 inhibition to overcome HPV-CTL dysfunction, especially using E7-CTLs, was tested. HLA-A*02:01+ HPV+ HNSCC cell line UM-SCC-104 (SCC-104) was fluorescently labeled, which has high IDO-1, E7 and PD-L1 expression (FIGS. 5B and 5H). SCC-104 cells were previously reported to have a distinct hierarchy of HPV16-antigen expression where E7>E6>E2. HPV-CTL mediated cytotoxicity was assessed on SCC-104 cells, after co-incubation with ex vivo expanded HPV-CTLs from an HLA-A*02:01+HPV+ HNSCC patient in the presence of either anti-PD-1 antibody (αPD-1+DMSO) or IDO-1 inhibitor Epacadostat (Ig+IDO-1i), or both (αPD-1+ IDO-1i). Within E7-CTLs (FIGS. 5C and 5D, right side), single-agent treatment with either αPD-1 or IDO-1i individually resulted in a 3-5 fold increase in sensitivity of SCC-104 to E7-CTL mediated cytotoxicity compared to mock (Ig+DMSO) treatment (FIGS. 5C-5D; αPD-1 vs. mock, P=0.024, IDO-1i vs. mock, P=0.064). In contrast, combination blockade with both αPD-1+IDO-1i resulted in a 10-fold increase in tumor cytotoxicity compared to mock treatment (FIGS. 5C-5D; P=0.011), and a 2-3 fold increase in tumor cytotoxicity compared to the single-agent treatments (FIGS. 5C-5D; P=0.04 compared to IDO-1i, P=0.013 compared to αPD-1). Similar results were obtained with αPD-1+IDO-1i combination therapy on E2 and E6 CTL cytotoxicity although to a lesser extent (3-fold increase for E2, and 5-fold increase for E6 compared to mock treatment, P<0.01), likely reflecting the lower expression of these antigens in SCC-104 cell line. These results demonstrate that IDO-1 is a novel HPV+ HNSCC specific checkpoint correlating with HPV-antigen expression, and combination inhibition of PD-1 and IDO-1 can sensitize HPV+ HNSCCs to HPV-CTL mediated cytotoxicity.

IDO-1 is an HPV-specific immune target and can enhance HPV-T-cell cytotoxicity. Shown in FIG. 5A are the $Log_2$-TPM levels of IDO-1 in HPV+vs. HPV− HNSCC transcriptomes. Each data point represents one patient. The P-value from Mann-Whitney test is shown. FIG. 5B quantifies the correlation of IDO-1 protein levels to HPV16-E7 antigen expression in 6 HPV16 cell lines (2 cervical cancer, 4 HPV16+HNSCC cell lines) as determined by an immunoblot of protein levels in the cell lines, normalized to GAPDH (top panel). The lower panel graphs the results with a regression line corresponding to $R^2=0.84$, P=0.033. Cell-tracker labeled SCC-104 cells were co-incubated with polyclonal multi-epitope stimulated E2, E6 and E7-specific T-cells at an effector/target ratio of 5:1 for 48 hours, and assessed for cell death (TRACK+ PI+ events) under αPD-1, IDO-1 single or dual-inhibition conditions. FIG. 5C is a representative flow cytometry plot from E7-specific T-cell mediated cytotoxicity on SCC-104 cells. Numbers indicate percent celltracker labeled dead SCC-104 cells. FIG. 5D summarizes the labelled dead SCC-104 cells (3 biological replicates) by E2, E6 and E7 specific CTLs under control, single and double-agent treatments of αPD-1 and IDO-1. Statistics were determined using an unpaired two-tailed Welch T-test, *P<0.1, **P<0.01, as indicated. FIG. 5E shows the differential expression of exhaustion genes in HPV+vs. HPV− HNSCCs. Box plots representing $Log_2$ TPM from HPV+, HPV− HNSCC patients show the median expression levels from the exhaustion gene set, whiskers indicate 10-90th percentile. Each data point represents one patient. Calculated P values as determined by the Mann-Whitney test are indicated. FIG. 5F proves that IDO-1 expression is found across all cancers and is uninfluenced by HPV16-genes. $Log_2$ mRNA TPM levels were obtained from cBioportal for 30 different types of cancers from 45708 total tumors from TCGA. Each blue data point represents expression from one patient tumor for respective cancer, red representing a mutation or other alteration and grey represents unsequenced tumors. FIG. 5G shows the immunoblots measuring IDO-1 expression levels in HEK-293-LX cells after transfection with the 3 HPV16-E2, E6 and E7 genes. Cell surface PD-L1 protein expression in the same 6 HPV16 cell lines as in FIG. 5B were analyzed by flow cytometry and the normalized mean fluorescence intensity results are shown in FIG. 5H. The erythroleukemic cell line K562 represents the negative control.

Materials and Methods

HPV16 candidate CTL-epitope prediction. HPV16-candidate CTL epitopes were predicted using previously described prediction strategies (Krishna S, Anderson K S. *Methods Mol Biol.* 2016; 1403:779-96 and Chowell D, et al. *Proc Natl Acad Sci USA.* 2015; 112:E1754-62.), except for the incorporation of immunogenicity scores. For the 15 HLA-class I alleles, 9-mer and 10-mer candidate epitopes derived from the HPV16 proteins E2, E6, and E7 were predicted from 5 independent prediction algorithms and normalized. HLA-class I restricted 9-mer and 10-mer candidate epitopes derived from the HPV16 proteins E2, E6, and E7 were predicted for the HLAs A*01:01, A*02:01, A*03:01, A*11:01, A*24:02, B*07:02, B*08:01, B*15:01, B*27:05, B*35:01, B*40:01, B*40:02, B*44:02 B*51:01, and B*57:01. Top 4-5 candidate peptides/HLA-allele were used for experiments.

The protein reference sequences for each of HPV16 proteins were obtained from Papillomavirus Episteme (PAVE) and were then entered into 5 different prediction algorithms; 3 MHC-binding: IEDB-consensus binding, NetMHCpan binding, Syfpeithi and 2 antigen-processing algorithms: IEDB-consensus processing, ANN processing. The individual scores from each of the prediction algorithms were then normalized within the pool of predicted peptides after removal of poor-binders, and the mean normalized binding scores were used to re-rank the candidate peptides. Top 4-5 candidate peptides satisfying binding percentile scores>80% (FIGS. 1G-1J) were chosen per antigen per HLA-allele for experimental testing. Predicted candidate HPV16-peptides, individual normalized and total binding percentile scores are listed in Tables 1-4.

Ex vivo stimulation and epitope mapping of HPV+HNSCC PBMCs. PBMCs were obtained from stage Ill or stage IV HPV+ HNSCC patients (MSSM cohort). All HPV16-peptides (>80% purity) were synthesized by Proimmune, UK. HPV+ HNSCC PBMCs were thawed, rested with 1 μg/mL of CKB antibodies anti-PD1 (eBosciences, USA), anti-CTLA4 (eBosciences, USA) for 1 hour at 37° C. HPV16-peptides in pool or individually were added subsequently in biological triplicates, along with recombinant human IL-2 (20 U/mL), human IL-7 (5 ng/mL). On day 5, half the media was removed and replaced with fresh IL-2 and peptide pool. On day 8, half the media was removed and fresh media, IL-2 and peptide was added to the cells and replated into a 96-well multiscreen elispot plate for Elispot detection.

PBMCs were obtained from stage Ill or stage IV HPV+ HNSCC patients (MSSM cohort) as described previously. All human PBMCs were obtained using informed consent under clinical protocol HSM 10-00585. PBMCs were stimulated as previously described. Briefly, HPV16-peptide pools shown in FIG. 1 (Tables 1-4) were designed to have equal representation of peptides predicted for each HLA-allele to prevent intra-pool peptide competition for binding to the same HLA (Tables 1-4). All peptides (>80% purity) were synthesized by Proimmune, UK. The HPV-peptide pools were created by mixing 7-8 HPV16 candidate peptides by antigen, each at a concentration of 1 mg/mL per peptide in sterile 1× PBS. For individual peptides, each peptide was reconstituted at 1 mg/mL in sterile 1×PBS. Frozen PBMCs were thawed rapidly and stimulated with 10 μg/mL premixed HIV-negative control peptide pool, HPV16-peptide pools or pre-mixed CEF-positive control pool (all from ProImmune, UK) in biological triplicates in a sterile 96-well U-bottomed plate (Costar, Washington D.C., USA). Recombinant human IL-2 (20 U/mL), human IL-7 (5 ng/mL) and 1 μg/mL of checkpoint blockade antibodies anti-PD1 (clone J105, eBosciences, USA), anti-CTLA4 (clone 14D3, eBosciences, USA) were added and cells were rested for two hours at 37 C prior to peptide stimulation. On day 5, half the media was removed and replaced with fresh IL-2 and peptide pool. On day 8, half the media was removed and fresh media, IL-2 and peptide was added to the cells and replated into a 96-well multiscreen elispot plate for Elispot detection. Same procedure was repeated for individual epitope mapping and deconvolution using selected candidate epitopes as per the patient's HLA-restriction (FIG. 2).

HPV-CTL stimulation for phenotyping. HPV-specific T-cells were generated by stimulating autologous HPV+ HNSCC patient B-cell APCs. APCs were either peptide pulsed with HPV16-epitopes, or transfected with whole HPV-antigen encoded in mammalian expression plasmid pCDNA3.2 (Invitrogen, CA, USA). APCs were washed and incubated with thawed whole HPV+ HNSCC PBMCs at a ratio of 1:2 (200,000 APCs: 400,000 PBMCs) supplemented with 20 U/mL recombinant human IL-2 (R&D Systems, MN, USA), 5 ng/mL IL-7 (R&D Systems, MN, USA). On day 5, partial media exchange was performed. On day 10, expanded HPV-CTLs were restimulated with peptide-pulsed, transfected APCs similar to day 1. HPV-CTLs were used for cytolytic assays or immunophenotyped after day 20.

Tetramer staining, HPV-CTL and HPV+cell line phenotyping. HPV16-tetramers were obtained from NIH Tetramer Core Facility at Emory University. For tetramer staining, cells were re-suspended in 100 μL staining buffer with 5% human serum and 1 mM Dasatanib (ThermoFisher Scientific, MA, USA), and each tetramer was added at concentration of 1:100 for 30 minutes at room temperature. Cells were washed twice and restained with anti-CD8-PC5, anti-CD4-FITC, anti-CD14-FITC and anti-CD19-FITC for exclusion gates, and either a combination of anti-PD1-BV605 and anti-CD39-BV-405 or anti-PD1-BV-605 and anti-TIM3-BV-405 for 30 minutes on ice. HPV+cell line PD-L1 staining was done for 30 minutes on ice. Samples were then washed twice in 1×PBS, and analyzed by Attune flow cytometer (ThermoFisher Scientific, MA, USA).

Flow cytometry staining for T-cell and tumor immunophenotyping. Cells were washed once in MACs buffer (containing 1×PBS, 1% BSA, 0.5 mM EDTA), centrifuged at 550 g, 5 minutes, and re-suspended in 200 μL MACS buffer. Cells were stained in 100 μL of staining buffer containing anti-CD137, conjugated with phycoerythrin (PE, clone 4B4-1; BD Biosciences, USA), anti-CD8-PC5 (clone B9.11; Beckman Coulter 1:100), anti-CD4 (clone SK3; BioLegend, 1:200), anti-CD14 (clone 63D3; BioLegend, 1:200) and anti-CD19 (clone HIB19; BioLegend, 1:200), all conjugated to Fluorescein isothiocyanate (FITC) for exclusion gates, and either a combination of anti-PD1-Brilliant Violet 605 (BV605, clone EH12.2H7; BioLegend, 1:50) and anti-CD39-BV-405 (clone A1; BioLegend, 1:200) or anti-PD1-BV-605 and anti-TIM3-BV-405 (clone F38-2E2; BioLegend, 1:50) for 30 minutes on ice. PD-L1 staining on HPV+HNSCC and cervical cancer cell lines were done using 5 μL PD-L1 antibody (clone MIH1, ThermoFisher Scientific, MA, USA) in 100 μL MACS buffer. Samples were covered and incubated for 30 min on ice then washed twice in 1×PBS, and resuspended in 1 mL 1×PBS prior to analysis.

Tetramer staining for T-cell immunophenotyping. The following HLA-A*02:01 HPV16 tetramers were obtained from NIH Tetramer Core Facility at Emory University: TLQDVSLEV E2(93-101), YICEEASVTV E2(138-147), ALQAIELQL E2(69-77), KLPQLCTEL E6(18-26), TIH-DIILECV E6(29-38), FAFRDLCIV E6(52-60), YMLDLQPET E7(11-19), and YMLDLQPETT E7(11-20). Cells were washed (550 g, 5 min) twice in MACS buffer with 5% human serum. After washing, cells were re-suspended in 100 µL staining buffer (MACS buffer, with 5% human serum and 1 mM Dasatanib (ThermoFisher Scientific, MA, USA). Each of the eight HLA-A*02:01 HPV16 tetramers (NIH Tetramer Core, Emory University, Atlanta, USA), all conjugated with phycoerythrin (PE) was added to each respective sample at concentration of 1:100. Samples were incubated at room temperature for 30 minutes under dark. After incubation, cells were washed 2× in MACS buffer. Cells were stained in 100 µL MACS buffer with anti-CD8-PC5, anti-CD4-FITC, anti-CD14-FITC and anti-CD19-FITC for exclusion gates, and either a combination of anti-PD1-BV605 and anti-CD39-BV-405 or anti-PD1-BV-605 and anti-TIM3-BV-405 for 30 minutes on ice. Samples were then washed twice in 1×PBS, and analyzed by flow cytometry. For flow cytometric analysis, all samples were acquired with Attune flow cytometer (ThermoFisher Scientific, MA, USA) and analyzed using Attune-software. Gates for expression of different markers and tetramers were determined based on flow minus one (FMO) samples for each color after doublet discrimination. Only samples with >50 CD8+Tetramer+ or CD8+CD137+ events were considered. Percentages from each of the gated population were used for the analysis.

Cell lines and immunoblotting experiments. Cervical cancer cell lines SiHa and Caski were obtained from ATCC (Manassas, Va., USA). HPV+HNSCC cell lines were obtained from the following sources: UPCI:SCC90 (SCC90) was obtained from ATCC (Manassas, USA), UM-SCC-47 (SCC47) and UM-SCC-104 (SCC104) from Merck Millipore (Billerica, Mass., USA). All cell lines contained integrated HPV-16 DNA, and were maintained in the following media: Caski was maintained in RPMI-1640 (ATCC) with 10% heat inactivated fetal bovine serum (FBS), SiHa in Eagle's Minimum Essential Medium (EMEM, ATCC, USA) with 10% FBS, SCC90 and, SCC47 in Dulbecco's Modified Eagle's Medium (DMEM, ATCC, USA) with 10% FBS, SCC104 cells were maintained in Iscove's Modified Dulbecco's Medium (IMDM, Gibco, NY, USA) with 10% human serum. Cells were harvested by trypsinization (0.25% Trypsin, GE Healthcare, IL, USA), and resuspended in 1 mL RIPA buffer (Invitrogen, CA, USA) containing a cocktail of protease inhibitors (Roche Diagnostics, IN, USA). Equal amounts of cell lysates were loaded on a 4-20% SDS-polyacrylamide gel (Invitrogen, CA, USA) and transferred to a Polyvinylidene fluoride membrane (GE Healthcare, IL, USA). The membrane was blocked with 5% nonfat dry milk in PBS-1% Tween (PBST) for 1 hour at room temperature. Primary antibodies and concentrations were as follows: GAPDH (Cell Signalling Technologies, MA, USA, clone 14C10, 1:2000), IDO-1 antibody (ThermoFisher Scientific, clone PA5-29819, 1:1000), anti-HPV16-E7 antibody (Fitzgerald industries, MA, USA, clone 10-7987, 1:1000). Visualization was done with Dura Western Blotting Kit (Thermo Scientific, USA) according to the manufacturer's instructions.

HPV-CTL cytotoxicity assays. HLA-A*02:01+HPV+HNSCC+ SCC-104 cells were pre-labelled with 0.5 µM CellTracker Green CMFDA (ThermoFisher Scientific, MA, USA) for 1 hour and washed. HPV-specific CTLs were pooled by HPV-antigen, washed and resuspended in media supplemented with 20 U/mL IL-2, with 1 µg/mL isotype IgG or anti-PD1 antibody, DMSO, and 1 µM IDO-1 inhibitor Epacadostat (Selleck Chemicals, MA, USA) in various combinations as described. HPV-CTLs were added at ratio of 5:1 to SCC-104 cells and incubated for 48 hours at 37 C, 5% $CO_2$. Cocultured cells were harvested, neutralized with media supernatant from each well containing dead cells and centrifuged for 850 g, 10 minutes. Cell pellets were washed twice with sterile 1×PBS, resuspended with 1 mL 1×PBS, and 2 uL Propidium Iodide (ThermoFisher Scientific, MA, USA) and cell death was assessed by flow cytometry. All samples were acquired with Attune flow cytometer (ThermoFisher Scientific, MA, USA) in blue-violet configuration and analyzed using Attune-software.

HLA-A*02:01 expressing HPV+HNSCC cell line SCC-104 was used for cytotoxicity assays. SCC-104 cells were plated at a density of 50,000 cells per well in a flat bottom 96-well sterile treated plate (Corning, USA). Twenty four hours later, cells were pre-labelled with 0.5 µM CellTracker Green CMFDA (ThermoFisher Scientific, MA, USA) for one hour, washed thrice with sterile 1×PBS. HPV-specific CTLs generated by either peptide pulsing or transfected antigens were pooled by HPV-antigen, washed and resuspended in BCM supplemented with 20 U/mL IL-2 along with 1 µg/mL isotype IgG antibody, anti-PD1 antibody (eBiosciences, USA), DMSO, and 1 µM IDO-1 inhibitor Epacadostat (Selleck Chemicals, MA, USA) in various combinations as described. HPV-CTLs were added at ratio of 5:1 to SCC-104 cells and incubated for 48 hours at 37° C., 5% $CO_2$. The cocultured cells were harvested by trypsinization, neutralized with media supernatant from each well containing dead cells and centrifuged for 850 g, 10 minutes. Cell pellets were washed twice with sterile 1×PBS, resuspended with 1 mL 1×PBS, and 2 uL Propidium Iodide (ThermoFisher Scientific, MA, USA) and cell death was assessed by flow cytometry. All samples were acquired with Attune flow cytometer (ThermoFisher Scientific, MA, USA) in blue-violet configuration and analyzed using Attune-software.

RNASeq data alignment. RNA-Seq reads for each sample were quality checked using FastQC (version 0.10.1, Babraham bioinformatics, Babraham Institute, Cambridge, UK) and aligned to the human genome build 38 (GRCh38, CF_000001405.33_GRCh38.p7_genomic.fna) primary assembly and HPV16 genome (GCF_000863945.1_ViralProj15505_genomic.fna) simultaneously using STAR (version 2.5.2B). After alignment, variants were discovered following GATK Best Practices workflow for RNAseq (gatkforums.broadinstitute.org/gatk/discussion/3892/the-gatk-best-practices-for-variant-calling-on-rnaseq-in-full-detail). Raw RNAseq reads were pre-processed by adding read groups, indexing, marking duplicates and sorting, Split'N'Trim, reassigning mapping quality and base recalibration.

RNASeq datasets and gene signature sources. Transcriptome data for HNSCC patient samples (n=119) were obtained from TCGA (TCGA-cohort), and University of Michigan study (UM-cohort). In total, there were 34 and 18 HPV+HNSCC samples from TCGA-cohort and UM-cohort respectively. HPV−HNSCC dataset comprised of 18 tumors from UM-cohort and 49 tumors from TCGA dataset that were both HPV-negative by p16 status and HPV-FISH. For ssGSEA analysis, immune signatures, comprising of 509 genes were obtained from previous studies. Additional gene signatures were obtained as follows: Custom HPV gene sets were grouped into HPV (All 8 HPV genes), HPV. Onco (E6, E7) and HPV.Early (E2, E4, E5). TIGIT gene signature (50 genes) was obtained from Johnston et al., TIL.Treg (309 genes) and Exhaust gene sets (49 genes) were obtained from De Simone et al., and CYT (GZMA, PRF) from Rooney et al.

HLA typing. For MSSM-cohort, HLA-typing was performed by Proimmune HLA-tissue typing services, UK. For HLA-calling from RNAseq data (TCGA and UM cohorts), PHLAT (Bai et al., 2014) was used to infer the HLA typing of the three major MHC class I (HLA-A, -B, -C) alleles. The method employs a read mapping based selection of candidate allele followed by a likelihood based scoring over all pairwise combinations of selected alleles and infers the first four digits with a high accuracy. For HLA-odds ratio calculations, HLA-allele typing from all 3 cohorts (MSSM, TCGA and UM) were combined resulting in 64 HPV−HNSCC (TCGA) and 77 HPV+HNSCCs.

HPV16 epitope-prediction from RNAseq data. HLA types obtained from PHLAT were used to predict the epitopes binding to patient-specific HLA alleles. Binding affinities were predicted using IEDB recommended algorithm from the Immune Epitope Database (IEDB) tool. Reference fasta files for HPV protein sequences were used to predict peptide lengths of 8, 9, 10, 11 for each patient's allele and peptide combination. If the matching HLA allele of the patient did not exist in the current IEDB list, the closest allele was identified by keeping the first two digits the same and searching for the nearest available match for the third and fourth digit. To retain only high affinity binding epitopes with the patient-specific HLA alleles, epitopes with a binding affinity greater than 500 nM were not considered in downstream analyses.

ssGSEA analysis of HPV and immune gene signatures. Log transformed transcripts per million (Log 2 TPM+1) from each HNSCC sample, after subtraction of low expression genes was used for ssGSEA as previously described in Şenbabaoğlu et al. Pre-defined immune signatures, have been extensively validated in Şenbabaoğlu et al., and Mandal et al. ssGSEA scores were computed for each tumor sample using the R package GSVA, and Z-transformed across the cohort prior to analysis. To assess impact of HPV-gene expression on immune signatures, a correlation matrix was built using the R-library Corrplot with the Z-transformed ssGSEA scores and were displayed by hierarchical clustering of correlations. (Clustered correlation matrix values for each gene-set correlations not shown but available upon request). Individual gene expression analysis was performed by unsupervised hierarchical clustering methods and were used for heatmap analysis in FIG. 4 and FIG. 5E.

Elispot detection of IFNγ secretion. Elispot detection assay was performed as previously described. Briefly, sterile multiscreen Elispot plates, (Merck Millipore, Billerica, Mass., USA) precoated overnight with 5 μg/well anti-IFNγ capture antibody (clone D1K, Mabtech, USA) in sterile 1×PBS. Eight days after stimulation, HPV+HNSCC PBMCs were subject to media change and IL-2, peptide (pools or individual) were added. Cells in each well were transferred to the Elispot plate and incubated at 37° C. 5% $CO_2$ incubator for 48 hours. Plates were washed with elispot buffer (PBS+0.5% FBS) and incubated with 1 μg/mL anti-IFNγ secondary detection antibody (clone 7-B6-1, Mabtech, USA) for 2 hours at room temperature, washed and reincubated with 1 μg/mL Streptavidin ALP conjugate for 1 hour at room temperature. The wells were washed again with elispot buffer and spots were developed by incubating for 8-10 minutes with detection buffer (33 μL NBT, 16.5 μL BCIP, in 100 mM Tris-HCl pH 9, 1 mM $MgCl_2$, 150 mM NaCl). Plates were dried for 2 days and spots were read using the AID Elispot reader (Autoimmun Diagnostika GmbH, Germany). Average number of spot forming units for the triplicates were calculated for each test peptide/pool and subtracted from background (either HIV-control peptide pool or PBS-DMSO controls).

RAPID-ELISA for E2, E6 and E7 seroreactivity in HPV+ HNSCC patients. RAPID-ELISA was performed as described previously. Briefly, patient sera were diluted 1:100 and blocked with E. coli lysate. Each antigen was expressed from template cDNA and captured onto 96-well plates coated with anti-GST Ab (GE Healthcare, Piscataway, N.J.) in duplicates. Horseradish peroxidase (HRP) anti-human IgG Abs (Jackson ImmunoResearch Laboratories, West Grove, Pa.) were added at 1:10,000, and detected using Supersignal ELISA Femto Chemiluminescent substrate (Thermo Scientific). Luminescence was detected as relative light units (RLU) on a Glomax 96 Microplate Luminometer (Promega, Madison, Wis.) at 425 nm. To control for non-specific and GST-specific antibodies, the ratio of RLU for individual HPV-specific Abs to the RLU for the control GST-antigen was measured.

Autologous APC generation from HPV+HNSCC patient PBMCs. Autologous CD40L-activated B-cell APCs were generated from specific HPV+HNSCC patients by incubating whole PBMCs with irradiated (32 Gy) K562-cell line expressing human CD40L (KCD40L) at a ratio of 4:1 (800,000 PBMCs to 200,000 irradiated KCD40Ls) in each well. The cells were maintained in B-cell media (BCM) consisting of IMDM (Gibco, USA), 10% heat inactivated human serum (Gemini Bio Products, CA, USA), Antibiotic-Antimycotic (Anti-Anti, Gibco, USA). BCM was supplemented with 10 ng/mL recombinant human IL-4 (R&D Systems, MN, USA), 2 μg/mL Cyclosporin A (Sigma-Aldrich, CA, USA), 1× insulin transferrin supplement (ITES, Lonza, MD, USA). APCs were re-stimulated with fresh irradiated KCD40Ls on days 5 and 10, after washing with 1×PBS and expanding into a whole 24-well plate. After two weeks, APC purity was assessed by CD19+ CD86+ expressing cells by flow cytometry, and were generally used for T-cell stimulation after >90% purity. APCs were either restimulated upto 4 weeks or frozen and re-expanded as necessary.

HPV-CTL stimulation by autologous APCs. Antigen-specific T-cells were generated by stimulating HPV+HNSCC patient B-cell APCs by either peptide pulsing of specific HPV16-epitopes, or by transfecting whole antigen encoded in mammalian expression plasmid pCDNA3.2 (Invitrogen, CA, USA). Peptide pulsing of APCs was done under BCM 5% human serum, with recombinant IL-4. Transfection of APCs were done using the Lonza 4D Nucleofector, primary P3 buffer, program E0117 (Lonza, MD, USA) and incubated in BCM-10% human serum, IL-4 without any Anti-Anti. Twenty four hours later, on day 1, APCs were washed and incubated with thawed whole HPV+ HNSCC PBMCs at a ratio of 1:2 (200,000 APCs: 400,000 PBMCs) in a 24-well plate in BCM supplemented with 20 U/mL recombinant human IL-2 (R&D Systems, MN, USA), 5 ng/mL IL-7 (R&D Systems, MN, USA). On day 5, partial media exchange was performed by replacing half the well with fresh B-cell media and IL-2. On day 10, fresh APCs were either peptide pulsed or transfected as described above in a new 24-well plate. On day 11, expanded T-cells were restimulated with peptide-pulsed, transfected APCs similar to day 1. T-cells were used for cytolytic assays or immuno-phenotyped after day 20.

Statistical Analysis. Categorical variables, such as Elispot data, and Flow cytometric data were summarized as SFUs, and percentages. Continuous variables (RNAseq data) were presented with mean with standard error of mean (SEM). Unpaired T-test with Welch's correction was used for all categorical variable analyses, and for continuous variable analyses non-parametric Mann-Whitney's test was used. For heatmaps of T-cell frequencies and ssGSEA RNASeq analyses, Z-transformation was performed to normalize the data across the cohorts. R statistical software V3.4.0 and Prism software (GraphPad Software) were used for data managements and statistical analyses. Significance levels were set at 0.1 (*), and P-values of 0.01 () or 0.001 (*) for all tests are indicated.

Various features and advantages of the invention are set forth in the following claims.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Sequence Listing Information

As described herein, polypeptides, compositions, and methods can include any of the following SEQ ID NOs.

TABLE 5

| | | SEQ ID NOs | | |
|---|---|---|---|---|
| Pool | Epitope label | Position | HLA | Sequence |
| E2 Pool 1 | A01-A03-B57-E2 | E2(329-338) | HLA-B*15:01 | KSAIVTLTY (SEQ ID NO: 1) |
| | | E2(329-338) | HLA-B*57:01 | KSAIVTLTY |
| | | E2(329-338) | **HLA-A*01:01 | KSAIVTLTY** |
| | | E2(329-338) | HLA-A*11:01 | KSAIVTLTY |
| | | E2(329-338) | HLA-A*03:01 | KSAIVTLTY |
| | | E2(329-338) | HLA-B*35:01 | KSAIVTLTY |
| | A02-E2-1 | E2(93-101) | HLA-A*02:01 | TLQDVSLEV (SEQ ID NO: 2) |
| | A02-E2-2 | E2(138-147) | HLA-A*02:01 | YICEEASVTV (SEQ ID NO: 3) |
| | A03-E2-1 | E2(37-45) | HLA-A*11:01 | RLECAIYYK (SEQ ID NO: 4) |
| | | E2(37-45) | HLA-A*03:01 | RLECAIYYK |
| | A11-E2-1 | E2(284-292) | **HLA-A*11:01 | NTTPIVHLK (SEQ ID NO: 5)** |
| | A24-E2-2 | E2(101-110) | HLA-A*24:02 | VYLTAPTGCI (SEQ ID NO: 6) |
| | B07-E2-1 | E2(207-215) | **HLA-B*07:02 | SPEIIRQHL (SEQ ID NO: 7)** |
| | B08-B27-E2 | E2(303-311) | HLA-B*08:01 | YRFKKHCTL (SEQ ID NO: 8) |
| | | E2(303-311) | HLA-B*27:05 | YRFKKHCTL |
| | | E2(303-311) | HLA-B*40:02 | YRFKKHCTL |
| E2 Pool 2 | A01-E2-1 | E2(147-155) | HLA-A*01:01 | VVEGQVDYY (SEQ ID NO: 9) |
| | A02-E2-3 | E2(69-77) | **HLA-A*02:01 | ALQAIELQL (SEQ ID NO: 10)** |
| | A02-E2-5 | E2(310-318) | HLA-A*02:01 | TLYTAVSST (SEQ ID NO: 11) |
| | A03-E2-2 | E2(267-276) | **HLA-A*03:01 | ILTAFNSSHK (SEQ ID NO: 12)** |
| | | E2(267-276) | HLA-A*11:01 | ILTAFNSSHK |
| | A11-E2-2 | E2(103-112) | HLA-A*11:01 | LTAPTGCIKK (SEQ ID NO: 13) |
| | | E2(103-112) | **HLA-A*03:01 | LTAPTGCIKK** |
| | B07-E2-2 | E2(218-227) | HLA-B*07:02 | HPAATHTKAV (SEQ ID NO: 14) |
| | B08-E2-1 | E2(62-70) | HLA-B*08:01 | LAVSKNKAL (SEQ ID NO: 15) |
| | | E2(62-70) | HLA-B*35:01 | LAVSKNKAL |
| | B35-E2-1 | E2(263-271) | HLA-B*35:01 | DSAPILTAF (SEQ ID NO: 16) |
| E2 Pool 3 | A01-E2-2 | E2(94-102) | HLA-B*15:01 | LQDVSLEVY (SEQ ID NO: 17) |
| | | E2(94-102) | HLA-A*01:01 | LQDVSLEVY |
| | A02-E2-4 | E2(102-110) | HLA-A*02:01 | YLTAPTGCI (SEQ ID NO: 18) |
| | A02-E2-6 | E2(191-199) | HLA-A*02:01 | QVILCPTSV (SEQ ID NO: 19) |

TABLE 5-continued

SEQ ID NOs

| Pool | Epitope label | Position | HLA | Sequence |
|---|---|---|---|---|
| | A02-E2-6 | E2(297-306) | HLA-A*02:01 | TLKCLRYRFK (SEQ ID NO: 20) |
| | | E2(297-306) | **HLA-A*03:01 | TLKCLRYRFK** |
| | | E2(297-306) | HLA-A*11:01 | TLKCLRYRFK |
| | A24-E2-1 | E2(302-312) | HLA-A*24:02 | RYRFKKHCTL (SEQ ID NO: 21) |
| | | E2(302-312) | HLA-B*27:05 | RYRFKKHCTL |
| | B07-E2-3 | E2(249-257) | **HLA-B*07:02 | NPCHTTKLL (SEQ ID NO: 22)** |
| | B08-E2-2 | E2(163-171) | HLA-B*15:01 | GIRTYFVQF (SEQ ID NO: 23) |
| | | E2(163-171) | HLA-B*08:01 | GIRTYFVQF |
| | B35-E2-2 | E2(158-167) | HLA-B*15:01 | YYVHEGIRTY (SEQ ID NO: 24) |
| | | E2(158-167) | **HLA-B*35:01 | YYVHEGIRTY** |
| E6-Pool-1 | A24-B08-E6 | E6(82-90) | HLA-A*24:02 | EYRHYCYSL (SEQ ID NO: 25) |
| | | E6(82-90) | HLA-B*08:01 | EYRHYCYSL |
| | A03-E6-1 | E6(33-41) | HLA-A*03:01 | IILECVYCK (SEQ ID NO: 26) |
| | | E6(33-41) | **HLA-A*11:01 | IILECVYCK** |
| | A01-E6-1 | E6(80-88) | HLA-A*01:01 | ISEYRHYCY (SEQ ID NO: 27) |
| | B35-B57-E6 | E6(59-67) | HLA-B*15:01 | IVYRDGNPY (SEQ ID NO: 28) |
| | | E6(59-67) | HLA-B*35:01 | IVYRDGNPY |
| | | E6(59-67) | HLA-B*57:01 | IVYRDGNPY |
| | A02-E6-1 | E6(18-26) | HLA-A*02:01 | KLPQLCTEL (SEQ ID NO: 29) |
| | B07-E6-1 | E6(15-24) | HLA-B*07:02 | RPRKLPQLCT (SEQ ID NO: 30) |
| | A11-E6-1 | E6(93-101) | HLA-A*11:01 | TTLEQQYNK (SEQ ID NO: 31) |
| E6-Pool-2 | A03-E6-2 | E6(68-77) | HLA-A*11:01 | AVCDKCLKFY (SEQ ID NO: 32) |
| | A24-E6-2 | E6(87-95) | HLA-A*24:02 | CYSLYGTTL (SEQ ID NO: 33) |
| | B08-E6-1 | E6(44-52) | HLA-B*15:01 | LLRREVYDF (SEQ ID NO: 34) |
| | | E6(44-52) | HLA-B*08:01 | LLRREVYDF |
| | B07-E6-2 | E6(65-74) | **HLA-B*07:02 | NPYAVCDKCL (SEQ ID NO: 35)** |
| | A02-E6-2 | E6(29-38) | HLA-A*02:01 | TIHDIILECV (SEQ ID NO: 36) |
| | A01-E6-2 | E6(69-77) | HLA-A*01:01 | VCDKCLKFY (SEQ ID NO: 37) |
| | B35-E6-1 | E6(67-76) | HLA-B*35:01 | YAVCDKCLKF (SEQ ID NO: 38) |
| | | E6(67-76) | HLA-B*15:01 | YAVCDKCLKF |
| E6-Pool-3 | B07-E6-3 | E6(119-126) | **HLA-B*07:02 | CPEEKQRHL (SEQ ID NO: 39)** |
| | A11-E6-2 | E6(37-47) | HLA-A*11:01 | CVYCKQQLLR (SEQ ID NO: 40) |
| | | E6(37-47) | HLA-A*03:01 | CVYCKQQLLR |
| | B08-E6-2 | E6(127-135) | HLA-B*08:01 | DKKQRFHNI (SEQ ID NO: 41) |
| | A02-E6-3 | E6(52-60) | HLA-A*02:01 | FAFRDLCIV (SEQ ID NO: 42) |
| | A03-E6-3 | E6(106-116) | **HLA-A*03:01 | LLIRCINCQK (SEQ ID NO: 43)** |
| | | E6(106-116) | HLA-A*11:01 | LLIRCINCQK |
| | B35-E6-2 | E6(82-90) | HLA-B*35:01 | YGTTLEQQY (SEQ ID NO: 44) |
| E7-Pool-1 | A01-E7-1 | E7(15-23) | HLA-B*15:01 | LQPETTDLY (SEQ ID NO: 46) |
| | | E7(15-23) | HLA-A*01:01 | LQPETTDLY |
| | A01-B35-B57-E7 | E7(2-11) | HLA-A*01:01 | HGDTPTLHEY (SEQ ID NO: 47) |
| | | E7(2-11) | HLA-B*35:01 | HGDTPTLHEY |
| | | E7(2-11) | HLA-B*57:01 | HGDTPTLHEY |

TABLE 5-continued

SEQ ID NOs

| Pool | Epitope label | Position | HLA | Sequence |
|---|---|---|---|---|
| | A02-E7-1 | E7(82-90) | **HLA-A*02:01 | LLMGTLGIV (SEQ ID NO: 48)** |
| | | E7(82-90) | HLA-B*15:01 | LLMGTLGIV |
| | A03-E7-1 | E7(51-60) | HLA-A*03:01 | HYNIVTFCCK (SEQ ID NO: 49) |
| | | E7(51-60) | HLA-A*11:01 | HYNIVTFCCK |
| | A03/A11-E7-3 | E7(88-97) | HLA-A*11:01 | GIVCPICSQK (SEQ ID NO: 50) |
| | | E7(88-97) | **HLA-A*03:01 | GIVCPICSQK** |
| | B07-B08-B35-E7 | E7(5-13) | HLA-B*07:02 | TPTLHEYML (SEQ ID NO: 51) |
| | | E7(5-13) | HLA-B*08:01 | TPTLHEYML |
| | | E7(5-13) | HLA-B*35:01 | TPTLHEYML |
| | B35-E7-1 | E7(16-25) | HLA-B*44:02 | QPETTDLYCY (SEQ ID NO: 52) |
| | | E7(16-25) | HLA-B*35:01 | QPETTDLYCY |
| E7-Pool-2 | A02-B07-B08-B35-E7 | E7(7-15) | HLA-A*02:01 | TLHEYMLDL (SEQ ID NO: 53) |
| | | E7(7-15) | HLA-B*07:02 | TLHEYMLDL |
| | | E7(7-15) | HLA-B*08:01 | TLHEYMLDL |
| | | E7(7-15) | HLA-B*35:01 | TLHEYMLDL |
| | B08-B07-B35-B57-E7 | E7(49-57) | HLA-B*07:02 | RAHYNIVTF (SEQ ID NO: 54) |
| | | E7(49-57) | HLA-B*08:01 | RAHYNIVTF |
| | | E7(49-57) | HLA-B*15:01 | RAHYNIVTF |
| | | E7(49-57) | HLA-B*57:01 | RAHYNIVTF |
| | | E7(49-57) | HLA-B*35:01 | RAHYNIVTF |
| | A02-E7-2 | E7(85-93) | HLA-A*02:01 | GTLGIVCPI (SEQ ID NO: 55) |
| | A03/A11-E7-2 | E7(89-97) | HLA-A*11:01 | IVCPICSQK (SEQ ID NO: 56) |
| | | E7(89-97) | HLA-A*03:01 | IVCPICSQK |
| | A24-E7-1 | E7(56-65) | HLA-A*24:02 | TFCCKCDSTL (SEQ ID NO: 57) |
| | B35-E7-2 | E7(44-53) | HLA-B*35:01 | QAEPDRAHY (SEQ ID NO: 58) |
| | E7 11-19 | E7(11-19) | HLA-A*02:01 | YMLDLQPET (SEQ ID NO: 59) |
| | E7 11-20 | E7(11-20) | HLA-A*02:01 | YMLDLQPETT (SEQ ID NO: 60) |

The occurrence of the disclosed HPV16-Antigens E2, E7, and E8 were examined in other HPV genomes by blasting the Papillomavirus database available from URL: pave.niaid.nih.gov/#home (see Tables 6-8).

TABLE 6

HPV16-Antigen E2 Blast Results

| Epitope | Locus ID/Description | Score | Query Coverage | E Value | Max ident |
|---|---|---|---|---|---|
| NTTPIVHLK (SEQ ID NO: 5) | Human papillomavirus 16 (HPV16), E2 protein | 21.9 | 100.00% | 1.9 | 100.00% |
| | Human papillomavirus 16 (HPV16), E8^E2 protein | 21.9 | 100.00% | 2.1 | 100.00% |
| | Human papillomavirus 18 (HPV18), E2 protein | 21.9 | 100.00% | 2.2 | 88.90% |
| | Human papillomavirus 97 (HPV97), E2 protein | 21.9 | 100.00% | 2.2 | 88.90% |
| | Human papillomavirus 45 (HPV45), E2 protein | 21.6 | 100.00% | 2.5 | 88.90% |
| | Human papillomavirus 39 (HPV39), E2 protein | 21.6 | 100.00% | 2.6 | 88.90% |
| | Human papillomavirus 97 (HPV97), E8^E2 protein | 21.6 | 100.00% | 2.7 | 88.90% |
| | Human papillomavirus 18 (HPV18), E8^E2 protein | 21.6 | 100.00% | 2.8 | 88.90% |
| | Human papillomavirus 59 (HPV59), E8^E2 protein | 21.2 | 100.00% | 3 | 88.90% |
| | Human papillomavirus 59 (HPV59), E2 protein | 21.2 | 100.00% | 3.1 | 88.90% |
| | Human papillomavirus 45 (HPV45), E8^E2 protein | 21.2 | 100.00% | 3.2 | 88.90% |
| | Human papillomavirus 39 (HPV39), E8^E2 protein | 21.2 | 100.00% | 3.2 | 88.90% |
| | Human papillomavirus 85 (HPV85), E2 protein | 21.2 | 100.00% | 3.7 | 88.90% |
| | Human papillomavirus 68 (HPV68), E2 protein | 20.8 | 100.00% | 3.9 | 88.90% |
| | Human papillomavirus 70 (HPV70), E2 protein | 20.8 | 100.00% | 4.3 | 88.90% |
| | Human papillomavirus 68 (HPV68), E8^E2 protein | 20.8 | 100.00% | 4.8 | 88.90% |
| | Human papillomavirus 70 (HPV70), E8^E2 protein | 20.8 | 100.00% | 5 | 88.90% |
| | Human papillomavirus 67 (HPV67), E2 protein | 20.8 | 100.00% | 5 | 88.90% |
| | Human papillomavirus 85 (HPV85), E8^E2 protein | 20.4 | 100.00% | 6.2 | 88.90% |
| | Human papillomavirus 67 (HPV67), E8^E2 protein | 20.4 | 100.00% | 6.3 | 88.90% |
| | Human papillomavirus 35 (HPV35), E8^E2 protein | 20 | 88.90% | 7 | 100.00% |

TABLE 6-continued

HPV16-Antigen E2 Blast Results

| Epitope | Locus ID/Description | Score | Query Coverage | E Value | Max ident |
|---|---|---|---|---|---|
| | Human papillomavirus 35 (HPV35), E2 protein | 20 | 88.90% | 7.3 | 100.00% |
| | Human papillomavirus 56 (HPV56), E2 protein | 19.6 | 88.90% | 9.7 | 87.50% |
| | Human papillomavirus 54 (HPV54), E2 protein | 19.6 | 100.00% | 10 | 77.80% |
| RLECAIYYK (SEQ ID NO: 4) | Human papillomavirus 16 (HPV16), E2 protein | 23.9 | 100.00% | 0.57 | 100.00% |
| | Human papillomavirus 91 (HPV91), E2 protein | 20.8 | 100.00% | 4 | 77.80% |
| | Human papillomavirus 35 (HPV35), E2 protein | 20.8 | 100.00% | 4.1 | 77.80% |
| | Human papillomavirus 67 (HPV67), E2 protein | 20.8 | 100.00% | 4.2 | 77.80% |
| | Human papillomavirus 43 (HPV43), E2 protein | 20.8 | 100.00% | 5 | 77.80% |
| | Human papillomavirus 54 (HPV54), E2 protein | 20 | 100.00% | 6.6 | 77.80% |
| | Human papillomavirus 26 (HPV26), E2 protein | 20 | 100.00% | 7.8 | 77.80% |
| | Human papillomavirus 69 (HPV69), E2 protein | 19.6 | 100.00% | 9.9 | 77.80% |
| VYLTAPTGCI (SEQ ID NO: 6) | Human papillomavirus 16 (HPV16), E2 protein | 26.2 | 100.00% | 0.13 | 100.00% |
| | Human papillomavirus 31 (HPV31), E2 protein | 23.5 | 100.00% | 0.8 | 80.00% |
| VVEGQVDYY (SEQ ID NO: 9) | Human papillomavirus 16 (HPV16), E2 protein | 22.7 | 100.00% | 1 | 100.00% |
| | Human papillomavirus 52 (HPV52), E2 protein | 22.3 | 100.00% | 1.6 | 88.90% |
| | Human papillomavirus 113 (HPV113), E2 protein | 20.8 | 88.90% | 4.2 | 87.50% |
| | Human papillomavirus 111 (HPV111), E2 protein | 20.8 | 88.90% | 4.5 | 87.50% |
| | Human papillomavirus 122 (HPV122), E2 protein | 20.4 | 88.90% | 5.3 | 87.50% |
| | Human papillomavirus 37 (HPV37), E2 protein | 20.4 | 88.90% | 6 | 87.50% |
| YLTAPTGCI (SEQ ID NO: 18) | Human papillomavirus 16 (HPV16), E2 protein | 24.3 | 100.00% | 0.38 | 100.00% |
| | Human papillomavirus 31 (HPV31), E2 protein | 23.1 | 100.00% | 0.99 | 88.90% |
| QVILCPTSV (SEQ ID NO: 19) | Human papillomavirus 16 (HPV16), E2 protein | 22.7 | 100.00% | 1.2 | 100.00% |
| | Human papillomavirus 33 (HPV33), E2 protein | 20 | 100.00% | 8 | 77.80% |
| TLKCLRYRFK (SEQ ID NO: 20) | Human papillomavirus 16 (HPV16), E8^E2 protein | 26.6 | 100.00% | 0.1 | 100.00% |
| | Human papillomavirus 26 (HPV26), E8^E2 protein | 25.8 | 100.00% | 0.16 | 90.00% |
| | Human papillomavirus 97 (HPV97), E2 protein | 24.6 | 100.00% | 0.31 | 90.00% |
| | Human papillomavirus 26 (HPV26), E2 protein | 24.6 | 100.00% | 0.33 | 90.00% |
| | Human papillomavirus 100 (HPV100), E2 protein | 24.3 | 100.00% | 0.4 | 80.00% |
| | Human papillomavirus 97 (HPV97), E8^E2 protein | 24.3 | 100.00% | 0.48 | 90.00% |
| | Human papillomavirus 69 (HPV69), E8^E2 protein | 24.3 | 90.00% | 0.51 | 100.00% |
| | Human papillomavirus 22 (HPV22), E2 protein | 23.9 | 100.00% | 0.53 | 80.00% |
| | Human papillomavirus 22 (HPV22), E8^E2 protein | 23.9 | 100.00% | 0.53 | 80.00% |
| | Human papillomavirus 151 (HPV151), E2 protein | 23.9 | 100.00% | 0.53 | 80.00% |
| | Human papillomavirus 38 (HPV38), E2 protein | 23.9 | 100.00% | 0.57 | 80.00% |
| | Human papillomavirus 151 (HPV151), E8^E2 protein | 23.9 | 100.00% | 0.6 | 80.00% |
| | Human papillomavirus 23 (HPV23), E2 protein | 23.9 | 100.00% | 0.61 | 80.00% |
| | Human papillomavirus 100 (HPV100), E8^E2 protein | 23.5 | 100.00% | 0.67 | 80.00% |
| | Human papillomavirus 38 (HPV38), E8^E2 protein | 23.5 | 100.00% | 0.75 | 80.00% |
| | Human papillomavirus 23 (HPV23), E8^E2 protein | 23.1 | 100.00% | 0.88 | 80.00% |
| | Human papillomavirus 82 (HPV82), E8^E2 protein | 23.1 | 80.00% | 0.89 | 100.00% |
| | Human papillomavirus 133 (HPV133), E2 protein | 23.1 | 100.00% | 1 | 90.00% |
| | Human papillomavirus 69 (HPV69), E2 protein | 23.1 | 90.00% | 1.1 | 100.00% |
| | Human papillomavirus 133 (HPV133), E8^E2 protein | 22.7 | 100.00% | 1.1 | 90.00% |
| | Human papillomavirus 1 (HPV1), E2 protein | 22.7 | 90.00% | 1.2 | 88.90% |
| | Human papillomavirus 1 (HPV1), E8^E2 protein | 22.7 | 90.00% | 1.2 | 88.90% |
| | Human papillomavirus 106 (HPV106), E2 protein | 22.7 | 90.00% | 1.2 | 88.90% |
| | Human papillomavirus 106 (HPV106), E8^E2 protein | 22.7 | 90.00% | 1.2 | 88.90% |
| | Human papillomavirus 33 (HPV33), E8^E2 protein | 22.7 | 100.00% | 1.3 | 80.00% |
| | Human papillomavirus 121 (HPV121), E2 protein | 22.7 | 100.00% | 1.4 | 80.00% |
| | Human papillomavirus 63 (HPV63), E2 protein | 22.7 | 90.00% | 1.5 | 88.90% |
| | Human papillomavirus 33 (HPV33), E2 protein | 22.7 | 100.00% | 1.5 | 80.00% |
| | Human papillomavirus 58 (HPV58), E2 protein | 22.7 | 100.00% | 1.5 | 80.00% |
| | Human papillomavirus 180 (HPV180), E8^E2 protein | 22.3 | 100.00% | 1.6 | 80.00% |
| | Human papillomavirus 180 (HPV180), E2 protein | 22.3 | 100.00% | 1.6 | 80.00% |
| | Human papillomavirus 204 (HPV204), E2 protein | 22.3 | 90.00% | 1.6 | 88.90% |
| | Human papillomavirus 52 (HPV52), E2 protein | 22.3 | 100.00% | 1.7 | 80.00% |
| | Human papillomavirus 18 (HPV18), E2 protein | 22.3 | 100.00% | 1.7 | 70.00% |
| | Human papillomavirus 45 (HPV45), E2 protein | 22.3 | 100.00% | 1.9 | 70.00% |
| | Human papillomavirus 121 (HPV121), E8^E2 protein | 22.3 | 100.00% | 1.9 | 80.00% |
| | Human papillomavirus 53 (HPV53), E8^E2 protein | 22.3 | 90.00% | 1.9 | 88.90% |
| | Human papillomavirus 204 (HPV204), E8^E2 protein | 22.3 | 90.00% | 1.9 | 88.90% |
| | Human papillomavirus 120 (HPV120), E2 protein | 21.9 | 100.00% | 1.9 | 70.00% |
| | Human papillomavirus 120 (HPV120), E8^E2 protein | 21.9 | 100.00% | 1.9 | 70.00% |
| | Human papillomavirus 18 (HPV18), E8^E2 protein | 21.9 | 100.00% | 2.3 | 70.00% |
| | Human papillomavirus 58 (HPV58), E8^E2 protein | 21.9 | 100.00% | 2.3 | 80.00% |
| | Human papillomavirus 63 (HPV63), E8^E2 protein | 21.9 | 90.00% | 2.3 | 88.90% |
| | Human papillomavirus 82 (HPV82), E2 protein | 21.9 | 80.00% | 2.4 | 100.00% |
| | Human papillomavirus 53 (HPV53), E2 protein | 21.9 | 90.00% | 2.5 | 88.90% |
| | Human papillomavirus 62 (HPV62), E8^E2 protein | 21.9 | 90.00% | 2.5 | 77.80% |

TABLE 6-continued

HPV16-Antigen E2 Blast Results

| Epitope | Locus ID/Description | Score | Query Coverage | E Value | Max ident |
|---|---|---|---|---|---|
| | Human papillomavirus 81 (HPV81), E2 protein | 21.9 | 90.00% | 2.5 | 77.80% |
| | Human papillomavirus 81 (HPV81), E8^E2 protein | 21.9 | 90.00% | 2.5 | 77.80% |
| | Human papillomavirus 77 (HPV77), E8^E2 protein | 21.9 | 100.00% | 2.5 | 70.00% |
| | Human papillomavirus 67 (HPV67), E2 protein | 21.6 | 100.00% | 2.6 | 80.00% |
| | Human papillomavirus 52 (HPV52), E8^E2 protein | 21.6 | 100.00% | 2.7 | 80.00% |
| | Human papillomavirus 77 (HPV77), E2 protein | 21.6 | 100.00% | 2.9 | 70.00% |
| | Human papillomavirus 45 (HPV45), E8^E2 protein | 21.6 | 100.00% | 3 | 70.00% |
| | Human papillomavirus 110 (HPV110), E2 protein | 21.6 | 100.00% | 3.1 | 80.00% |
| | Human papillomavirus 86 (HPV86), E2 protein | 21.6 | 90.00% | 3.2 | 77.80% |
| | Human papillomavirus 86 (HPV86), E8^E2 protein | 21.6 | 90.00% | 3.2 | 77.80% |
| | Human papillomavirus 62 (HPV62), E2 protein | 21.6 | 90.00% | 3.2 | 77.80% |
| | Human papillomavirus 67 (HPV67), E8^E2 protein | 21.2 | 100.00% | 3.3 | 80.00% |
| | Human papillomavirus 59 (HPV59), E8^E2 protein | 21.2 | 90.00% | 3.4 | 77.80% |
| | Human papillomavirus 89 (HPV89), E2 protein | 21.2 | 90.00% | 3.4 | 77.80% |
| | Human papillomavirus 89 (HPV89), E8^E2 protein | 21.2 | 90.00% | 3.4 | 77.80% |
| | Human papillomavirus 96 (HPV96), E2 protein | 21.2 | 100.00% | 3.5 | 80.00% |
| | Human papillomavirus 59 (HPV59), E2 protein | 21.2 | 90.00% | 3.6 | 77.80% |
| | Human papillomavirus 108 (HPV108), E2 protein | 21.2 | 100.00% | 3.7 | 80.00% |
| | Human papillomavirus 71 (HPV71), E8^E2 protein | 21.2 | 90.00% | 3.8 | 77.80% |
| | Human papillomavirus 139 (HPV139), E2 protein | 21.2 | 100.00% | 4 | 80.00% |
| | Human papillomavirus 155 (HPV155), E2 protein | 21.2 | 100.00% | 4 | 80.00% |
| | Human papillomavirus 110 (HPV110), E8^E2 protein | 21.2 | 100.00% | 4 | 80.00% |
| | Human papillomavirus 66 (HPV66), E8^E2 protein | 21.2 | 90.00% | 4.1 | 77.80% |
| | Human papillomavirus 35 (HPV35), E2 protein | 21.2 | 90.00% | 4.3 | 88.90% |
| | Human papillomavirus 71 (HPV71), E2 protein | 21.2 | 90.00% | 4.3 | 77.80% |
| | Human papillomavirus 56 (HPV56), E8^E2 protein | 20.8 | 90.00% | 4.4 | 77.80% |
| | Human papillomavirus 92 (HPV92), E2 protein | 20.8 | 100.00% | 4.4 | 80.00% |
| | Human papillomavirus 96 (HPV96), E8^E2 protein | 20.8 | 100.00% | 4.6 | 80.00% |
| | Human papillomavirus 35 (HPV35), E8^E2 protein | 20.8 | 90.00% | 4.8 | 88.90% |
| | Human papillomavirus 34 (HPV34), E2 protein | 20.8 | 80.00% | 5.2 | 87.50% |
| | Human papillomavirus 51 (HPV51), E8^E2 protein | 20.8 | 80.00% | 5.2 | 87.50% |
| | Human papillomavirus 42 (HPV42), E8^E2 protein | 20.8 | 90.00% | 5.3 | 77.80% |
| | Human papillomavirus 108 (HPV108), E8^E2 protein | 20.8 | 100.00% | 5.5 | 80.00% |
| | Human papillomavirus 39 (HPV39), E8^E2 protein | 20.8 | 90.00% | 5.6 | 77.80% |
| | Human papillomavirus 39 (HPV39), E2 protein | 20.4 | 90.00% | 5.8 | 77.80% |
| | Human papillomavirus 68 (HPV68), E2 protein | 20.4 | 90.00% | 5.9 | 77.80% |
| | Human papillomavirus 34 (HPV34), E8^E2 protein | 20.4 | 80.00% | 5.9 | 87.50% |
| | Human papillomavirus 51 (HPV51), E2 protein | 20.4 | 80.00% | 5.9 | 87.50% |
| | Human papillomavirus 155 (HPV155), E8^E2 protein | 20.4 | 100.00% | 6 | 80.00% |
| | Human papillomavirus 70 (HPV70), E2 protein | 20.4 | 90.00% | 6.1 | 77.80% |
| | Human papillomavirus 42 (HPV42), E2 protein | 20.4 | 90.00% | 6.1 | 77.80% |
| | Human papillomavirus 139 (HPV139), E8^E2 protein | 20.4 | 100.00% | 6.5 | 80.00% |
| | Human papillomavirus 150 (HPV150), E2 protein | 20.4 | 100.00% | 6.7 | 80.00% |
| | Human papillomavirus 66 (HPV66), E2 protein | 20.4 | 90.00% | 6.9 | 77.80% |
| | Human papillomavirus 85 (HPV85), E8^E2 protein | 20.4 | 90.00% | 6.9 | 77.80% |
| | Human papillomavirus 92 (HPV92), E8^E2 protein | 20.4 | 100.00% | 7.1 | 80.00% |
| | Human papillomavirus 41 (HPV41), E2 protein | 20 | 100.00% | 7.4 | 60.00% |
| | Human papillomavirus 56 (HPV56), E2 protein | 20 | 90.00% | 7.6 | 77.80% |
| | Human papillomavirus 85 (HPV85), E2 protein | 20 | 90.00% | 7.6 | 77.80% |
| | Human papillomavirus 109 (HPV109), E2 protein | 20 | 100.00% | 7.7 | 80.00% |
| | Human papillomavirus 68 (HPV68), E8^E2 protein | 20 | 90.00% | 7.9 | 77.80% |
| RYRFKKHCTL (SEQ ID NO: 21) | Human papillomavirus 16 (HPV16), E2 protein | 25.8 | 100.00% | 0.16 | 100.00% |
| | Human papillomavirus 16 (HPV16), E8^E2 protein | 25.4 | 100.00% | 0.18 | 100.00% |
| | Human papillomavirus 26 (HPV26), E8^E2 protein | 20.8 | 70.00% | 4.7 | 100.00% |
| | Human papillomavirus 69 (HPV69), E8^E2 protein | 20 | 70.00% | 7.6 | 100.00% |
| | Human papillomavirus 156 (HPV156), E2 protein | 20 | 100.00% | 9 | 70.00% |
| | Human papillomavirus 26 (HPV26), E2 protein | 20 | 70.00% | 9.4 | 100.00% |
| YYVHEGIRTY (SEQ ID NO: 24) | Human papillomavirus 2 (HPV2), E2 protein | 21.2 | 80.00% | 3.6 | 75.00% |
| | Human papillomavirus 35 (HPV35), E2 protein | 20.8 | 100.00% | 4.5 | 70.00% |
| | Human papillomavirus 106 (HPV106), E2 protein | 20.4 | 80.00% | 6.3 | 87.50% |
| | Human papillomavirus 71 (HPV71), E2 protein | 20 | 80.00% | 7.6 | 75.00% |
| | Human papillomavirus 44 (HPV44), E2 protein | 19.6 | 100.00% | 10 | 70.00% |

TABLE 7

HPV16-Antigen E6 Blast Results

| Epitope | Locus ID/Description | Score | Query Coverage | E Value | Max ident |
|---|---|---|---|---|---|
| IVYRDGNPY (SEQ ID NO: 28) | Human papillomavirus 58 (HPV58), E6 protein | 24.3 | 100.00% | 0.35 | 88.90% |
| | Human papillomavirus 52 (HPV52), E6 protein | 23.1 | 100.00% | 0.89 | 88.90% |
| | Human papillomavirus 51 (HPV51), E6 protein | 23.1 | 100.00% | 0.91 | 88.90% |
| | Human papillomavirus 53 (HPV53), E6 protein | 21.9 | 100.00% | 1.8 | 77.80% |
| | Human papillomavirus 33 (HPV33), E6 protein | 21.9 | 100.00% | 1.9 | 66.70% |
| | Human papillomavirus 67 (HPV67), E6 protein | 21.6 | 100.00% | 2.4 | 88.90% |
| | Human papillomavirus 35 (HPV35), E6 protein | 21.6 | 100.00% | 2.9 | 77.80% |
| | Human papillomavirus 70 (HPV70), E6 protein | 21.2 | 100.00% | 3.1 | 77.80% |
| | Human papillomavirus 85 (HPV85), E6 protein | 20.8 | 100.00% | 4.7 | 77.80% |
| | Human papillomavirus 82 (HPV82), E6 protein | 20.4 | 100.00% | 5.5 | 77.80% |
| KLPQLCTEL (SEQ ID NO: 29) | Human papillomavirus 16 (HPV16), E6 protein | 21.6 | 100.00% | 2.7 | 100.00% |
| | Human papillomavirus 16 (HPV16), E6* protein | 21.6 | 100.00% | 2.7 | 100.00% |
| | Human papillomavirus 45 (HPV45), E6 protein | 20 | 100.00% | 8 | 88.90% |
| | Human papillomavirus 97 (HPV97), E6 protein | 20 | 100.00% | 8 | 88.90% |
| | Human papillomavirus 18 (HPV18), E6 protein | 20 | 100.00% | 8.2 | 88.90% |
| | Human papillomavirus 45 (HPV45), E6* protein | 19.6 | 100.00% | 8.7 | 88.90% |
| | Human papillomavirus 97 (HPV97), E6* protein | 19.6 | 100.00% | 8.9 | 88.90% |
| | Human papillomavirus 18 (HPV18), E6* protein | 19.6 | 100.00% | 9.2 | 88.90% |
| RPRKLPQLCT (SEQ ID NO: 30) | Human papillomavirus 16 (HPV16), E6 protein | 24.3 | 100.00% | 0.5 | 100.00% |
| | Human papillomavirus 70 (HPV70), E6 protein | 20.4 | 100.00% | 6 | 80.00% |
| | Human papillomavirus 18 (HPV18), E6 protein | 20.4 | 100.00% | 6.2 | 80.00% |
| | Human papillomavirus 97 (HPV97), E6* protein | 20.4 | 100.00% | 6.2 | 80.00% |
| | Human papillomavirus 97 (HPV97), E6 protein | 20.4 | 100.00% | 6.4 | 80.00% |
| | Human papillomavirus 18 (HPV18), E6* protein | 20.4 | 100.00% | 6.6 | 80.00% |
| | Human papillomavirus 45 (HPV45), E6 protein | 20.4 | 100.00% | 6.7 | 80.00% |
| | Human papillomavirus 70 (HPV70), E6* protein | 20.4 | 100.00% | 6.9 | 80.00% |
| | Human papillomavirus 45 (HPV45), E6* protein | 20 | 100.00% | 7.4 | 80.00% |
| | Human papillomavirus 39 (HPV39), E6* protein | 20 | 100.00% | 7.5 | 80.00% |
| | Human papillomavirus 39 (HPV39), E6 protein | 20 | 100.00% | 7.9 | 80.00% |
| NPYAVCDKCL (SEQ ID NO: 35) | Human papillomavirus 51 (HPV51), E6 protein | 21.6 | 100.00% | 2.6 | 80.00% |
| VCDKCLKFY (SEQ ID NO: 37) | Human papillomavirus 31 (HPV31), E6 protein | 19.6 | 100.00% | 9 | 77.80% |
| | Human papillomavirus 31 (HPV31), E6 protein | 23.1 | 100.00% | 0.83 | 100.00% |
| | Human papillomavirus 16 (HPV16), E6 protein | 23.1 | 100.00% | 1 | 100.00% |
| | Human papillomavirus 67 (HPV67), E6 protein | 20.8 | 100.00% | 4.3 | 77.80% |
| | Human papillomavirus 16 (HPV16), E6* protein | 23.9 | 100.00% | 0.51 | 100.00% |

TABLE 7-continued

HPV16-Antigen E6 Blast Results

| Epitope | Locus ID/Description | Score | Query Coverage | E Value | Max ident |
|---|---|---|---|---|---|
| CVYCKQQLLR (SEQ ID NO: 40) | Human papillomavirus 16 (HPV16), E6 protein | 23.5 | 100.00% | 0.77 | 100.00% |
| | Human papillomavirus 35 (HPV35), E6* protein | 20.8 | 100.00% | 4.5 | 80.00% |
| | Human papillomavirus 56 (HPV56), E6* protein | 20.4 | 100.00% | 5.8 | 70.00% |
| | Human papillomavirus 35 (HPV35), E6 protein | 20 | 100.00% | 7.8 | 80.00% |
| | Human papillomavirus 68 (HPV68), E6* protein | 19.6 | 100.00% | 9.7 | 70.00% |
| DKKQRFHNI (SEQ ID NO: 41) | Human papillomavirus 31 (HPV31), E6 protein | 21.9 | 100.00% | 2 | 88.90% |
| | Human papillomavirus 16 (HPV16), E6 protein | 21.2 | 100.00% | 3.1 | 100.00% |
| | Human papillomavirus 67 (HPV67), E6 protein | 19.6 | 100.00% | 9.7 | 77.80% |
| FAFRDLCIV (SEQ ID NO: 42) | Human papillomavirus 16 (HPV16), E6 protein | 22.3 | 100.00% | 1.6 | 100.00% |
| | Human papillomavirus 45 (HPV45), E6 protein | 20.4 | 100.00% | 5.3 | 88.90% |
| | human papillomavirus 73 (HPV73), E6 protein | 20 | 100.00% | 8.2 | 88.90% |
| LLIRCINCQK (SEQ ID NO: 43) | Human papillomavirus 16 (HPV16), E6 protein | 23.5 | 100.00% | 0.81 | 100.00% |
| | Human papillomavirus 35 (HPV35), E6 protein | 21.2 | 100.00% | 3.5 | 90.00% |
| | Human papillomavirus 97 (HPV97), E6 protein | 20.8 | 100.00% | 5 | 80.00% |
| | Human papillomavirus 18 (HPV18), E6 protein | 20.4 | 100.00% | 6.3 | 80.00% |
| | Human papillomavirus 45 (HPV45), E6 protein | 20.4 | 100.00% | 6.9 | 80.00% |
| | Human papillomavirus 31 (HPV31), E6 protein | 20 | 100.00% | 8.9 | 80.00% |

TABLE 8

HPV16-Antigen E7 Blast Results

| Epitope | Locus ID/Description | Score | Query Coverage | E Value | Max ident |
|---|---|---|---|---|---|
| LQPETTDLY (SEQ ID NO: 46) | Human papillomavirus 16 (HPV16), E7 protein | 21.9 | 100.00% | 2 | 100.00% |
| | Human papillomavirus 67 (HPV67), E7 protein | 20.8 | 100.00% | 4.8 | 88.90% |
| | Human papillomavirus 52 (HPV52), E7 protein | 20.4 | 100.00% | 5.6 | 88.90% |
| LLMGTLGIV (SEQ ID NO: 48) | Human papillomavirus 73 (HPV73), E7 protein | 21.6 | 100.00% | 2.6 | 100.00% |
| HYNIVTFCCK (SEQ ID NO: 49) | Human papillomavirus 16 (HPV16), E7 protein | 25.8 | 100.00% | 0.15 | 100.00% |
| | Human papillomavirus 31 (HPV31), E7 protein | 22.7 | 100.00% | 1.3 | 80.00% |
| | Human papillomavirus 35 (HPV35), E7 protein | 20 | 100.00% | 8.1 | 80.00% |
| GIVCPICSQK (SEQ ID NO: 50) | Human papillomavirus 16 (HPV16), E7 protein | 23.9 | 100.00% | 0.62 | 100.00% |
| | Human papillomavirus 67 (HPV67), E7 protein | 20 | 100.00% | 8.4 | 70.00% |
| QPETTDLYCY (SEQ ID NO: 52) | Human papillomavirus 16 (HPV16), E7 protein | 25 | 100.00% | 0.23 | 100.00% |
| | Human papillomavirus 52 (HPV52), E7 protein | 24.3 | 100.00% | 0.49 | 90.00% |

TABLE 8-continued

HPV16-Antigen E7 Blast Results

| Epitope | Locus ID/Description | Score | Query Coverage | E Value | Max ident |
|---|---|---|---|---|---|
| | Human papillomavirus 67 (HPV67), E7 protein | 23.9 | 100.00% | 0.53 | 90.00% |
| | Human papillomavirus 35 (HPV35), E7 protein | 22.7 | 100.00% | 1.5 | 80.00% |
| | Human papillomavirus 31 (HPV31), E7 protein | 22.3 | 100.00% | 1.6 | 80.00% |
| | Human papillomavirus 71 (HPV71), E7 protein | 21.2 | 100.00% | 3.5 | 70.00% |
| | Human papillomavirus 33 (HPV33), E7 protein | 21.2 | 90.00% | 4.3 | 88.90% |
| | Human papillomavirus 58 (HPV58), E7 protein | 20 | 100.00% | 9 | 70.00% |
| GTLGIVCPI (SEQ ID NO: 55) | Human papillomavirus 16 (HPV16), E7 protein | 22.7 | 100.00% | 1.2 | 100.00% |
| | Human papillomavirus 73 (HPV73), E7 protein | 21.6 | 88.90% | 2.3 | 100.00% |
| | Human papillomavirus 6 (HPV6), E7 protein | 20 | 100.00% | 7 | 88.90% |
| | Human papillomavirus 11 (HPV11), E7 protein | 20 | 100.00% | 7.2 | 88.90% |
| | Human papillomavirus 7 (HPV7), E7 protein | 20 | 88.90% | 7.6 | 87.50% |
| | Human papillomavirus 106 (HPV106), E7 protein | 19.6 | 88.90% | 10 | 87.50% |
| TFCCKCDSTL (SEQ ID NO: 57) | Human papillomavirus 31 (HPV31), E7 protein | 20.8 | 100.00% | 5.2 | 80.00% |
| YMLDLQPET (SEQ ID NO: 59) | Human papillomavirus 16 (HPV16), E7 protein | 22.3 | 100.00% | 1.4 | 100.00% |
| | Human papillomavirus 52 (HPV52), E7 protein | 21.2 | 100.00% | 3.5 | 88.90% |
| | Human papillomavirus 67 (HPV67), E7 protein | 19.6 | 100.00% | 9.9 | 77.80% |
| YMLDLQPETT (SEQ ID NO: 60) | Human papillomavirus 16 (HPV16), E7 protein | 24.3 | 100.00% | 0.5 | 100.00% |
| | Human papillomavirus 52 (HPV52), E7 protein | 22.7 | 100.00% | 1.2 | 90.00% |
| | Human papillomavirus 67 (HPV67), E7 protein | 21.2 | 100.00% | 3.5 | 80.00% |
| | Human papillomavirus 31 (HPV31), E7 protein | 20.8 | 100.00% | 4.4 | 80.00% |
| | Human papillomavirus 35 (HPV35), E7 protein | 19.6 | 100.00% | 9.8 | 70.00% |

For reasons of completeness, various aspects of the invention are set out in the following numbered clauses, as well as the following claims:

Clause 1. An immunogenic composition for treating a subject having a HPV16-associated disease, the composition comprising at least one synthetic polypeptide encoding a cytotoxic T lymphocyte (CTL) epitope derived from E2, E6, or E7 human papillomavirus subtype 16 (HPV16) antigens, and a pharmaceutically acceptable carrier or excipient.

Clause 2. The immunogenic composition of clause 1, wherein the HPV16-associated disease is selected from the group consisting of cervical cancers, anal cancers, head and neck cancers, vaginal cancers, vulvar cancers, penile cancers, and rectal cancers.

Clause 3. The immunogenic composition of clause 2, wherein the HPV16-associated disease is a head and neck squamous cell carcinoma (HNSCC).

Clause 4. The immunogenic composition of clause 1, wherein the at least one synthetic polypeptide encodes a CTL epitope from the HPV16 E2 antigen.

Clause 5. The immunogenic composition of clause 4, wherein the CTL epitope from the HPV16 E2 antigen is selected from the group consisting of RLECAIYYK (SEQ ID NO:4), VYLTAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAPILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24).

Clause 6. The immunogenic composition of clause 1, wherein the at least one synthetic polypeptide encodes a CTL epitope from the HPV16 E6 antigen.

Clause 7. The immunogenic composition of clause 6, wherein the CTL epitope from the HPV16 E6 antigen is selected from the group consisting of IILECVYCK (SEQ ID NO:26), ISEYRHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43).

Clause 8. The immunogenic composition of clause 1, wherein the at least one synthetic polypeptide encodes a CTL epitope from the HPV16 E7 antigen.

Clause 9. The immunogenic composition of clause 8, wherein the CTL epitope from the HPV16 E7 antigen is selected from the group consisting of LQPETTDLY (SEQ ID NO:46), HGDTPTLHEY (SEQ ID NO:47), TPTLHEYML (SEQ ID NO:51), and QPETTDLYCY (SEQ ID NO:52).

Clause 10. A method of treating a subject having a HPV16-associated disease, the method comprising administering an immunogenic composition comprising at least one synthetic polypeptide encoding a cytotoxic T lymphocyte (CTL) epitope derived from E2, E6, or E7 human papillomavirus subtype 16 (HPV16) antigens, and a pharmaceutically acceptable carrier or excipient; wherein administration of the composition to the subject induces an immune response against the HPV16-associated disease and treats the subject.

Clause 11. The method of clause 10, wherein the HPV16-associated disease is selected from the group consisting of cervical cancers, anal cancers, head and neck cancers, vaginal cancers, vulvar cancers, penile cancers, and rectal cancers.

Clause 12. The method of clause 11, wherein the HPV16-associated disease is a head and neck squamous cell carcinoma (HNSCC).

Clause 13. The method of clause 10, wherein the at least one synthetic polypeptide encodes a CTL epitope from the HPV16 E2 antigen.

Clause 14. The method of clause 13, wherein the CTL epitope from the HPV16 E2 antigen is selected from the group consisting of RLECAIYYK (SEQ ID NO:4), VYLTAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAPILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24).

Clause 15. The method of clause 10, wherein the at least one synthetic polypeptide encodes a CTL epitope from the HPV16 E6 antigen.

Clause 16. The method of clause 15, wherein the CTL epitope from the HPV16 E6 antigen is selected from the group consisting of IILECVYCK (SEQ ID NO:26), ISEYRHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43).

Clause 17. The method of clause 10, wherein the at least one synthetic polypeptide encodes a CTL epitope from the HPV16 E7 antigen.

Clause 18. The method of clause 17, wherein the CTL epitope from the HPV16 E7 antigen is selected from the group consisting of LQPETTDLY (SEQ ID NO:46), HGDTPTLHEY (SEQ ID NO:47), TPTLHEYML (SEQ ID NO:51), and QPETTDLYCY (SEQ ID NO:52).

Clause 19. The method of clause 10, wherein the immunogenic composition further comprises an immune checkpoint inhibitor.

Clause 20. The method of clause 19, wherein the immune checkpoint inhibitor is a programmed cell death protein 1 (PD-1) inhibitor.

Clause 21. The method of clause 10, wherein the immunogenic composition further comprises an Indoleamine 2,3-dioxygenase 1 (IDO-1) inhibitor.

Clause 22. An immune cell comprising a T-cell receptor (TCR) capable of binding a synthetic polypeptide encoding a cytotoxic T lymphocyte (CTL) epitope derived from E2, E6, or E7 human papillomavirus subtype 16 (HPV16) antigens; wherein the CTL epitope from the HPV16 E2 antigen is selected from the group consisting of RLECAIYYK (SEQ ID NO:4), VYLTAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAPILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24); wherein the CTL epitope from the HPV16 E6 antigen is selected from the group consisting of IILECVYCK (SEQ ID NO:26), ISEYRHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43); and wherein the CTL epitope from the HPV16 E7 antigen is selected from the group consisting of LQPETTDLY (SEQ ID NO:46), HGDTPTLHEY (SEQ ID NO:47), TPTLHEYML (SEQ ID NO:51), and QPETTDLYCY (SEQ ID NO:52).

Clause 23. A method of detecting an HPV16-associated disease in a subject, the method comprising obtaining a biological sample from a subject, wherein the biological sample comprises T cells; contacting the biological sample with a MHC class I peptide tetramer composition comprising at least one synthetic MHC class I molecule and at least one synthetic polypeptide encoding a cytotoxic T lymphocyte (CTL) epitope derived from E2, E6, or E7 human papillomavirus subtype 16 (HPV16) antigens, wherein the at least one synthetic MHC class I molecule is bound to the at least one synthetic polypeptide encoding the CTL epitope derived from E2, E6, or E7 HPV16 antigens; detecting the presence of T cells bound to the synthetic polypeptide encoding the CTL epitope derived from E2, E6, or E7 HPV16 antigens.

Clause 24. The method of clause 23, wherein detecting the presence of T cells comprises flow cytometry or fluorescence-activated cell sorting.

Clause 25. The method of clause 23, wherein the at least one synthetic peptide encodes a CTL epitope from the HPV16 E2 antigen.

Clause 26. The method of clause 25, wherein the CTL epitope from the HPV16 E2 antigen is selected from the group consisting of RLECAIYYK (SEQ ID NO:4), VYLTAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAPILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24).

Clause 27. The method of clause 23, wherein the at least one synthetic peptide encodes CTL epitope from the HPV16 E6 antigen.

Clause 28. The method of clause 27, wherein the CTL epitope from the HPV16 E6 antigen is selected from the group consisting of IILECVYCK (SEQ ID NO:26), ISEYRHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43).

Clause 29. The method of clause 23, wherein the at least one synthetic peptide encodes a CTL epitope from the HPV16 E7 antigen.

Clause 30. The method of clause 29, wherein the CTL epitope from the HPV16 E7 antigen is selected from the group consisting of LQPETTDLY (SEQ ID NO:46), HGDTPTLHEY (SEQ ID NO:47), TPTLHEYML (SEQ ID NO:51), and QPETTDLYCY (SEQ ID NO:52).

Clause 31. The method of clause 23, wherein the MHC class I peptide tetramer composition further comprises a ligand.

Clause 32. The method of clause 23, wherein the MHC class I peptide tetramer composition further comprises a label.

Clause 33. The method of clause 32, wherein the label comprises a fluorescent molecule, a luminescent molecule, or a radioactive molecule.

Clause 34. The method of clause 23, wherein the MHC class I molecule comprises a self-assembling protein domain.

Clause 35. An immunogenic composition for treating a subject having a human papillomavirus (HPV)-associated disease, the composition comprising at least one synthetic polypeptide encoding a cytotoxic T lymphocyte (CTL) epitope derived from E2, E6, or E7 human papillomavirus subtype 16 (HPV16) antigens, and a pharmaceutically acceptable carrier or excipient.

Clause 36. The immunogenic composition of clause 35, wherein the HPV-associated disease is selected from the group consisting of cervical cancers, anal cancers, head and neck cancers, vaginal cancers, vulvar cancers, penile cancers, and rectal cancers.

Clause 37. The immunogenic composition of clause 35 or 36, wherein the HPV-associated disease is a head and neck squamous cell carcinoma (HNSCC).

Clause 38. The immunogenic composition of any one of clauses 35-37, wherein the HPV-associated disease is caused by HPV subtype 1, HPV subtype 2, HPV subtype 6, HPV subtype 7, HPV subtype 11, HPV subtype 16, HPV subtype 18, HPV subtype 22, HPV subtype 23, HPV subtype 26, HPV subtype 31, HPV subtype 33, HPV subtype 34, HPV subtype 35, HPV subtype 37, HPV subtype 38, HPV subtype 39, HPV subtype 41, HPV subtype 42, HPV subtype 43, HPV subtype 44, HPV subtype 45, HPV subtype 51, HPV subtype 52, HPV subtype 53, HPV subtype 54, HPV subtype 56, HPV subtype 58, HPV subtype 59, HPV subtype 62, HPV subtype 63, HPV subtype 66, HPV subtype 67, HPV subtype 68, HPV subtype 69, HPV subtype 70, HPV subtype 71, HPV subtype 73, HPV subtype 77, HPV subtype 81, HPV subtype 82, HPV subtype 85, HPV subtype 86, HPV subtype 89, HPV subtype 91, HPV subtype 92, HPV subtype 96, HPV subtype 97, HPV subtype 100, HPV subtype 106, HPV subtype 108, HPV subtype 109, HPV subtype 110, HPV subtype 111, HPV subtype 113, HPV subtype 120, HPV subtype 121, HPV subtype 122, HPV subtype 133, HPV subtype 139, HPV subtype 150, HPV subtype 151, HPV subtype 155, HPV subtype 156, HPV subtype 180, or HPV subtype 204.

Clause 39. The immunogenic composition of any one of clauses 35-38, wherein the at least one synthetic polypeptide encodes a CTL epitope from the HPV16 E2 antigen.

Clause 40. The immunogenic composition of clause 39, wherein the CTL epitope from the HPV16 E2 antigen is selected from the group consisting of RLECAIYYK (SEQ ID NO:4), VYLTAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAPILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24).

Clause 41. The immunogenic composition of clause 39 or 40, wherein the HPV-associated disease is caused by HPV1, HPV2, HPV16, HPV18, HPV22, HPV23, HPV26, HPV31, HPV33, HPV34, HPV35, HPV37, HPV38, HPV39, HPV41, HPV42, HPV43, HPV44, HPV45, HPV51, HPV52, HPV53, HPV54, HPV56, HPV59, HPV62, HPV63, HPV66, HPV67, HPV68, HPV69, HPV70, HPV71, HPV77, HPV81, HPV82, HPV85, HPV86, HPV89, HPV91, HPV92, HPV96, HPV97, HPV100, HPV106, HPV108, HPV109, HPV110, HPV111, HPV113, HPV120, HPV121, HPV122, HPV133, HPV139, HPV150, HPV151, HPV155, HPV156, HPV180, or HPV204.

Clause 42. The immunogenic composition of any one of clauses 35-38, wherein the at least one synthetic polypeptide encodes a CTL epitope from the HPV16 E6 antigen.

Clause 43. The immunogenic composition of clause 42, wherein the CTL epitope from the HPV16 E6 antigen is selected from the group consisting of IILECVYCK (SEQ ID NO:26), ISEYRHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43).

Clause 44. The immunogenic composition of clause 42 or 43, wherein the HPV-associated disease is caused by HPV18, HPV31, HPV33, HPV35, HPV39, HPV45, HPV51, HPV52, HPV53, HPV56, HPV58, HPV67, HPV68, HPV70, HPV73, HPV82, HPV85, or HPV97.

Clause 45. The immunogenic composition of any one of clauses 35-38, wherein the at least one synthetic polypeptide encodes a CTL epitope from the HPV16 E7 antigen.

Clause 46. The immunogenic composition of clause 45, wherein the CTL epitope from the HPV16 E7 antigen is selected from the group consisting of LQPETTDLY (SEQ ID NO:46), HGDTPTLHEY (SEQ ID NO:47), TPTLHEYML (SEQ ID NO:51), and QPETTDLYCY (SEQ ID NO:52).

Clause 47. The immunogenic composition of clause 45 or 46, wherein the HPV-associated disease is caused by HPV6, HPV7, HPV11, HPV16, HPV31, HPV33, HPV35, HPV52, HPV58, HPV67, HPV71, HPV73, or HPV106.

Clause 48. A method of treating a subject having a human papillomavirus (HPV)-associated disease, the method comprising administering an immunogenic composition comprising at least one synthetic polypeptide encoding a cytotoxic T lymphocyte (CTL) epitope derived from E2, E6, or E7 human papillomavirus subtype 16 (HPV16) antigens, and a pharmaceutically acceptable carrier or excipient; wherein administration of the composition to the subject induces an immune response against the HPV16-associated disease and treats the subject.

Clause 49. The method of clause 48, wherein the HPV16-associated disease is selected from the group consisting of cervical cancers, anal cancers, head and neck cancers, vaginal cancers, vulvar cancers, penile cancers, and rectal cancers.

Clause 50. The method of clause 48 or 49, wherein the HPV16-associated disease is a head and neck squamous cell carcinoma (HNSCC).

Clause 51. The immunogenic composition of any one of clauses 48-50, wherein the HPV-associated disease is caused by HPV subtype 1, HPV subtype 2, HPV subtype 6, HPV subtype 7, HPV subtype 11, HPV subtype 16, HPV subtype 18, HPV subtype 22, HPV subtype 23, HPV subtype 26, HPV subtype 31, HPV subtype 33, HPV subtype 34, HPV subtype 35, HPV subtype 37, HPV subtype 38, HPV subtype 39, HPV subtype 41, HPV subtype 42, HPV subtype 43, HPV subtype 44, HPV subtype 45, HPV subtype 51, HPV subtype 52, HPV subtype 53, HPV subtype 54, HPV subtype 56, HPV subtype 58, HPV subtype 59, HPV subtype 62, HPV subtype 63, HPV subtype 66, HPV subtype 67, HPV subtype 68, HPV subtype 69, HPV subtype 70, HPV subtype 71, HPV subtype 73, HPV subtype 77, HPV subtype 81, HPV subtype 82, HPV subtype 85, HPV subtype 86, HPV subtype 89, HPV subtype 91, HPV subtype 92, HPV subtype 96, HPV subtype 97, HPV subtype 100, HPV subtype 106, HPV subtype 108, HPV subtype 109, HPV subtype 110, HPV subtype 111, HPV subtype 113, HPV subtype 120, HPV subtype 121, HPV subtype 122, HPV subtype 133, HPV subtype 139, HPV subtype 150, HPV subtype 151, HPV subtype 155, HPV subtype 156, HPV subtype 180, or HPV subtype 204.

Clause 52. The method of any one of clauses 48-51, wherein the at least one synthetic polypeptide encodes a CTL epitope from the HPV16 E2 antigen.

Clause 53. The method of clause 52, wherein the CTL epitope from the HPV16 E2 antigen is selected from the group consisting of RLECAIYYK (SEQ ID NO:4), VYL-TAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAP-ILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24).

Clause 54. The immunogenic composition of clause 52 or 53, wherein the HPV-associated disease is caused by HPV1, HPV2, HPV16, HPV18, HPV22, HPV23, HPV26, HPV31, HPV33, HPV34, HPV35, HPV37, HPV38, HPV39, HPV41, HPV42, HPV43, HPV44, HPV45, HPV51, HPV52, HPV53, HPV54, HPV56, HPV59, HPV62, HPV63, HPV66, HPV67, HPV68, HPV69, HPV70, HPV71, HPV77, HPV81, HPV82, HPV85, HPV86, HPV89, HPV91, HPV92, HPV96, HPV97, HPV100, HPV106, HPV108, HPV109, HPV110, HPV111, HPV113, HPV120, HPV121, HPV122, HPV133, HPV139, HPV150, HPV151, HPV155, HPV156, HPV180, or HPV204.

Clause 55. The method of any one of clauses 48-51, wherein the at least one synthetic polypeptide encodes a CTL epitope from the HPV16 E6 antigen.

Clause 56. The method of clause 55, wherein the CTL epitope from the HPV16 E6 antigen is selected from the group consisting of IILECVYCK (SEQ ID NO:26), ISEY-RHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43).

Clause 57. The immunogenic composition of clause 55 or 56, wherein the HPV-associated disease is caused by HPV18, HPV31, HPV33, HPV35, HPV39, HPV45, HPV51, HPV52, HPV53, HPV56, HPV58, HPV67, HPV68, HPV70, HPV73, HPV82, HPV85, or HPV97.

Clause 58. The method of any one of clauses 48-51, wherein the at least one synthetic polypeptide encodes a CTL epitope from the HPV16 E7 antigen.

Clause 59. The method of clause 58, wherein the CTL epitope from the HPV16 E7 antigen is selected from the group consisting of LQPETTDLY (SEQ ID NO:46), HGDTPTLHEY (SEQ ID NO:47), TPTLHEYML (SEQ ID NO:51), and QPETTDLYCY (SEQ ID NO:52).

Clause 60. The immunogenic composition of clause 58 or 59, wherein the HPV-associated disease is caused by HPV6, HPV7, HPV11, HPV16, HPV31, HPV33, HPV35, HPV52, HPV58, HPV67, HPV71, HPV73, or HPV106.

Clause 61. The method of any one of clauses 48-60, wherein the immunogenic composition further comprises an immune checkpoint inhibitor.

Clause 62. The method of clause 61, wherein the immune checkpoint inhibitor is a programmed cell death protein 1 (PD-1) inhibitor.

Clause 63. The method of any one of clauses 48-60, wherein the immunogenic composition further comprises an Indoleamine 2,3-dioxygenase 1 (IDO-1) inhibitor.

Clause 64. A method of detecting a human papillomavirus (HPV)-associated disease in a subject, the method comprising obtaining a biological sample from a subject, wherein the biological sample comprises T cells; contacting the biological sample with a MHC class I peptide tetramer composition comprising at least one synthetic MHC class I molecule and at least one synthetic polypeptide encoding a cytotoxic T lymphocyte (CTL) epitope derived from E2, E6, or E7 human papillomavirus subtype 16 (HPV16) antigens, wherein the at least one synthetic MHC class I molecule is bound to the at least one synthetic polypeptide encoding the CTL epitope derived from E2, E6, or E7 HPV16 antigens; detecting the presence of T cells bound to the synthetic polypeptide encoding the CTL epitope derived from E2, E6, or E7 HPV16 antigens.

Clause 65. The method of clause 64, wherein detecting the presence of T cells comprises flow cytometry or fluorescence-activated cell sorting.

Clause 66. The method of clause 64 or 65, wherein the at least one synthetic peptide encodes a CTL epitope from the HPV16 E2 antigen.

Clause 67. The method of clause 66, wherein the CTL epitope from the HPV16 E2 antigen is selected from the group consisting of RLECAIYYK (SEQ ID NO:4), VYL-TAPTGCI (SEQ ID NO:6), SPEIIRQHL (SEQ ID NO:7), VVEGQVDYY (SEQ ID NO:9), ILTAFNSSHK (SEQ ID NO:12), LTAPTGCIKK (SEQ ID NO:13), HPAATHTKAV (SEQ ID NO:14), LAVSKNKAL (SEQ ID NO:15), DSAP-ILTAF (SEQ ID NO:16), LQDVSLEVY (SEQ ID NO:17), YLTAPTGCI (SEQ ID NO:18), QVILCPTSV (SEQ ID NO:19), NPCHTTKLL (SEQ ID NO:22), GIRTYFVQF (SEQ ID NO:23), and YYVHEGIRTY (SEQ ID NO:24).

Clause 68. The immunogenic composition of clause 66 or 67, wherein the HPV-associated disease is caused by HPV1, HPV2, HPV16, HPV18, HPV22, HPV23, HPV26, HPV31, HPV33, HPV34, HPV35, HPV37, HPV38, HPV39, HPV41, HPV42, HPV43, HPV44, HPV45, HPV51, HPV52, HPV53, HPV54, HPV56, HPV59, HPV62, HPV63, HPV66, HPV67, HPV68, HPV69, HPV70, HPV71, HPV77, HPV81, HPV82, HPV85, HPV86, HPV89, HPV91, HPV92, HPV96, HPV97, HPV100, HPV106, HPV108, HPV109, HPV110, HPV111, HPV113, HPV120, HPV121, HPV122, HPV133, HPV139, HPV150, HPV151, HPV155, HPV156, HPV180, or HPV204.

Clause 69. The method of clause 64 or 65, wherein the at least one synthetic peptide encodes CTL epitope from the HPV16 E6 antigen.

Clause 70. The method of clause 69, wherein the CTL epitope from the HPV16 E6 antigen is selected from the group consisting of IILECVYCK (SEQ ID NO:26), ISEY-RHYCY (SEQ ID NO:27), IVYRDGNPY (SEQ ID NO:28), TTLEQQYNK (SEQ ID NO:31), CPEEKQRHL (SEQ ID NO:39), and LLIRCINCQK (SEQ ID NO:43).

Clause 71. The immunogenic composition of clause 69 or 70, wherein the HPV-associated disease is caused by HPV18, HPV31, HPV33, HPV35, HPV39, HPV45, HPV51, HPV52, HPV53, HPV56, HPV58, HPV67, HPV68, HPV70, HPV73, HPV82, HPV85, or HPV97.

Clause 72. The method of clause 64 or 65, wherein the at least one synthetic peptide encodes a CTL epitope from the HPV16 E7 antigen.

Clause 73. The method of clause 72, wherein the CTL epitope from the HPV16 E7 antigen is selected from the group consisting of LQPETTDLY (SEQ ID NO:46), HGDTPTLHEY (SEQ ID NO:47), TPTLHEYML (SEQ ID NO:51), and QPETTDLYCY (SEQ ID NO:52).

Clause 74. The immunogenic composition of clause 72 or 73, wherein the HPV-associated disease is caused by HPV6, HPV7, HPV11, HPV16, HPV31, HPV33, HPV35, HPV52, HPV58, HPV67, HPV71, HPV73, or HPV106.

Clause 75. The method of any one of clauses 64-74, wherein the MHC class I peptide tetramer composition further comprises a ligand.

Clause 76. The method of any one of clauses 64-74, wherein the MHC class I peptide tetramer composition further comprises a label.

Clause 77. The method of clause 76, wherein the label comprises a fluorescent molecule, a luminescent molecule, or a radioactive molecule.

Clause 78. The method of any one of clauses 64-74, wherein the MHC class I molecule comprises a self-assembling protein domain.

What is claimed is:

1. An immunogenic composition for treating a subject having a HPV16-associated disease, the composition comprising:
    at least one synthetic polypeptide comprising a cytotoxic T lymphocyte (CTL) epitope from an E2 human papillomavirus subtype 16 (HPV16) antigen, the CTL epitope comprising an amino acid sequence comprising VYLTAPTGCI (SEQ ID NO: 6), SPEIIRQHL (SEQ ID NO: 7), VVEGQVDYY (SEQ ID NO: 9), ILTAFNSSHK (SEQ ID NO: 12), HPAATHTKAV (SEQ ID NO: 14), DSAPILTAF (SEQ ID NO: 16), LQDVSLEVY (SEQ ID NO: 17), YLTAPTGCI (SEQ ID NO: 18), QVILCPTSV (SEQ ID NO: 19), NPCHTTKLL (SEQ ID NO: 22), GIRTYFVQF (SEQ ID NO: 23), or YYVHEGIRTY (SEQ ID NO: 24);
    an immune checkpoint inhibitor; and
    a pharmaceutically acceptable carrier or excipient;
    wherein the immune checkpoint inhibitor comprises a programmed cell death protein 1 (PD-1) inhibitor, an Indoleamine 2,3-dioxygenase 1 (IDO-1) inhibitor, or a combination thereof, and
    wherein the synthetic polypeptide is no ore than 10 amino acids in length.

2. The immunogenic composition of claim 1, wherein the HPV16-associated disease is selected from the group consisting of cervical cancers, anal cancers, head and neck cancers, vaginal cancers, vulvar cancers, penile cancers, and rectal cancers.

3. The immunogenic composition of claim 2, wherein the HPV16-associated disease is a head and neck squamous cell carcinoma (HNSCC).

4. A method of treating a subject having a HPV16-associated disease, the method comprising:
    administering an immunogenic composition comprising at least one synthetic polypeptide comprising a cytotoxic T lymphocyte (CTL) epitope from an E2 human papillomavirus subtype 16 (HPV16) antigen, the CTL epitope comprising an amino acid sequence comprising VYLTAPTGCI (SEQ ID NO: 6), SPEIIRQHL (SEQ ID NO: 7), VVEGQVDYY (SEQ ID NO: 9), ILTAFNSSHK (SEQ ID NO: 12), HPAATHTKAV (SEQ ID NO: 14), DSAPILTAF (SEQ ID NO: 16), LQDVSLEVY (SEQ ID NO: 17), YLTAPTGCI (SEQ ID NO: 18), QVILCPTSV (SEQ ID NO: 19), NPCHTTKLL (SEQ ID NO: 22), GIRTYFVQF (SEQ ID NO: 23), or YYVHEGIRTY (SEQ ID NO: 24), an immune checkpoint inhibitor, and a pharmaceutically acceptable carrier or excipient;
    wherein the immune checkpoint inhibitor comprises a programmed cell death protein 1 (PD-1) inhibitor, an Indoleamine 2,3-dioxygenase 1 (IDO-1) inhibitor, or a combination thereof;
    wherein the synthetic polypeptide is no ore than 10 amino acids in length; and
    wherein administration of the composition to the subject induces an immune response against the HPV16-associated disease and treats the subject.

5. The method of claim 4, wherein the HPV16-associated disease is selected from the group consisting of cervical cancers, anal cancers, head and neck cancers, vaginal cancers, vulvar cancers, penile cancers, and rectal cancers.

6. The method of claim 5, wherein the HPV16-associated disease is a head and neck squamous cell carcinoma (HN-SCC).

* * * * *

SEQUENCE LISTING

```
<160> NUMBER OF SEQ ID NOS: 60

<210> SEQ ID NO 1
<211> LENGTH: 9
<212> TYPE: PRT
<213> ORGANISM: Human papillomavirus type 16

<400> SEQUENCE: 1

Lys Ser Ala Ile Val Thr Leu Thr Tyr
1               5

<210> SEQ ID NO 2
<211> LENGTH: 9
<212> TYPE: PRT
<213> ORGANISM: Human papillomavirus type 16

<400> SEQUENCE: 2

Thr Leu Gln Asp Val Ser Leu Glu Val
1               5

<210> SEQ ID NO 3
<211> LENGTH: 10
<212> TYPE: PRT
<213> ORGANISM: Human papillomavirus type 16

<400> SEQUENCE: 3

Tyr Ile Cys Glu Glu Ala Ser Val Thr Val
1               5                   10

<210> SEQ ID NO 4
<211> LENGTH: 9
<212> TYPE: PRT
<213> ORGANISM: Human papillomavirus type 16

<400> SEQUENCE: 4

Arg Leu Glu Cys Ala Ile Tyr Tyr Lys
1               5

<210> SEQ ID NO 5
<211> LENGTH: 9
<212> TYPE: PRT
<213> ORGANISM: Human papillomavirus type 16

<400> SEQUENCE: 5

Asn Thr Thr Pro Ile Val His Leu Lys
1               5

<210> SEQ ID NO 6
<211> LENGTH: 10
<212> TYPE: PRT
```

```
<213> ORGANISM: Human papillomavirus type 16

<400> SEQUENCE: 6

Val Tyr Leu Thr Ala Pro Thr Gly Cys Ile
1               5                   10

<210> SEQ ID NO 7
<211> LENGTH: 9
<212> TYPE: PRT
<213> ORGANISM: Human papillomavirus type 16

<400> SEQUENCE: 7

Ser Pro Glu Ile Ile Arg Gln His Leu
1               5

<210> SEQ ID NO 8
<211> LENGTH: 9
<212> TYPE: PRT
<213> ORGANISM: Human papillomavirus type 16

<400> SEQUENCE: 8

Tyr Arg Phe Lys Lys His Cys Thr Leu
1               5

<210> SEQ ID NO 9
<211> LENGTH: 9
<212> TYPE: PRT
<213> ORGANISM: Human papillomavirus type 16

<400> SEQUENCE: 9

Val Val Glu Gly Gln Val Asp Tyr Tyr
1               5

<210> SEQ ID NO 10
<211> LENGTH: 9
<212> TYPE: PRT
<213> ORGANISM: Human papillomavirus type 16

<400> SEQUENCE: 10

Ala Leu Gln Ala Ile Glu Leu Gln Leu
1               5

<210> SEQ ID NO 11
<211> LENGTH: 9
<212> TYPE: PRT
<213> ORGANISM: Human papillomavirus type 16

<400> SEQUENCE: 11

Thr Leu Tyr Thr Ala Val Ser Ser Thr
1               5

<210> SEQ ID NO 12
<211> LENGTH: 10
<212> TYPE: PRT
<213> ORGANISM: Human papillomavirus type 16

<400> SEQUENCE: 12

Ile Leu Thr Ala Phe Asn Ser Ser His Lys
1               5                   10

<210> SEQ ID NO 13
<211> LENGTH: 10
<212> TYPE: PRT
<213> ORGANISM: Human papillomavirus type 16
```

-continued

<400> SEQUENCE: 13

Leu Thr Ala Pro Thr Gly Cys Ile Lys Lys
1               5                   10

<210> SEQ ID NO 14
<211> LENGTH: 10
<212> TYPE: PRT
<213> ORGANISM: Human papillomavirus type 16

<400> SEQUENCE: 14

His Pro Ala Ala Thr His Thr Lys Ala Val
1               5                   10

<210> SEQ ID NO 15
<211> LENGTH: 9
<212> TYPE: PRT
<213> ORGANISM: Human papillomavirus type 16

<400> SEQUENCE: 15

Leu Ala Val Ser Lys Asn Lys Ala Leu
1               5

<210> SEQ ID NO 16
<211> LENGTH: 9
<212> TYPE: PRT
<213> ORGANISM: Human papillomavirus type 16

<400> SEQUENCE: 16

Asp Ser Ala Pro Ile Leu Thr Ala Phe
1               5

<210> SEQ ID NO 17
<211> LENGTH: 9
<212> TYPE: PRT
<213> ORGANISM: Human papillomavirus type 16

<400> SEQUENCE: 17

Leu Gln Asp Val Ser Leu Glu Val Tyr
1               5

<210> SEQ ID NO 18
<211> LENGTH: 9
<212> TYPE: PRT
<213> ORGANISM: Human papillomavirus type 16

<400> SEQUENCE: 18

Tyr Leu Thr Ala Pro Thr Gly Cys Ile
1               5

<210> SEQ ID NO 19
<211> LENGTH: 9
<212> TYPE: PRT
<213> ORGANISM: Human papillomavirus type 16

<400> SEQUENCE: 19

Gln Val Ile Leu Cys Pro Thr Ser Val
1               5

<210> SEQ ID NO 20
<211> LENGTH: 10
<212> TYPE: PRT
<213> ORGANISM: Human papillomavirus type 16

<400> SEQUENCE: 20

```
Thr Leu Lys Cys Leu Arg Tyr Arg Phe Lys
1               5                  10
```

<210> SEQ ID NO 21
<211> LENGTH: 10
<212> TYPE: PRT
<213> ORGANISM: Human papillomavirus type 16

<400> SEQUENCE: 21

```
Arg Tyr Arg Phe Lys Lys His Cys Thr Leu
1               5                  10
```

<210> SEQ ID NO 22
<211> LENGTH: 9
<212> TYPE: PRT
<213> ORGANISM: Human papillomavirus type 16

<400> SEQUENCE: 22

```
Asn Pro Cys His Thr Thr Lys Leu Leu
1               5
```

<210> SEQ ID NO 23
<211> LENGTH: 9
<212> TYPE: PRT
<213> ORGANISM: Human papillomavirus type 16

<400> SEQUENCE: 23

```
Gly Ile Arg Thr Tyr Phe Val Gln Phe
1               5
```

<210> SEQ ID NO 24
<211> LENGTH: 10
<212> TYPE: PRT
<213> ORGANISM: Human papillomavirus type 16

<400> SEQUENCE: 24

```
Tyr Tyr Val His Glu Gly Ile Arg Thr Tyr
1               5                  10
```

<210> SEQ ID NO 25
<211> LENGTH: 9
<212> TYPE: PRT
<213> ORGANISM: Human papillomavirus type 16

<400> SEQUENCE: 25

```
Glu Tyr Arg His Tyr Cys Tyr Ser Leu
1               5
```

<210> SEQ ID NO 26
<211> LENGTH: 9
<212> TYPE: PRT
<213> ORGANISM: Human papillomavirus type 16

<400> SEQUENCE: 26

```
Ile Ile Leu Glu Cys Val Tyr Cys Lys
1               5
```

<210> SEQ ID NO 27
<211> LENGTH: 9
<212> TYPE: PRT
<213> ORGANISM: Human papillomavirus type 16

<400> SEQUENCE: 27

```
Ile Ser Glu Tyr Arg His Tyr Cys Tyr
1               5
```

```
<210> SEQ ID NO 28
<211> LENGTH: 9
<212> TYPE: PRT
<213> ORGANISM: Human papillomavirus type 16

<400> SEQUENCE: 28

Ile Val Tyr Arg Asp Gly Asn Pro Tyr
1               5

<210> SEQ ID NO 29
<211> LENGTH: 9
<212> TYPE: PRT
<213> ORGANISM: Human papillomavirus type 16

<400> SEQUENCE: 29

Lys Leu Pro Gln Leu Cys Thr Glu Leu
1               5

<210> SEQ ID NO 30
<211> LENGTH: 10
<212> TYPE: PRT
<213> ORGANISM: Human papillomavirus type 16

<400> SEQUENCE: 30

Arg Pro Arg Lys Leu Pro Gln Leu Cys Thr
1               5                   10

<210> SEQ ID NO 31
<211> LENGTH: 9
<212> TYPE: PRT
<213> ORGANISM: Human papillomavirus type 16

<400> SEQUENCE: 31

Thr Thr Leu Glu Gln Gln Tyr Asn Lys
1               5

<210> SEQ ID NO 32
<211> LENGTH: 10
<212> TYPE: PRT
<213> ORGANISM: Human papillomavirus type 16

<400> SEQUENCE: 32

Ala Val Cys Asp Lys Cys Leu Lys Phe Tyr
1               5                   10

<210> SEQ ID NO 33
<211> LENGTH: 9
<212> TYPE: PRT
<213> ORGANISM: Human papillomavirus type 16

<400> SEQUENCE: 33

Cys Tyr Ser Leu Tyr Gly Thr Thr Leu
1               5

<210> SEQ ID NO 34
<211> LENGTH: 9
<212> TYPE: PRT
<213> ORGANISM: Human papillomavirus type 16

<400> SEQUENCE: 34

Leu Leu Arg Arg Glu Val Tyr Asp Phe
1               5
```

```
<210> SEQ ID NO 35
<211> LENGTH: 10
<212> TYPE: PRT
<213> ORGANISM: Human papillomavirus type 16

<400> SEQUENCE: 35

Asn Pro Tyr Ala Val Cys Asp Lys Cys Leu
1               5                   10

<210> SEQ ID NO 36
<211> LENGTH: 10
<212> TYPE: PRT
<213> ORGANISM: Human papillomavirus type 16

<400> SEQUENCE: 36

Thr Ile His Asp Ile Ile Leu Glu Cys Val
1               5                   10

<210> SEQ ID NO 37
<211> LENGTH: 9
<212> TYPE: PRT
<213> ORGANISM: Human papillomavirus type 16

<400> SEQUENCE: 37

Val Cys Asp Lys Cys Leu Lys Phe Tyr
1               5

<210> SEQ ID NO 38
<211> LENGTH: 10
<212> TYPE: PRT
<213> ORGANISM: Human papillomavirus type 16

<400> SEQUENCE: 38

Tyr Ala Val Cys Asp Lys Cys Leu Lys Phe
1               5                   10

<210> SEQ ID NO 39
<211> LENGTH: 9
<212> TYPE: PRT
<213> ORGANISM: Human papillomavirus type 16

<400> SEQUENCE: 39

Cys Pro Glu Glu Lys Gln Arg His Leu
1               5

<210> SEQ ID NO 40
<211> LENGTH: 10
<212> TYPE: PRT
<213> ORGANISM: Human papillomavirus type 16

<400> SEQUENCE: 40

Cys Val Tyr Cys Lys Gln Gln Leu Leu Arg
1               5                   10

<210> SEQ ID NO 41
<211> LENGTH: 9
<212> TYPE: PRT
<213> ORGANISM: Human papillomavirus type 16

<400> SEQUENCE: 41

Asp Lys Lys Gln Arg Phe His Asn Ile
1               5

<210> SEQ ID NO 42
<211> LENGTH: 9
```

```
<212> TYPE: PRT
<213> ORGANISM: Human papillomavirus type 16

<400> SEQUENCE: 42

Phe Ala Phe Arg Asp Leu Cys Ile Val
1               5

<210> SEQ ID NO 43
<211> LENGTH: 10
<212> TYPE: PRT
<213> ORGANISM: Human papillomavirus type 16

<400> SEQUENCE: 43

Leu Leu Ile Arg Cys Ile Asn Cys Gln Lys
1               5                   10

<210> SEQ ID NO 44
<211> LENGTH: 9
<212> TYPE: PRT
<213> ORGANISM: Human papillomavirus type 16

<400> SEQUENCE: 44

Tyr Gly Thr Thr Leu Glu Gln Gln Tyr
1               5

<210> SEQ ID NO 45

<400> SEQUENCE: 45

000

<210> SEQ ID NO 46
<211> LENGTH: 9
<212> TYPE: PRT
<213> ORGANISM: Human papillomavirus type 16

<400> SEQUENCE: 46

Leu Gln Pro Glu Thr Thr Asp Leu Tyr
1               5

<210> SEQ ID NO 47
<211> LENGTH: 10
<212> TYPE: PRT
<213> ORGANISM: Human papillomavirus type 16

<400> SEQUENCE: 47

His Gly Asp Thr Pro Thr Leu His Glu Tyr
1               5                   10

<210> SEQ ID NO 48
<211> LENGTH: 9
<212> TYPE: PRT
<213> ORGANISM: Human papillomavirus type 16

<400> SEQUENCE: 48

Leu Leu Met Gly Thr Leu Gly Ile Val
1               5

<210> SEQ ID NO 49
<211> LENGTH: 10
<212> TYPE: PRT
<213> ORGANISM: Human papillomavirus type 16

<400> SEQUENCE: 49

His Tyr Asn Ile Val Thr Phe Cys Cys Lys
```

1               5                    10

<210> SEQ ID NO 50
<211> LENGTH: 10
<212> TYPE: PRT
<213> ORGANISM: Human papillomavirus type 16

<400> SEQUENCE: 50

Gly Ile Val Cys Pro Ile Cys Ser Gln Lys
1               5                   10

<210> SEQ ID NO 51
<211> LENGTH: 9
<212> TYPE: PRT
<213> ORGANISM: Human papillomavirus type 16

<400> SEQUENCE: 51

Thr Pro Thr Leu His Glu Tyr Met Leu
1               5

<210> SEQ ID NO 52
<211> LENGTH: 10
<212> TYPE: PRT
<213> ORGANISM: Human papillomavirus type 16

<400> SEQUENCE: 52

Gln Pro Glu Thr Thr Asp Leu Tyr Cys Tyr
1               5                   10

<210> SEQ ID NO 53
<211> LENGTH: 9
<212> TYPE: PRT
<213> ORGANISM: Human papillomavirus type 16

<400> SEQUENCE: 53

Thr Leu His Glu Tyr Met Leu Asp Leu
1               5

<210> SEQ ID NO 54
<211> LENGTH: 9
<212> TYPE: PRT
<213> ORGANISM: Human papillomavirus type 16

<400> SEQUENCE: 54

Arg Ala His Tyr Asn Ile Val Thr Phe
1               5

<210> SEQ ID NO 55
<211> LENGTH: 9
<212> TYPE: PRT
<213> ORGANISM: Human papillomavirus type 16

<400> SEQUENCE: 55

Gly Thr Leu Gly Ile Val Cys Pro Ile
1               5

<210> SEQ ID NO 56
<211> LENGTH: 9
<212> TYPE: PRT
<213> ORGANISM: Human papillomavirus type 16

<400> SEQUENCE: 56

Ile Val Cys Pro Ile Cys Ser Gln Lys
1               5

```
<210> SEQ ID NO 57
<211> LENGTH: 10
<212> TYPE: PRT
<213> ORGANISM: Human papillomavirus type 16

<400> SEQUENCE: 57

Thr Phe Cys Cys Lys Cys Asp Ser Thr Leu
1               5                   10

<210> SEQ ID NO 58
<211> LENGTH: 9
<212> TYPE: PRT
<213> ORGANISM: Human papillomavirus type 16

<400> SEQUENCE: 58

Gln Ala Glu Pro Asp Arg Ala His Tyr
1               5

<210> SEQ ID NO 59
<211> LENGTH: 9
<212> TYPE: PRT
<213> ORGANISM: Human papillomavirus type 16

<400> SEQUENCE: 59

Tyr Met Leu Asp Leu Gln Pro Glu Thr
1               5

<210> SEQ ID NO 60
<211> LENGTH: 10
<212> TYPE: PRT
<213> ORGANISM: Human papillomavirus type 16

<400> SEQUENCE: 60

Tyr Met Leu Asp Leu Gln Pro Glu Thr Thr
1               5                   10
```